US012258615B2

(12) United States Patent
Li et al.

(10) Patent No.: US 12,258,615 B2
(45) Date of Patent: *Mar. 25, 2025

(54) COMPOSITIONS AND METHODS OF LABELING MITOCHONDRIAL NUCLEIC ACIDS AND SEQUENCING AND ANALYSIS THEREOF

(71) Applicant: King Abdullah University of Science and Technology, Thuwal (SA)

(72) Inventors: Mo Li, Thuwal (SA); Chongwei Bi, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 397 days.

This patent is subject to a terminal disclaimer.

(21) Appl. No.: 17/409,731

(22) Filed: Aug. 23, 2021

(65) Prior Publication Data
US 2022/0056502 A1   Feb. 24, 2022

Related U.S. Application Data

(63) Continuation-in-part of application No. PCT/IB2020/051894, filed on Mar. 4, 2020.

(60) Provisional application No. 63/073,865, filed on Sep. 2, 2020, provisional application No. 62/899,432, filed on Sep. 12, 2019, provisional application No. 62/899,142, filed on Sep. 11, 2019, provisional application No. 62/813,605, filed on Mar. 4, 2019.

(51) Int. Cl.
| | | |
|---|---|---|
| *C12Q 1/6806* | (2018.01) | |
| *C12Q 1/6869* | (2018.01) | |
| *C40B 40/08* | (2006.01) | |
| *G16B 30/10* | (2019.01) | |

(52) U.S. Cl.
CPC ......... *C12Q 1/6806* (2013.01); *C12Q 1/6869* (2013.01); *G16B 30/10* (2019.02); *C40B 40/08* (2013.01)

(58) Field of Classification Search
CPC .... C40B 40/08; C12Q 1/6806; C12Q 1/6869; G16B 30/10
See application file for complete search history.

(56) References Cited

U.S. PATENT DOCUMENTS

| | | |
|---|---|---|
| 2012/0208712 A1 | 8/2012 | Sibille |
| 2015/0133319 A1 | 5/2015 | Fu |
| 2018/0002738 A1 | 1/2018 | Wang |
| 2022/0259646 A1* | 8/2022 | Li .................... C12Q 1/6883 |

FOREIGN PATENT DOCUMENTS

| | | |
|---|---|---|
| WO | 2013173394 | 11/2013 |
| WO | 2016181128 | 11/2016 |

OTHER PUBLICATIONS

Barritt et al., "Mitochondrial DNA point mutation in human oocytes is associated with maternal age," Jan. 2000, Reproductive BioMedicine Online, vol. 1. No 3., 96-100. (Year: 2000).*
Goodwin et al., "1D genome sequencing on the oxford nanopore MinION. Current Protocols in Human Genetics," 2017, 94, 18.11. 1-18.11.14. (Year: 2017).*
Kim et al., "Analysis of mixtures using next generation sequencing of mitochondrial DNA hypervariable regions," Mar. 2015, Croat Med J., 56, 208-17 (Year: 2015).*
Adikusuma, et al., "Large deletions induced by Cas9 cleavage", Nature, 560(7717):E8-E9 (2018).
Ancora, et al., "Complete sequence of human mitochondrial DNA obtained by combining multiple displacement amplification and next30 generation sequencing on a single oocyte", Mitochondrial DNA Part A, DNA Mapping, Sequencing, and Analysis, 28(2):180-181 (2017).
Aravanis, et al., "Next-Generation Sequencing of Circulating Tumor DNA for Early Cancer Detection", Cell, 168(4): 571-574 (2017).
Bi, et al., "Long-read individual-molecule sequencing reveals CRISPR induced genetic heterogeneity in human ESCs", Genome Biol., 21(1):213, 14 pages (2020a).
Bi, et al., "Single-cell Individual Complete 5 mtDNA Sequencing Uncovers Hidden Mitochondrial Heterogeneity in Human and Mouse Oocytes," bioRxiv, 64 pages (2020b).
Brierley, et al., "Role of mitochondrial DNA mutations in human aging: implications for the central nervous system and muscle", Ann. Neurol., 43(2): 217-223, (1998).

(Continued)

*Primary Examiner* — Nancy J Leith
*Assistant Examiner* — Jessica D Parisi
(74) *Attorney, Agent, or Firm* — PABST PATENT GROUP LLP

(57) ABSTRACT

Methods of labeling, amplifying, and sequencing mitochondrial DNA are provided. The labeling methods typically include using polymerase-based extension of one or more unique molecular identifier (UMI) primers along a target mitochondrial DNA template, each UMI primer including a universal primer sequence, a unique molecular identifier sequence, and a mitochondrial DNA binding sequence. Amplification of the labeled-target mitochondrial DNA can include, for example, polymerase chain reaction (e.g., high-fidelity long-range). Methods of determining the sequence of labeled-target mitochondrial DNA can include use of a long-read sequencing platform. The methods may further including one or more of grouping sequences having the same UMI into one of more groups, determining the sequence of each labeled-target mitochondrial DNA by determining the consensus sequence of each group, and identifying polymorphisms in one or more of the labeled-target mitochondrial DNA. The methods can be used in, for example, preimplantation genetic testing.

20 Claims, 50 Drawing Sheets

Specification includes a Sequence Listing.

(56) References Cited

OTHER PUBLICATIONS

Burtner, et al., "Progeria syndromes and ageing: what is the connection?", Nat. Rev. Mol. Cell Biol., 11:567-578 (2010).
Cao, et al., "New evidence confirms that the mitochondrial bottleneck is generated without reduction of mitochondrial DNA content in early primordial germ cells of mice", PLoS genetics, 5(12):e1000756, 8 pages (2009).
Cao, et al., "The mitochondrial bottleneck occurs without reduction of mtDNA content in female mouse germ cells", Nature Genetics, 39(3):386-390 (2007).
Challen, et al., "Mouse Hematopoietic Stem Cell Identification and Analysis", Cytometry Part A, 75A:14-24 (2009).
Cheng, et al., "Mice with a targeted disruption of the Fanconi anemia homolog Fanca", Human Molecular Genetics, 9(12):1805-1811 (2000).
Cingolani, et al., "A program for annotating and predicting the effects of single nucleotide polymorphisms, SnpEff: SNPs in the genome of Drosophila melanogaster strain w(1118); iso-2; iso-3", Fly, 6(2): 80-92 (2012).
Coller, et al., "High frequency of homoplasmic mitochondrial DNA mutations in human tumors can be explained without selection", Nature Genetics, 28: 147-150 (2001).
Corral-Debrinski, et al., "Association of mitochondrial DNA damage with aging and coronary atherosclerotic heart disease", Mutat. Res., 275(3-6):169-180 (1992).
Cortopassi, et al., "Detection of a specific mitochondrial DNA deletion in tissues of older humans", Nucleic Acids Research, 18(23):6927-6933 (1990).
Cree, et al., "A reduction of mitochondrial DNA molecules during embryogenesis explains the rapid segregation of genotypes", Nature Genetics, 40(2):249-254 (2008).
Cretu, et al., "Mapping and phasing of structural variation in patient genomes using nanopore sequencing", Nat. Commun., 8:1326, 13 pages (2017).
D'Erchia, et al., "Tissue-specific mtDNA abundance from exome data and its correlation with mitochondrial transcription, mass and respiratory activity", Mitochondrion, 20:13-21 (2015).
De Vree, et al., "Targeted sequencing by proximity ligation for comprehensive variant detection and local haplotyping", Nat. Biotechnol., 32(10):1019-1025 (2014).
Duan, et al., "Recent Advances in Detecting Mitochondrial DNA Heteroplasmic Variations", Molecules, 23(2):323, 18 pages (2018).
Elliott, et al., "Pathogenic mitochondrial DNA mutations are common in the general Population", Am. J. Hum. Genet., 83(2):254-260 (2008).
Filges, et al., "Impact of Polymerase Fidelity on Background Error Rates in Next-Generation Sequencing with Unique Molecular Identifiers/Barcodes", Scientific Reports, 9(1):3503, 7 pages (2019).
Floros, et al., "Segregation of mitochondrial DNA heteroplasmy through a developmental genetic bottleneck in human embryos", Nature Cell Biology, 20(2):144-151 (2018).
Gehring, et al., "SomaticSignatures: inferring mutational signatures from single-nucleotide variants", Bioinformatics, 31(22):3673-3675 (2015).
Ghezzi, et al., "Mitochondrial DNA haplogroup K is associated with a lower risk of Parkinson's disease in Italians", Eur. J. Hum. Genet., 13:748-752 (2005).
Goodwin, et al., "Coming of age: ten years of next-generation sequencing technologies", Nature Reviews, 17:333-351 (2016).
Haapaniemi, et al., "CRISPR-Cas9 genome editing induces a p53-mediated DNA damage response", Nature Medicine, 24:927-930 (2018).
Han, et al., "An accurate and rapid continuous wavelet dynamic time warping algorithm for end-to-end mapping in ultra-long nanopore sequencing", Bioinformatics, 34(17):722-731 (2018).
Hiatt, et al., "Parallel, tag-directed assembly of locally derived short sequence reads", Nat. Methods, 7(2):119-122 (2010).
Hudson, et al., "Two-stage association study and meta-analysis of mitochondrial DNA variants in Parkinson disease", Neurology, 80:2042-2048 (2013).
Ihry, et al., "p53 inhibits CRISPR-Cas9 engineering in human pluripotent stem cells", Nature Medicine, 24:939-946 (2018).
Ingman, et al., "Rate variation between mitochondrial domains and adaptive evolution in humans", Human Molecular Genetics, 16(19): 2281-2287 (2007).
International Search Report for PCT/IB2020/051894 filed Mar. 4, 2020.
Jain, et al., "Nanopore sequencing and assembly of a human genome with ultra-long reads", Nat. Biotechnol., 36(4):338-345 (2018).
Ju, et al., "Origins and functional consequences of somatic mitochondrial DNA mutations in human cancer", eLife, 3: e02935, 28 pages (2014).
Kaschutnig, et al., "The Fanconi anemia pathway is required for efficient repair of stress-induced DNA damage in haematopoietic stem cells", Cell Cycle, 14(17):2734-2742 (2015).
Kauppila, et al., "Base-excision repair deficiency alone or combined with increased oxidative stress does not increase mtDNA point mutations in mice", Nucleic Acids Res., 46(13):6642-6669 (2018).
Kauppila, et al., "Mammalian Mitochondria and Aging: an Update", Cell Metab., 25: 57-71 (2017).
Kennedy, et al., "Ultra-sensitive sequencing reveals an age-related increase in somatic mitochondrial mutations that are inconsistent with oxidative damage", PLoS Genetics, 9(9): e1003794, 10 pages (2013).
Kim, et al., "The Role of Mitochondria in Oocyte and Early Embryo Health", OBM Genetics, 3:1, 29 pages (2019).
Kinde, et al., "Detection and quantification of rare mutations with massively parallel sequencing", PNAS, 108(23):9530-9535 (2011).
Koike-Yusa, et al., "Genome-wide recessive genetic screening in mammalian cells with a lentiviral CRISPR-guide RNA library", Nature Biotechnology, 32:267-273 (2014).
Koren, et al., "Canu: scalable and accurate long-read assembly via adaptive k-mer weighting and repeat separation", Genome Res., 27:722-736 (2017).
Kosicki, et al., "Repair of double-strand breaks induced by CRISPR-Cas9 leads to large deletions and complex rearrangements", Nat. Biotechnol., 36(8):765-771 (2018).
Kukat, et al., "Super-resolution microscopy reveals that mammalian mitochondrial nucleoids have a uniform size and frequently contain a single copy of mtDNA", PNAS, 108:13534-13539, doi: 10.1073/pnas.1109263108 (2011).
Ley, et al., "DNA sequencing of a cytogenetically normal acute myeloid leukemia genome", Nature, 456:66-72 (2008).
Li, "Minimap2: pairwise alignment for nucleotide sequences", Bioinformatics, 34(18):3094-3100 (2018).
Li, et al., "Extensive tissue-related and allele-related mtDNA heteroplasmy suggests positive selection for somatic mutations", PNAS, 112(8):2491-2496 (2015).
Li, et al., "Generation of Blastocyst-like Structures from Mouse Embryonic and Adult Cell Cultures", Cell, 179(3): 687-702.e618 (2019).
Li, et al., "The Sequence Alignment/Map format and SAMtools", Bioinformatics, 25:2078-2079 (2009).
Lin, et al., "Genome dynamics of the human embryonic kidney 293 lineage in response to cell biology manipulations", Nat. Commun., 5:4767, 12 pages (2014).
Loman, et al., "A complete bacterial genome assembled de novo using only nanopore sequencing data", Nat. Methods, 12:733-751 (2015).
Lott, et al., "mtDNA Variation and Analysis Using Mitomap and Mitomaster", Curr. Protoc. Bioinformatics, 44(123): 21-26 (2013).
Ludwig, et al., "Lineage Tracing in Humans Enabled by Mitochondrial Mutations and Single-Cell Genomics", Cell, 176(6):1325-1339.e22 (2019).
Ma, et al., "Inter-homologue repair in fertilized human eggs?", Nature, 548:413-419 (2017).
Martin, "Cutadapt removes adapter sequences from high-throughput sequencing reads", 17(1): 10-12 (2011).
Martincorena, et al., "High burden and pervasive positive selection of somatic mutations in normal human skin", Science, 348(6237):880-886 (2015).

(56) References Cited

OTHER PUBLICATIONS

Merkle, et al., "Human pluripotent stem cells recurrently acquire and expand dominant negative P53 mutations", Nature, 545(7653):229-233 (2017).
Minoche, et al., "Evaluation of genomic high-throughput sequencing data generated on Illumina HiSeq and Genome Analyzer systems", Genome Biol., 12:R112, 15 pages (2011).
Moehrle, et al., "Aging of hematopoietic stem cells: DNA damage and mutations?", Exp. Hematol., 44(10):895-901 (2016).
Monnot, et al., "Segregation of mtDNA throughout human embryofetal development: m.3243A>G as a model system", Hum. Mutat., 32(1):116-125 (2011).
Morris, et al., "Pervasive within-Mitochondrion Single-Nucleotide Variant Heteroplasmy as Revealed by Single-Mitochondrion Sequencing", Cell Rep., 21(10): 2706-2713 (2017).
Nei, et al., "Simple Methods for Estimating the Numbers of Synonymous and Nonsynonymous Nucleotide Substitutions", Mol. Biol. Evol., 3(5):418-426 (1986).
Ni, et al., "MitoRCA-seq reveals unbalanced cytocine to thymine transition in Polg mutant mice", Scientific Reports, 5:12049, 13 pages (2015).
Nielsen, "Molecular signatures of natural selection", Annu. Rev. Genet., 39: 197-218 (2005).
Norddahl, et al., "Accumulating mitochondrial DNA mutations drive premature hematopoietic aging phenotypes distinct from physiological stem cell aging", Cell Stem Cell, 8(5):499-510 (2011).
Okamura, et al., "an alternative pluripotent state confers interspeices chimaeric competency", Genes Genet. Syst., 90:405-405 (2015).
Palovcak, et al., "Maintenance of genome stability by Fanconi anemia proteins", Cell Biosci., 7(8) 18 pages (2017).
Parmar, et al., "Mouse models of Fanconi anemia", Mutat. Res., 668(1-2):133-140 (2009).
Payne, et al., "Deep resequencing of mitochondrial DNA", Methods in Molecular Biology, Mitochondrial Medicine, 1264:59-66 (2015).
Piko, et al., "Amounts of mitochondrial DNA and abundance of some mitochondrial gene transcripts in early mouse embryos", Dev. Biol., 123(2):364-374 (1987).
Rebolledo-Jaramillo, et al., "Maternal age effect and severe germline bottleneck in the inheritance of human mitochondrial DNA", PNAS, 111:15474-15479 (2014).
Salk, et al., "Enhancing the accuracy of next-generation sequencing for detecting rare and subclonal mutations", Nat. Rev. Genet., 19(5):269-285 (2018).
Santibanez-Koref, et al., "Assessing mitochondrial heteroplasmy using next generation sequencing: a note of caution", Mitochondrion, 46:302-306 (2019).
Schon, et al., "Human mitochondrial DNA: roles of inherited and somatic mutations", Nature Reviews, 13(12):878-890 (2012).
Sedlazeck, et al., "Accurate detection of complex structural variations using single-molecule sequencing", Nat. Methods, 15(6):461-468 (2018).
Shendure, et al., "Next-generation DNA sequencing", Nature Biotechnology, 26(10):1135-1145 (2008).
Simpson, et al., "Detecting DNA cytosine methylation using nanopore sequencing", Nat. Methods, 14(4):407-410 (2017).
Smith, et al., "UMI-tools: modeling sequencing errors in Unique Molecular Identifiers to improve quantification accuracy", Genome Res., 27: 491-499 (2017).
Sovic, et al., "Fast and sensitive mapping of nanopore sequencing reads with GraphMap", Nat. Commun., 7:11307, 11 pages (2016).
Sperling, et al., "The genetics of myelodysplastic syndrome: from clonal hematopoiesis to secondary leukemia", Nat. Rev. Cancer, 17(1):5-19 (2017).
Stewart, et al., The dynamics of mitochondrial DNA heteroplasmy: implications for human health and disease, Nature Reviews, 16(9):530-542 (2015).
Tajima, et al., "The development of novel quantification assay for mitochondrial DNA heteroplasmy aimed at preimplantation genetic diagnosis of Leigh encephalopathy", J. Assist Reprod. Genet., 24(6):227-232 (2007).
Tanaka, et al., "Strand asymmetry in human mitochondrial DNA mutations", Genomics, 22(2):327-335 (1994).
Thorburn, et al., "Healthy Baby Girl Born Following Pre-Implantation Genetic Diagnosis for Mitochondrial DNA 25 M.8993t > G Mutation", Molecular Genetics and Metabolism, 98(1-2):5-6 (2009).
Treff, et al., "Blastocyst preimplantation genetic diagnosis (PGD) of a mitochondrial DNA disorder", Fertil. Steril., 98(5):1236-1240 (2012).
Underhill, et al., "Use of Y chromosome and mitochondrial DNA population structure in tracing human migrations", Annu. Rev. Genet., 41:539-564 (2007).
Van Overbeek, et al., "DNA Repair Profiling Reveals Nonrandom Outcomes at Cas9-Mediated Breaks", Molecular Cell, 63(4):633-646 (2016).
Wai, et al., "The mitochondrial DNA genetic bottleneck results from replication of a subpopulation of genomes", Nature Genetics, 40(12):1484-1488 (2008).
Wallace, et al., "Mitochondrial DNA genetics and the heteroplasmy conundrum in evolution and disease", Cold Spring Harbor Perspectives in Biology, 5(11): a021220 (2013).
Walter, et al., "Exit from dormancy provokes DNA-damage-induced attrition in haematopoietic stem cells", Nature, 520(7548):549-552 (2015).
Weirather, et al., "Comprehensive comparison of Pacific Biosciences and Oxford Nanopore Technologies and their applications to transcriptome analysis", F1000Res 6:100, 32 pages (2017).
Wenger, et al., "Accurate circular consensus long-read sequencing improves variant detection and assembly of a human genome", Nature Biotechnology, 37(10):1155-1162 (2019).
Yang, et al., 'Derivation of Pluripotent Stem Cells with in Vivo Embryonic and Extraembryonic Potency, Cell, 169(2):243-257, e225 (2017).
Yao, et al., "Age-dependent accumulation of mtDNA mutations in murine hematopoietic stem cells is modulated by the nuclear genetic background", Hum. Mol. Genet., 16(3):286-294 (2007).
Yu, et al., "Effects of combined epidermal growth factor, brain-derived neurotrophic factor and insulin-like growth factor-1 on human oocyte maturation and early fertilized and cloned embryo development", Hum. Reprod., 27(7):2146-2159 (2012).
Yuan, et al., "Comprehensive molecular characterization of mitochondrial genomes in human cancers", Nature Genetics, 52(3):342-352 (2020).
Zagordi, et al., "Error correction of next-generation sequencing data and reliable estimation of HIV quasispecies", Nucleic Acids Res., 38(21):7400-7409 (2010).
Zaidi, et al., "Bottleneck and selection in the germline and maternal age influence transmission of mitochondrial DNA in human pedigrees", PNAS, 116(50):25172-25178 (2019).
Zhang, et al., "The mitochondrial DNA genetic bottleneck: inheritance and beyond", Essays Biochem., 62(3):225-234 (2018).
Zhou, et al., "Evaluating nanopore sequencing data processing pipelines for structural variation identification", Genome Biol., 20(1):237, 13 pages (2019).

\* cited by examiner

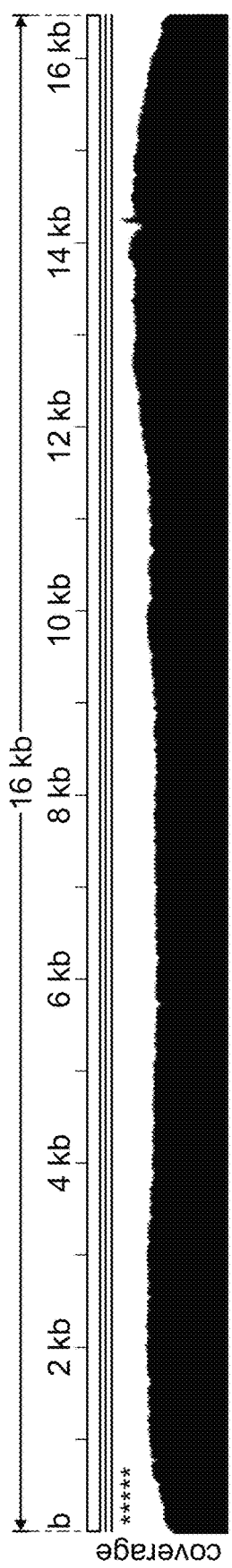
FIG. 2A
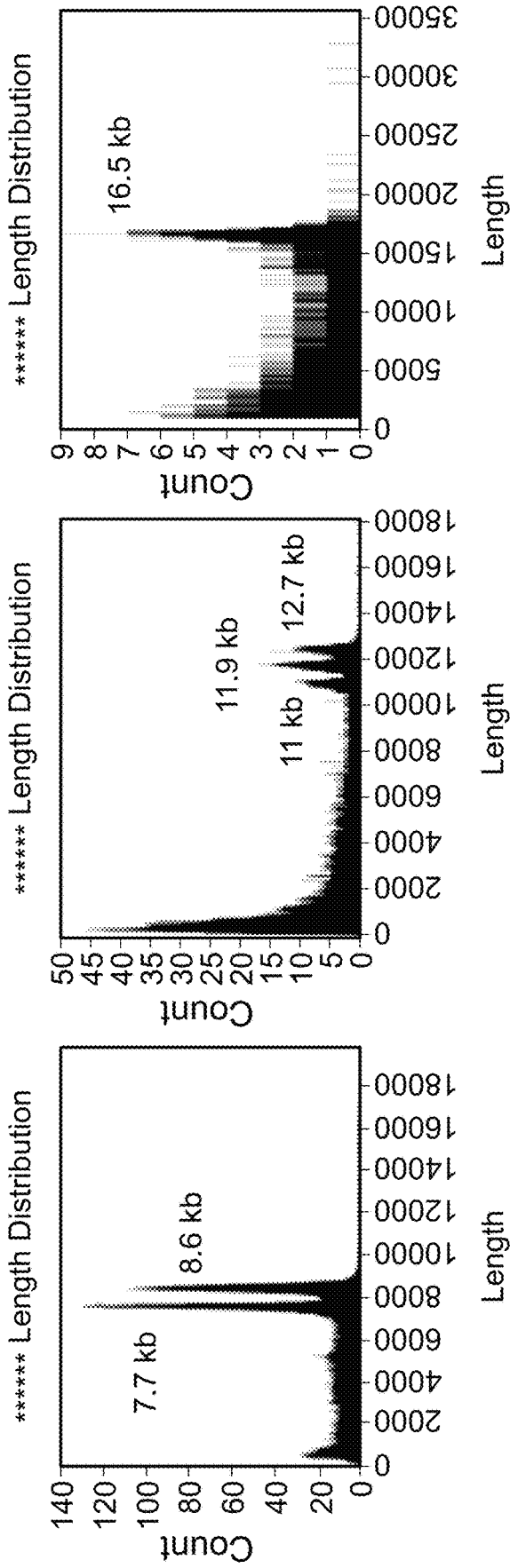
FIG. 2B
FIG. 2C
FIG. 2D

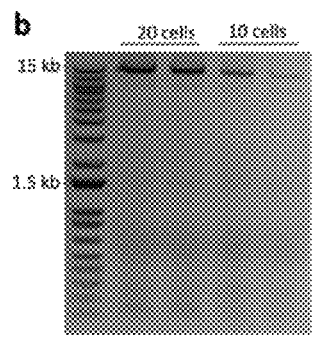
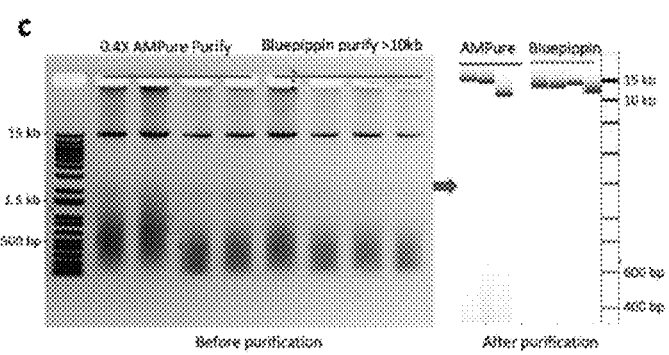
FIG. 4C  FIG. 4D
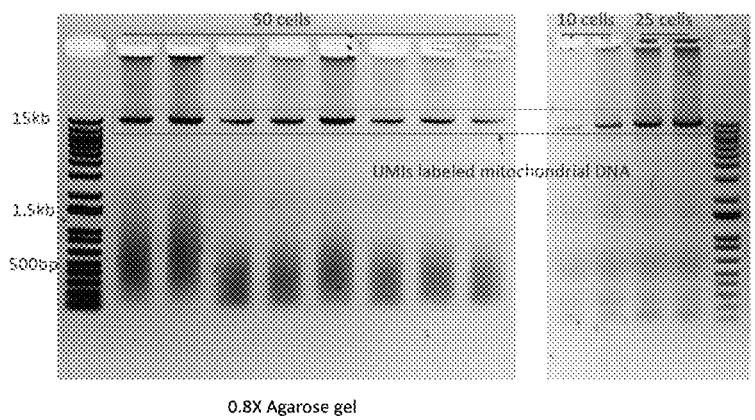
FIG. 4E
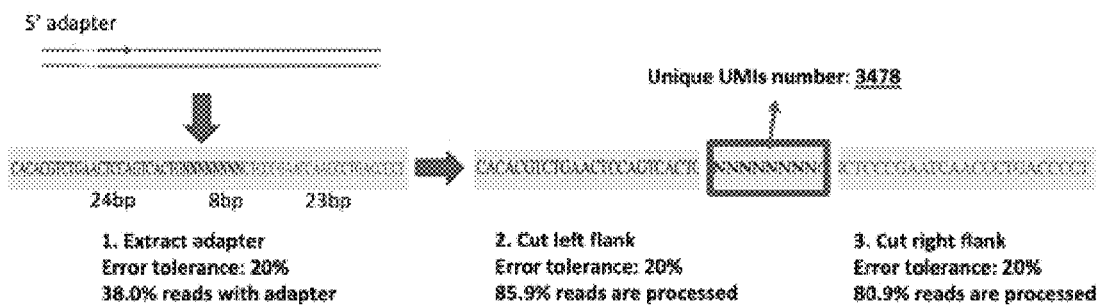
FIG. 4F

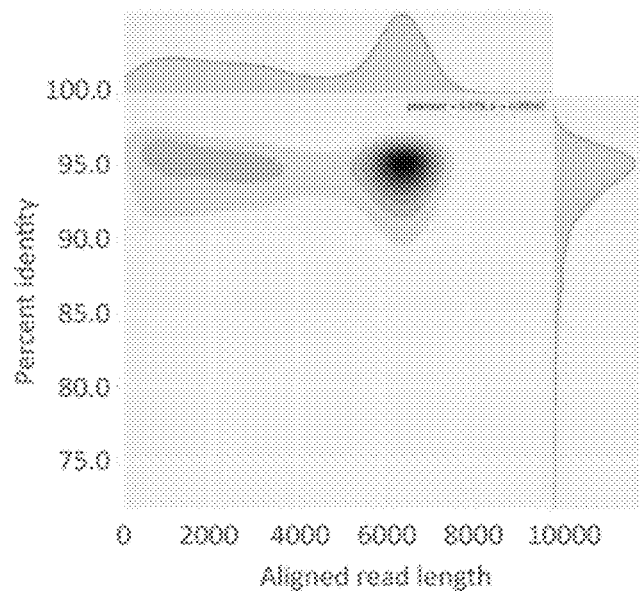

FIG. 14A

```
Pan1 sgRNA
WT  5'ACCTGGCCACGG|AGTACGTGTTCTCGGATTTCTTGCTGAA3'
    5'ACCTGGCCACGG|AAGTACGTGTTCTCGGATTTCTTGCTGA3'
    5'ACCTGGCCACGG|AGAGTACGTGTTCTCGGATTTCTTGCTG3'
    5'AC----10bp--|AGTACGTGTTCTCGGATTTCTTGCTGAA3'
    5'ACC---10bp--|GTACGTGTTCTCGGATTTCTTGCTGAA3'
 *  5'ACCT---9bp--|GTACGTGTTCTCGGATTTCTTGCTGAA3'
    5'ACCTG---13bp|------TGTTCTCGGATTTCTTGCTGAA3'
    5'ACCTG-------|--22bp--------ATTTCTTGCTGAA3'
    5'AACTGG--8bp-|-TACGTGTTCTCGGATTTCTTGCTGAA3'
    5'ACCTGGC-----|----23bp--------TTCTTGCTGAA3'
    5'ACCTGAAC-8bp|-----GTACGTGTTCTCGGTCTTGCTGAA3'
    5'AACTGGCCACG-|5bp-CGTGTTCTCGGATTTCTTGCTGAA3'
    5'ACCTGGCCACG-|-7bp---TGTTCTCGGATTTCTTGCTGAA3'
    5'ACCTGGCCACGG|---10bp---CTCGGATTTCTTGCTGAA3'
    5'AACTGGCCACGG|---8bp----TTCTCGGATTTCTTGCTGAA3'
 ■  5'ACCTGGCCACGGA|--7bp--TTCTCGGATTTCTTGCTGAA3'
    5'ACCTGGCCACGGA|--ACGTGTTCTCGGATTTCTTGCTGAA3'
```

COMPOSITIONS AND METHODS OF LABELING MITOCHONDRIAL NUCLEIC ACIDS AND SEQUENCING AND ANALYSIS THEREOF

CROSS-REFERENCE TO RELATED APPLICATIONS

This application claims priority to and benefit of U.S. Ser. No. 63/073,865, filed Sep. 2, 2020, and is a continuation-in-part of PCT/IB2020/051894 filed Mar. 4, 2020, which claims priority to and benefit of U.S. Ser. No. 62/813,605, filed Mar. 4, 2019, U.S. Ser. No. 62/899,142, filed Sep. 11, 2019, and U.S. Ser. No. 62/899,432, filed Sep. 12, 2019, each of which is specifically incorporated by reference herein in its entirety.

REFERENCE TO SEQUENCE LISTING

The Sequence Listing submitted as a text file named "KAUST_2021_025_02_CIP_ST25.txt", created on Nov. 15, 2021, and having a size of 13,873 bytes is hereby incorporated by reference pursuant to 37 C.F.R § 1.52(e)(5).

FIELD OF THE INVENTION

The field of the invention generally relates to compositions and methods for labeling and optionally amplifying a mitochondrial nucleic acid sequence, typically for sequencing.

BACKGROUND OF THE INVENTION

Mitochondria play vital roles in cellular metabolic and signaling processes such as ATP production, beta-oxidation of fatty acids, iron-sulfur cluster synthesis, calcium signaling, and apoptosis. Each human mitochondrion contains on average one copy of a 16.5 kb circular genome6-mtDNA—that is densely packed with 13 genes encoding core subunits of the oxidative phosphorylation complexes, 24 RNA genes, and a non-coding control region (D-loop region). Mitochondria and hence mtDNA undergo constant turnover even in non-dividing cells such as arrested primary oocytes[7, 8]. The demand for frequent DNA replication and the lack of histonized chromatin in mtDNA contribute to a mutation rate that is at least one order of magnitude higher than that of the human nuclear genome[2, 8, 9] Increasing evidence shows that the integrity of the mitochondrial genome has a crucial bearing on human reproductive health, diseases, and aging[1, 10]. Therefore, it is of great interest to characterize mtDNA mutations and elucidate their role in human diseases and aging, with the hope of developing new regenerative therapies.

It is well documented that heteroplasmic mutations are present at low levels in the general population and are among the most common causes of inherited metabolic diseases when present above a heteroplasmy threshold[11, 12]. Inherited mtDNA mutations are passed down via the female germline. During oogenesis mtDNA experiences a genetic bottleneck that could result in large swings in heteroplasmy levels between mother and child or between offspring[7, 8, 13]. The mitochondrial bottleneck can be attributed to a physical reduction of mtDNA content in female germline development[4, 14, 15], selective replication of mtDNA15, grouping of mtDNA into fewer segregating units[16, 17] or a combination of the above. Interestingly, humans have a more severe reduction of mtDNA segregation units[4, 7, 8]. mtDNA mutations have also been found in biopsies of healthy elderly individuals[18-20], thousands of which have been linked to late-onset diseases such as Parkinson's disease and cancers[21, 22]. Despite these clear evidence of the importance of mtDNA mutations in human health, fundamental understanding of the quantitative genetics of heteroplasmic mutations in oocytes and the origins (pre-existing rare germline vs. de novo somatic) and dynamics of heteroplasmic mutations in complex diseases remain scarce[23].

A main challenge of the field is the lack of quantitative analysis of the multitude of mitochondrial genomes at the individual-molecule level in single cells, which would be necessary to study the ontogeny, heterogeneity, dynamics, and genotype-phenotype relationship of mtDNA mutations. Current methods of mtDNA sequencing suffers from two seemingly paradoxical issues-amalgamation and fragmentation. Most studies of mtDNA genetics are based on short-read shotgun or amplicon next-generation sequencing (NGS)[7, 23-27]. These techniques average out the heterogeneity of mtDNA in two ways. Firstly, mtDNA genotypes of thousands of cells are averaged in bulk sequencing, thus masking variants in rare cells and cell-to-cell heterogeneity. Secondly, even in single cell analysis[28, 29], it was a composite genotype of all mtDNA rather than the true genotypes of individual mtDNA that was obtained. Additionally, due to the background error rate (0.1~1%) and contamination of nuclear mitochondrial DNA-like sequences (NUMTs) conventional short-read NGS methods are unreliable for detection of heteroplasmy below 1% in practice[8, 25, 26]. Additionally, the phenotypic significance of an mtDNA variant is strongly modified by other co-inherited variants2. However, short-read NGS cannot provide full haplotypes due to fragmentation of mtDNA molecules that is necessary for short-read sequencing, which largely prevents the study of linkage between heteroplasmy variants.

SUMMARY OF THE INVENTION

Methods of labeling genomic mitochondrial DNA are provided. The methods can include, for example, preparing labeled-target mitochondrial DNA by using polymerase-based extension of one or more unique molecular identifier (UMI) primers along a target mitochondrial DNA template, each UMI primer including a universal primer sequence, a unique molecular identifier (UMI) sequence, and a mitochondrial DNA binding sequence.

Methods of amplifying labeled-target mitochondrial DNA are also provided. The methods can include, for example, amplifying labeled-target mitochondrial DNA by one or more rounds of polymerase chain reaction (PCR) comprising a universal primer that binds to the universal primer sequence and one or more mitochondrial DNA primers that bind to a mitochondrial DNA sequence.

Methods of determining the sequence of labeled-target mitochondrial DNA are also provided. The methods can include, for example, optionally purifying the labeled-target mitochondrial DNA or the amplified labeled-target mitochondrial DNA, and using the labeled-target mitochondrial DNA or the amplified labeled-target mitochondrial DNA as a template or substrate for sequencing. The methods may further including one or more of grouping sequences having the same UMI into one of more groups, determining the sequence of each labeled-target mitochondrial DNA by determining the consensus sequence of each group, and identifying polymorphisms in one or more of the labeled-target mitochondrial DNA. The polymorphism can be, for example, a single nucleotide polymorphism (SNP).

The sequencing can include long-read sequencing technology, for example, a Nanopore MinION sequencer or a PacBio platform. The long-read sequencing technology can include preparing a 1D ligation library from the labeled amplicons. Analysis can be carried out using bioinformatics, and may include, for example, basecalling, sequence alignment(s), polymorphism identification or a combination thereof. An exemplary method is illustrated in FIG. 16C and its associate texted.

In some embodiments, the source of the target mitochondrial DNA template is any integer between 1 and 1,000,000 cells inclusive, or any range formed of two integers there between, for example, between 1 and 10,000, 1 and 1,000, 1 and 100, 1 and 10, or 1 single cell. The template can be from a single cell, or even one single mitochondrion. The target mitochondrial DNA template can be somatic cell(s) or germ cell(s) or embryonic tissue. In some embodiments, the target mitochondrial DNA template is oocyte(s) or pre-implantation embryonic tissue.

Preimplantation genetic testing incorporating the disclosed sequencing methods are also provided. In some embodiments, the methods include labeling and sequencing target mitochondrial DNA from oocyte(s) or pre-implantation embryonic tissue as disclosed herein, and identifying genomic mitochondrial mutations in the target mitochondrial DNA. The methods can further include determining if the oocyte(s) or pre-implantation embryo has or is likely to develop a mitochondrial disease or disorder when genomic mitochondrial mutation(s) that are associated with the mitochondrial disease or disorder are identified.

BRIEF DESCRIPTION OF THE DRAWINGS

FIGS. 2A-2D illustrate alignment and length distribution of reads generated by Nanopore MinION. FIG. 2A is a plot showing reads from a 16.5 kb amplicon sequencing mapped to the human mitochondrial genome. FIGS. 2B-2D are plots showing the length distribution of reads from amplicon sequencing. Long-length peaks from left to right are 7.7 kb, 8.6 kb, 11 kb, 11.9 kb, 12.7 kb, and 16.5 kb.

FIG. 3A is a bar graph showing a comparison of three alignment algorithms, graphmap, minimap2 and bwa-mem. FIG. 3B is a plot of the data set used for evaluating SNPs-calling algorithms. Three homozygous SNPs identified by Sanger sequencing are shown with respective coverage. FIG. 3C is a flow chart showing a pipeline for data analysis. Raw fast5 reads are basecalled by albacore, followed by trimming adapter using porechop. Refined fastq reads are mapped to reference using graphmap, subsequently analyzed by samtools to call SNPs.

FIGS. 4A-4E illustrates mtDNA labeling from one hundred of 293T cells. FIG. 4A is a schematic of a work flow for labeling mtDNA with UMIs from cells. FIG. 4B is a schematic of PCR-directed single DNA labeling with single-end UMIs. FIG. 4C is an electrophoretic gel showing 16.5 kb of UMIs labeled mtDNA are generated using the strategy shown in FIG. 4A. FIG. 4D is an electrophoretic gel showing small fragments are eliminated by BluePippin, while they remain after AMPure purification. FIG. 4E is an electrophoretic gel showing label mitochondrial DNA with UMIs in 50, 25, and 10 cells. FIG. 4F is a schematic illustrating a strategy used to extract UMIs. 3478 of unique UMIs are found. (SEQ ID NOS:52-55).

FIG. 14A is an aligned read length vs. percent identity plot using kernel density estimation of Nanopore sequencing data of a 6595 bp region encompassing the Cas9 cleavage. FIG. 14B-14C are alignments of individual alleles from Sanger sequencing of single-cell derived hESC clones after Cas9-directed mutagenesis in exon 1 of PANX1 using Pan1 sgRNA (14B (SEQ ID NOS:26-42)) or Pan3 sgRNA (14C (SEQ ID NOS:43-51)). The gRNA sequence (Pan1, CGGAGTACGTGTTCTCGGAT (SEQ ID NO:6); Pan 3, CTGTTCTGGCGTTTCGCAGC (SEQ ID NO:7)) are shown and the cleavage site is indicated by a dotted line. Texts indicate insertion or deletion events.

FIG. 18I shows analysis of mtDNA SNVs of NSG mouse oocytes based on functional annotation. FIG. 18J shows analysis of mtDNA SNVs of NSG mouse oocytes based on base change. The majority of base changes are T>C (A>G) and G>A (C>T).

FIG. 19A shows the frequency of base substitutions on the heavy (H) and light (L) strands showing the strand asymmetry of low frequency mtDNA SNVs (VAF<0.01) in hOOs and 293T cell line (sequenced by Nanopore). FIG. 19B shows highly consistent mtDNA mutational spectrum in hOOs and 293T cell line. The left panel is for all SNVs, while the right one is for SNVs with VAF<0.01. FIG. 19C shows functional annotation of SNVs in protein-coding regions detected by iMiGseq of hOOs and the 293T cell line (sequenced by Nanopore). The size of the pie chart is proportional to overall mutation frequency, and the color corresponds to the type of mutation. Variants called in all UMI groups (not limited to extensive-coverage groups) were used to generate this plot. All hOOs show a similar enrichment of SNVs in COX1, ND1 and ND2 genes. The 293T cell line has more SNVs in the CYTB, ND4 and ND5 genes. FIG. 19D is box plots showing the distribution of dN/dS ratio of individual mtDNA in hOOs and 293T cells (sequenced by Nanopore). The mtDNA numbers of every sample are shown (red values). The red dots inside the boxes indicate the mean values of dN/dS, and the thick black lines represent the median values. Potential outlier values are marked by bold black dots, while individual values calculated from every UMI group are shown as small grey dots. The lower and upper boundaries of the box represent the 25th and 75th percentiles, respectively. The p values were based on the Kruskal-Wallis test, ****stands for p<2.22e-16. FIG. 19E shows circular plots showing the distribution of SNVs in the mitochondrial genome of B6_2 and B6_3 oocytes. The arrangement of the circular plots is similar to FIG. 17B. FIG. 19F, shows analysis of mtDNA SNVs of B6 mouse oocytes based on functional annotation. FIG. 19G shows analysis of mtDNA SNVs of B6 mouse oocytes based on base change. The majority of base changes are T>C (A>G) and G>A (C>T). FIG. 19H shows heatmaps of clustering of individual mtDNA detected in B6 mouse oocytes based on low frequency mtDNA SNVs (NHL<0.01). FIG. 19I shows mutational spectrum of all SNVs (left) and low frequency SNVs (NHL<0.01, right) detected in mouse oocytes. The oocytes show a similar pattern of mutational spectrum within the strain, while different strains are significantly different in mutational spectrum.

FIG. 20A shows distribution of NHL of mtDNA SNVs detected in the three hOOs. The SNVs fall in two groups, the low-frequency group of SNVs have NHLs below 1%, while the high-frequency ones have NHLs above 30%. FIG. 20B shows circular plots showing the distribution of SNVs in the mitochondrial genome of hOO_2 and hOO_3. The arrangement of the circular plots is similar to FIG. 18A. FIG. 20C shows Venn diagrams similar to those shown in FIGS. 3f & g, except that the variants are divided into two categories. The upper panels show SNVs with NHL<0.01, and the lower panels are for NHL≥0.01.

FIG. 21A shows VAF comparison of SNVs in the M7b mitochondrial haplogroup and hOO_1. All of the high frequency SNVs (Genbank frequency ≥60%) in the M7b haplogroup are presented as left-hand bars in each pair. The right-hand bars in each pair represent VAF calculations based on iMiGseq in single hOOs. FIG. 21B, similar to FIG. 21A except for M7c haplogroup and hOG_2. FIG. 21C, similar to FIG. 21A except for F1a haplogroup and hOG_3.

DETAILED DESCRIPTION OF THE INVENTION

I. Definitions

Figure 1A:
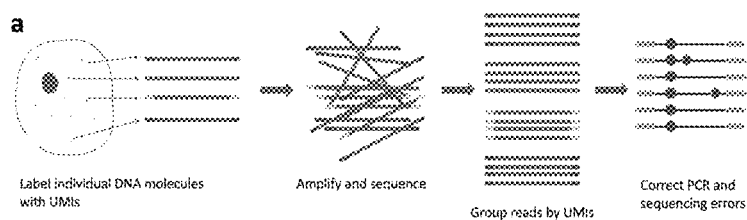
FIG. 1A is a schematic of using UMIs to label individual DNA molecule in a cell and illustrates how PCR errors are eliminated by grouping reads based on UMIs.

"Isolated," "isolating," "purified," "purifying," "enriched," and "enriching," when used with respect to nucleic acids of interest (e.g., DNA such as intact or fragmented genomic DNA, amplicons, etc.), indicate that the nucleic acids of interest at some point in time were separated, enriched, sorted, etc., from or with respect to other cellular material to yield a higher proportion of the nucleic acids of interest compared to the other cellular material, contaminates, or active agents such as enzymes, proteins, detergent, cations or anions. "Highly purified," "highly enriched," and "highly isolated," when used with respect to nucleic acids of interest, indicates that the nucleic acids of interest are at least about 70%, about 75%, about 80%, about 85%, about 90% or more, about 95%, about 99% or 99.9% or more purified or isolated from other cellular materials, contaminates, or active agents such as enzymes, proteins, detergent, cations or anions. "Substantially isolated," "substantially purified," and "substantially enriched," when used with respect to nucleic acids of interest, indicate that the nucleic acids of interest are at least about 70%, about 75%, or about 80%, more usually at least 85% or 90%, and sometimes at least 95% or more, for example, 95%, 96%, and up to 100% purified or isolated from other cellular materials, contaminates, or active agents such as enzymes, proteins, detergent, cations or anions.

As used herein, the term "amplicon" refers to product of amplification, for example, polymerase chain reaction (PCR). "Amplicons" can refer to a homogenous plurality of amplicons, for example a specific amplification product, or a heterogenous plurality of amplicons, for example a non-specific or semi-specific amplification product.

As used herein, the term "restriction endonuclease" or "restriction enzyme" or "RE enzyme" is any enzyme that recognizes one or more specific nucleotide target sequences within a DNA strand, to cut both strands of the DNA molecule at or near the target site.

As used herein, the term "nucleotide" and "nucleic acid" refers to a molecule that contains a base moiety, a sugar moiety and a phosphate moiety. Nucleotides can be linked together through their phosphate moieties and sugar moieties creating an inter-nucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate). There are many varieties of these types of molecules available in the art and available herein.

As used herein, the terms "oligonucleotide" or a "polynucleotide" are synthetic or isolated nucleic acid polymers including a plurality of nucleotide subunits.

With respect to the disclosed polynucleotide sequences, "N" can be any nucleotide (e.g., A or G or C or T), "R" can be any purine (e.g., G or A), and Y can be any pyrimidine (e.g., C or T).

As used herein, the terms "complement", "complementary", and "complementarity" with reference to polynucleotides (i.e., a sequence of nucleotides such as an oligonucleotide or a target nucleic acid) refer to the Watson/Crick base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, the sequence "5'-A-G-T-3'" is complementary to the sequence "3'-T-C-A-5'". The second sequence can be referred to as the reverse complement of the first sequence, and the first sequence can be referred to as the reverse complement of the second sequence.

Certain bases not commonly found in naturally-occurring nucleic acids may be included in the nucleic acids described herein. These include, for example, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. A complement sequence can also be an RNA sequence complementary to the DNA sequence or its complement sequence, and can also be a cDNA.

As used herein, the term "substantially complementary" means that two sequences hybridize. In some embodiments, the hybridization occurs only under stringent hybridization conditions. The skilled artisan will understand that substantially complementary sequences can, but need not allow, hybridize along their entire length. In particular, substantially complementary sequences may comprise a contiguous sequence of bases that do not hybridize to a target sequence, positioned 3' or 5' to a contiguous sequence of bases that hybridize e.g., under stringent hybridization conditions to a target sequence.

As used herein, the term "hybridize" refers to a process where two substantially complementary or complementary nucleic acid strands anneal to each other under appropriately stringent conditions to form a duplex or heteroduplex through formation of hydrogen bonds between complementary base pairs.

As used herein, the term "primer" refers to an oligonucleotide, which is capable of acting as a point of initiation of nucleic acid sequence synthesis when placed under conditions in which synthesis of a primer extension product which is complementary to a target nucleic acid strand is induced, i.e., in the presence of different nucleotide triphosphates and a polymerase in an appropriate buffer ("buffer" includes pH, ionic strength, cofactors etc.) and at a suitable temperature. One or more of the nucleotides of the primer can be modified for instance by addition of a methyl group, a biotin or digoxigenin moiety, a fluorescent tag or by using radioactive nucleotides. A primer sequence need not reflect the exact sequence of the template. For example, a non-complementary nucleotide fragment may be attached to the 5' end of the primer, with the remainder of the primer sequence being substantially complementary or complementary to the strand. The term primer as used herein includes all forms of primers that may be synthesized including peptide nucleic acid primers, locked nucleic acid primers, phosphorothioate modified primers, labeled primers, and the like. The term "forward primer" as used herein means a primer that anneals to the anti-sense strand of double-stranded DNA (dsDNA). A "reverse primer" anneals to the sense-strand of dsDNA.

Primers are typically at least 10, 15, 18, or 30 nucleotides in length or up to about 100, 110, 125, or 200 nucleotides in length. In some embodiments, primers are between about 15 to about 60 nucleotides in length, and or between about 25 to about 40 nucleotides in length. In some embodiments, primers are 15 to 35 nucleotides in length. There is no standard length for optimal hybridization or polymerase chain reaction amplification. An optimal length for a particular primer application may be readily determined in the manner described in H. Erlich, PCR Technology, PRINCIPLES AND APPLICATION FOR DNA AMPLIFICATION, (1989).

As used herein, the term "primer pair" or "primer set" refers to a forward and reverse primer pair (i.e., a left and right primer pair) that can be used together to amplify a given region of a nucleic acid of interest.

As used herein, the term "polymorphism" means variations of a nucleotide sequence in a population. For example, polymorphism can be one or more base changes, an insertion, a repeat, or a deletion. Polymorphisms can be single nucleotide polymorphisms (SNP), or simple sequence repeat (SSR). SNPs are variations at a single nucleotide, e.g., when an adenine (A), thymine (T), cytosine (C) or guanine (G) is altered. Generally a variation must generally occur in at least 1% of the population to be considered a SNP.

As used herein, the terms "aligning" and "alignment" refer to the comparison of two or more nucleotide sequence based on the presence of short or long stretches of identical or similar nucleotides. Several methods for alignment of nucleotide sequences are known in the art, as will be further explained below.

As used herein, the term "subject" includes, but is not limited to, animals, plants, bacteria, viruses, parasites and any other organism or entity. The subject can be a plant. The subject can be an animal, such as a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. A cell can be in vitro. Alternatively, a cell can be in vivo and can be found in a subject. A "cell" can be a cell from any organism including, but not limited to, a bacterium.

II. Compositions and Methods for Nucleic Acid Sequence Analysis

Compositions and methods for the analysis of mutations e.g., in single cells are provided.

In some embodiments, the methods employ a single-cell individual Mitochondrial Genome sequencing (iMiGseq) methodology such as the exemplified in Example 7, or variation thereof as disclosed herein. The experiments in the Examples below show that this methodology allows for high-throughput base-resolution analysis of individual mtDNA in single cells, and excels in providing base-resolution haplotype-resolved quantitative characterization of diverse types of rare variants. Nanopore-based iMiGseq provided ultra-long reads (over 16.5 kb) covering the full length of mtDNA, which contained unique molecular identifiers (UMIs) that allowed ultra-sensitive variant detection, complete haplotyping, and enumeration of thousands of original mtDNA in human cell lines and single mouse and human oocytes.

The data provided in the Examples below are believed to represent the first demonstration of a high-throughput base-resolution analysis of individual full-length mtDNA in single cells. Taking advantages of molecular consensus sequencing (IDMseq) and a specially designed bioinformatics pipeline (VAULT), iMiGseq (e.g., as described in Example 7) greatly improved the sensitivity of heteroplasmy detection and showed that most unique mtDNA SNVs in cells are rare and well below the current 1% detection limit. The experiments showed the methodology to be several orders of magnitude more sensitive than conventional NGS, as applied, and provides haplotype-resolved quantitative analysis of variants, to sequence individual mtDNA within single oocytes.

These compositions and methods can be used to investigate potentially pathogenic mtDNA mutations in human oocytes that lie below the previous detection limit. They provided the first haplotype-resolved mitochondrial genomes from single human oocytes. They revealed the linkage of rare heteroplasmic mutations, allowed the study of the linkage between mtDNA mutations, and provided evidence of selection imposed on mtDNA variants during human germline transmission.

A. Primers for Labeling Target Nucleic Acid Sequences

Compositions and methods for labeling targeting nucleic acid sequences are provided. The methods typically rely on one or more cycles of PCR with one or more primers at least one of which is a unique molecular identifier (UMI) primer. As used herein, bind and hybridize are used interchangeably to refer to the desired interaction between a PCR primer and the nucleic acid it targets for amplification.

A unique molecular identifier (UMI) primer typically includes one or more of a universal primer sequence, a unique molecular identifier (UMI) sequence, and a first target nucleic acid binding sequence. The orientation of the primer elements can be, for example, 5' universal primer sequence, unique molecular identifier (UMI) sequence, first target nucleic acid binding sequence 3'. The universal primer sequence is one that serves as a binding site for a universal primer once the universal primer sequence(s) is incorporated onto the end or ends of a target nucleic acid (e.g., universal primer sequence labeled). The universal primer sequence(s), when flanking the target nucleic acid, allow for multiplexed amplification of numerous, and uniquely labeled (e.g., UMI sequence labeled) target nucleic acids using a single primer set in a single PCR reaction. The universal primer sequence can be any suitable length and sequence. In some embodiments, the universal primer sequence is designed so that the same, single universal primer can amplify target nucleic acid(s) flanked by universal primer sequences. Thus, the universal primer set may be only a single primer that works as both a forward and reverse primer.

In a preferred embodiment, a universal primer sequence includes the sequence CATCTTACGATTACGCCAACCAC (SEQ ID NO:1), or the reverse sequence thereof, the complementary sequence thereto, or the reverse complementary sequence thereof.

The UMI sequence provides a unique molecular identity to the target the nucleic acid once the UMI sequence is incorporated onto the target nucleic acid (e.g., UMI sequence labeled). UMI sequences are usually designed as a string of totally random nucleotides (such as NNNN or NNNNNNN), partially degenerate nucleotides (such as NNNRNYN or NNNNTGNNNN (SEQ ID NO:2)), or defined nucleotides (e.g., when template molecules are limited). The UMI will be sequenced together with the target nucleic acid sequence. After sequencing, the reads can optionally be sorted by UMI and grouped together (i.e., demultiplexing).

UMI sequences can be or include any NNNN, with variable length, or with any other base (A, T, G, C) inside. UMI sequences are not limited to the sequences utilized in the Examples below, i.e. NNNNTGNNNN (SEQ ID NO:2). UMI sequences can be of any length of nucleotides with any sequence, for example between about 5 nucleotides to about 100 nucleotides (e.g., "N's").

In an exemplary embodiment, the UMI sequence includes NNNNTGNNNN (SEQ ID NO:2), wherein "N" can be A, T, G, or C, or the reverse sequence thereof, the complementary sequence thereto, or the reverse complementary sequence thereof.

Typically, the first target nucleic acid binding sequence binds (hybridizes) at or near a first site in the target nucleic acid sequence of interest, for example a gene of interest. The target nucleic acid binding allows for specific labeling (e.g., universal primer labeling, UMI labeling, or the combination thereof) and/or amplification of the target nucleic acid.

In embodiments, the first target nucleic acid binding sequence binds to nuclear DNA or mitochondrial DNA (mtDNA).

In a particular embodiment, a UMI primer for binding mtDNA includes CATCTTACGATTACGCCAAC-CACTGNNNTGNNNCTCCCGAATCAA CCCTGACCC (SEQ ID NO:3).

A second primer typically includes a second target nucleic acid binding sequence that can bind to a second site in the target nucleic acid sequence of interest, for example a gene of interest. The second primer can be a second UMI primer.

The second target nucleic acid primer can optionally include the same or a different UMI sequence as the first primer, and can optionally include the same or a different universal primer sequences as the first primer. The orientation of the primer elements can be, for example, 5' universal primer sequence, unique molecular identifier (UMI) sequence, first target nucleic acid binding sequence 3'.

The first and second primers are designed to flank the target nucleic acid sequence and label one or both ends with the universal primer sequence(s), UMI sequence(s), or combination thereof. The first and second primers may also be used to amplify the target nucleic acid.

Each of the universal primer sequence(s), the UMI sequence(s), and the target nucleic acid binding sequence(s) can include any number/length of nucleotides having any sequence suitable to achieve its molecular identifier and/or priming function(s). For example, in some embodiments, one or more of the universal primer sequence, the UMI sequence, and the target nucleic acid binding sequence of each primer has between about 5 and about 100 nucleotides, respectively. In some embodiments, one or more of one or more of the universal primer sequence, the UMI sequence, and the target nucleic acid binding sequence of each primer has any specific integer number of nucleotides between 5 and 100 nucleotides, inclusive, or range between two integers there between, respectively.

Any of the disclosed primers, including first and second UMI primers, first and second universal primers, or any combination thereof, can include any number/length of nucleotides having any sequence suitable to achieve its molecular identifier and/or priming function(s). For example, in some embodiments, one or more of UMI and/or universal primers have between about 5 and about 100 or about 500 nucleotides. In some embodiments, one or more of the UMI and/or universal primers have any specific integer number of nucleotides between 5 and 500 nucleotides, inclusive, or range between two integers there between.

In some embodiments, a plurality of sets of first and optionally second UMI primers are used for multiplexing. The nucleic acid binding sequences of each UMI primer set are designed to label the first and optionally second end of a target nucleic acid. The UMI sequence of each primer set can have the same UMI sequence so that different target nucleic acids can be distinguished, but individual molecules of each target nucleic acid cannot necessarily be distinguished by UMI sequence alone. In this way, sequences having the same UMI sequence can be clustered and consensus sequence for each target nucleic acid determined.

Alternatively, the UMI sequence within primers of the primer set can be different UMI sequences so that different target nucleic acids can be distinguished, and individual molecules of each target nucleic acid can also be distinguished by UMI sequence.

The UMI primers may further include a sample bar code. The sample bar code is unique to each sample, but not each target nucleic acid. The sample bar code can follow the same general guidelines provided herein for designing UMI sequences.

Preferably, the universal primer sequence, UMI sequence, target nucleic acid sequence, and sample bar code can be distinguished.

B. Methods of Labeling a Target Nucleic Acid

Methods of labeling a target nucleic acid are provided. Typically, the first primer alone or in combination with the second primer can be used during one or more PCR cycles to amplify a fragment of the nucleic acid sample that includes or consists of the target nucleic acid sequence or a fragment thereof. The nucleic acid sample serves as the initial template for this PCR. The amplified fragment can be referred to as an amplicon.

A given population of cells may contain different alleles of a target locus, which accounts for a small proportion of the pool of genomic DNA. A first step of targeted molecular consensus sequencing is labeling of the variant alleles with UMI. Ligation-based and PCR-directed UMI labeling are two widely used methods. However, ligation-based UMI labeling will label irrelevant regions and the low efficiency of ligation will also omit a proportion of target alleles (see, e.g., FIG. 8). PCR-directed UMI labeling is highly efficient but will result in UMI clashes (one original molecule labeled with multiple UMIs, leading to false UMI groups). The disclosed methods can be used to achieve high labeling efficiency and can faithfully retain the allele information (variants and frequency). After UMI labeling, the DNA with UMIs are amplified for sequencing in appropriated platforms (Illumina, Nanopore or PacBio, etc.).

Thus, the methods typically include carrying out at least one cycle of polymerase chain reaction using a first UMI primer, such as those introduced above, on a nucleic acid sample including a nucleic acid sequence to which the first target nucleic acid binding sequence of the first UMI primer can bind.

In some embodiments, the methods include carrying out at least one cycle of polymerase chain reaction using a plurality of different first UMI primers, such as those introduced above, on a nucleic acid sample including nucleic acid sequences to which a plurality of first target nucleic acid binding sequences of the first UMI primers can bind (e.g., a multiplex reaction that labels a first end of two or more target nucleic acids depending on the number of first UMI primers used).

In some embodiments, the UMI sequence for each first UMI primer includes one UMI sequence matched to one target nucleic acid binding sequence, thus each individual molecule of the target nucleic acid is labeled with the same UMI sequence, but each different nucleic acid target is labeled with a different UMI. In this way, different nucleic acid targets can be distinguished, but not necessarily different individual molecules (e.g., the same target in two different genomes) based on UMI alone.

In some embodiments, the UMI sequence for each first UMI primer includes different or unique UMI sequences matched to one target nucleic acid binding sequence, thus each individual molecule of the target nucleic acid is labeled with the a different UMI sequence, and each different nucleic acid target is labeled with a different UMI. In this way, different nucleic acid targets can be distinguished, and different individual molecules can also be distinguished based on UMI alone.

In some embodiments, the at least one cycle of polymerase chain reaction cycle of PCR further includes a second primer, as introduced above, including a second target nucleic acid binding sequence and the target nucleic acid includes a nucleic acid sequence to which the second target nucleic acid binding sequence of the second primer can bind. In some embodiments, the first cycle of PCR does not include a second primer.

In some embodiments, a second and optionally one or more subsequent cycles of PCR includes a second primer and optionally the first primer. Thus, in some embodiments, the first cycle is carried with the first primer alone or both the first and a second primer; and the second and/or subsequent cycles are carried out with a second primer alone, or with both the first and second primers. In some embodiments, all cycles of PCR are carried out with both a first and a second primer. Thus, in some embodiments, the first, second, and subsequent PCR cycles are all the same. In some embodiments, the first and second PCR cycles are different.

As introduced above, the second primer can further include the same or a different universal primer sequence as the first primer, or the reverse sequence thereof, the complementary sequence thereto, or the reverse complementary sequence thereof. The second primer can further include the same or different UMI as the first primer, or the reverse sequence thereof, the complementary sequence thereto, or the reverse complementary sequence thereof. In some embodiments, the second primer does not include a universal primer sequence, and/or does not include a UMI. In some embodiments, the second primer consists only of a second target nucleic acid binding sequence.

In some embodiments, the methods include carrying out at least one cycle of polymerase chain reaction (the second total cycle) using a plurality of second UMI primers, such as those introduced above, on a nucleic acid sample including nucleic acid sequences to which a plurality of second target nucleic acid binding sequences of the second UMI primers can bind (e.g., a multiplex reaction that labels a second end of two or more target nucleic acids depending on the number of second UMI primers used).

In some embodiments, the UMI sequence for each second UMI primer includes one UMI sequence matched to one target nucleic acid binding sequence, thus each individual molecule of the target nucleic acid is labeled with the same UMI sequence, but each different nucleic acid target is labeled with a different UMI. In this way, different nucleic acid target can be distinguished, but not necessarily different individual molecules (e.g., the same target in two different genomes) based on UMI alone. The UMI sequence of the second UMI primer can be the same or different from the UMI sequence of the first UMI primer.

In some embodiments, the UMI sequence for each second UMI primer includes different or unique UMI sequences matched to one target nucleic acid binding sequence, thus each individual molecule of the target nucleic acid is labeled with the a different UMI sequence, and each different nucleic acid target is labeled with a different UMI. In this way, different nucleic acid targets can be distinguished, and different individual molecules can also be distinguished based on UMI alone. The UMI sequence of the second UMI primer can be the same or different from the UMI sequence of the first UMI primer.

The first and second target nucleic acid binding sequences of the primer sets are designed to flank the target nucleic acid region so that it can be amplified using subsequent rounds of amplicon amplification, preferably using universal primers.

The method can include zero, or any integer number of second and subsequent PCR cycles, for example between 1 and 100 inclusive subsequent cycles of PCR.

Thus in some embodiments, the synthetic DNA also referred to as amplicons generated by the first and/or the second or subsequent PCR cycles includes one or both ends labeled with one or more of a universal primer sequence, a UMI, or the combination thereof.

In particular embodiments, the nucleic acid sample is amplified by two rounds of one-cycle PCR with respective (e.g., first and second) UMI-containing primers. After that, two universal primers are used to amplify the labeled amplicons.

As introduced above, one or more first primers alone or in combination with one or more second primers can be used separately or together to amplify two or more different target sequence amplicons. In some embodiments, different amplicons generated during separate PCR reactions are combined prior to amplicon amplification and/or sequencing.

In preferred embodiments, subsequent to one or more cycles of PCR using the UMI primer(s), a new one or more cycles of PCR are carried out using primer(s) that bind to the universal primer sequence and further amplify the amplicons. Typically, the template for this PCR is or includes the amplicons that include one or more UMI sequences and one or more universal primer sequences. Preferably, the amplicon has both ends labeled with the same or different universal primer sequences. In some embodiments, two or more different amplicons containing different nucleic acid target sequences contain the same universal primer sequence and different UMI sequences and can be amplified together using the same universal primers.

In some embodiments, the UMI primers are designed so that the first and second (e.g., forward and reverse) universal primers have the same sequence.

In some embodiments, such as when only one end of the target nucleic acid is label, the amplicon amplification can be carried out with one universal primer, and one random or target nucleic acid specific primer.

Any integer number of amplicon amplification PCR cycles can be carried out, for example, between 1 and 100 inclusive cycles of PCR including primers that bind to the one or more universal primer sequences. The number of cycles can depend on the abundance of the target sequence. In some embodiments, the disclosed methods include one or more steps of any of FIGS. 1A, 1B, 1C, 3C 4A, 4B, 4F, 8, 9A, 9B, 12A, and/or 16C.

The PCR step(s) typically includes an effective amount of the desired primer to accomplish the intended goal of adding a label and/or amplifying an amplicon.

In particularly preferred embodiments, the nucleic acid sample is amplified by two rounds of one-cycle PCR with respective (e.g., first and second) UMI-containing primers, or sets thereof. The first one-cycle PCR (e.g., extension of first primer) adds a universal primer sequence and UMI sequence to one end of a target nucleic acid. The second one-cycle PCR (e.g., extension of at least second primer, and optionally first primer) adds a universal primer sequence and UMI sequence to the other end of the target nucleic acid. As discussed herein, this first and second one-cycle PCRs may include a plurality of different first and second UMI primers (i.e., primer sets), respectively, that allow simultaneous (e.g. multiplex) labeling of a plurality of different target nucleic acids. Next, two universal primers can be used to amplify the labeled amplicons, which may include one target nucleic acid or a plurality of different target nucleic acids.

Figure 9A:
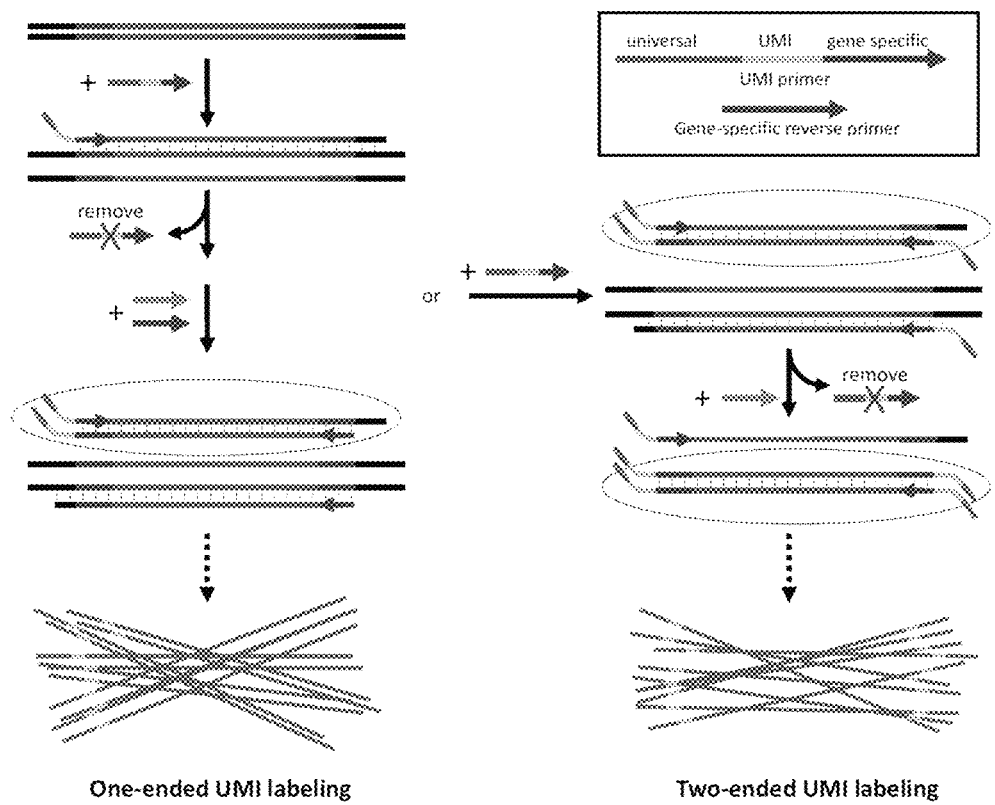
FIG. 9A is a schematic representation showing steps utilized for UMI labeling in some embodiments of the disclosed methods, and differences therein for one-end verse two-end UMI labeling. UMI primers are used to label individual DNA molecules with unique UMIs (one molecule is labeled with one UMI). It contains a 3' gene-specific sequence, a UMI sequence, and a 5' universal primer sequence. The 3' gene-specific sequence is selected for its high specificity to the target gene. The middle UMI sequence contains multiple random bases (denoted by Ns). The 5' universal primer sequence is used to uniformly amplify all UMI-tagged DNA molecules. Some of the disclosed embodiments including IDMseq are different from other UMI-based methods in that barcoding is achieved by a single round of primer extension rather than multiple cycles of PCR as commonly practiced (Kinde et al., *Proc Natl Acad Sci USA* 108, 9530-9535 (2011), Hiatt et al., *Nat Methods* 7, 119-122 (2010)). For two-ended labeling, an additional round of primer extension with reverse UMI primers will be done after removing forward UMI primers. The UMI-labeled DNA will be further amplified by universal primers before sequencing.

FIG. 9A is schematic representation of two particularly preferred embodiments of UMI labeling and target nucleic acid amplification: one-end UMI labeling (left side) and two-end UMI labeling (right side). As discussed herein, UMI primers are first used to label individual DNA molecules with unique UMIs (one molecule is labeled with one UMI). As depicted in FIG. 9A, in some embodiments, one-end UMI labeling includes or consists of one cycle of PCR with a UMI primer to UMI label one end of the target nucleic acid, followed by one or more cycles of PCR amplification using a universal primer in combination with a target nucleic acid specific primer. In some embodiments, two-end UMI labeling includes or consists of one cycle of PCR with a UMI primer to label one end of the target nucleic acid, followed by one cycle of PCR with e.g., a second UMI primer to label the other end of the target nucleic acid, followed by one or more cycles of PCR amplification using e.g., a universal primer.

Suitable UMI primers are described above and can contain, e.g., a 3' genes-specific sequence, a UMI sequence, and a 5' universal primer sequence. The 3' gene-specific sequence is selected for its high specificity to the target gene. The middle UMI sequence typically includes multiple random bases (denoted by Ns). The 5' universal primer sequence is used to uniformly amplify all UMI-tagged DNA molecules.

Preferred embodiments of the disclosed methods are different from other UMI-based methods in that barcoding can be achieved by a single round of primer extension rather than multiple cycles of PCR. For two-ended labeling, an additional round of primer extension with reverse UMI primers will be done after removing forward UMI primers. The UMI-labeled DNA will be further amplified by universal primers before sequencing.

Any of the methods disclosed herein can further include removal of one or more primers or other components of any previous step before moving to the next step. For example, in some embodiments, the UMI primer(s) is removed after a single cycle of PCR used to add it to the end of a target nucleic acid(s). Thus, in some embodiments, the method include one cycle of PCR with UMI primer(s) followed by removal of the UMI primer(s) prior to amplification of the amplicon with a set of universal and target nucleic acid specific primers (e.g., one-end label methods). In some embodiments, the method include one cycle of PCR with UMI primer(s) followed by removal of the UMI primer(s), followed by prior to one cycle of PCR with reverse UMI primer(s) followed by removal of the UMI primer(s), followed by amplification of the amplicon with a universal primer.

Figure 5:
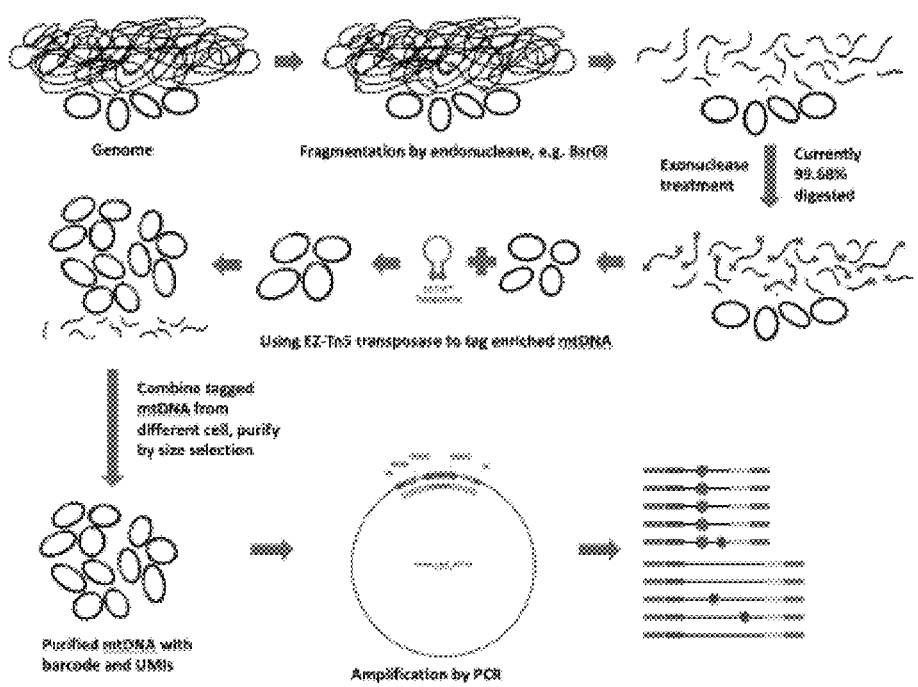
FIG. 5 is a schematic using EZ-Tn5 transposase to label individual mtDNA.
Figure 6:
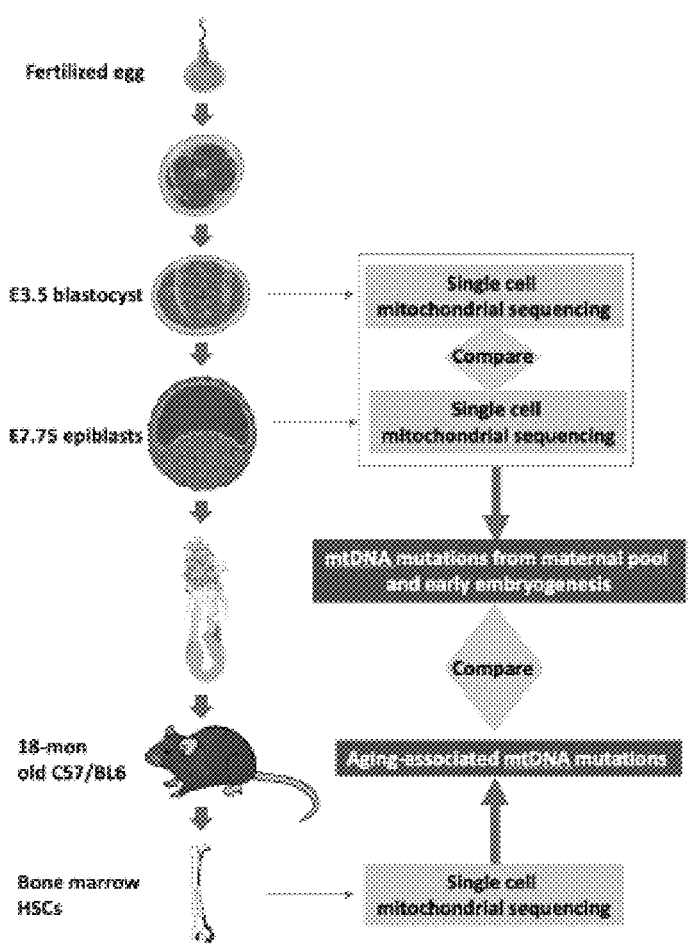
FIG. 6 is a flow chart showing an experimental design for analyzing mtDNA mutations during development and aging.

An alternative labeling method that is particularly effective for labeling mtDNA includes one or more of the steps of FIG. 5. For example, a method of labeling mtDNA can including
(i) optional restriction enzyme (e.g., BsrG1) digest of only the nuclear DNA in a nucleic acid sample including nuclear and mitochondrial DNA;
(ii) optionally, additionally, or alternatively treatment of the nucleic acid sample with lambda exonuclease; and
(iii) labeling of the remaining mtDNA with UMI labels, priming sites, and bar codes using EZ-Tn5 transposon.

The method can further include optional amplification of the labeled mtDNA sequence(s) as introduced above, and sequence of the labeled and optionally amplified amplicons as discussed below.

In this method, the restriction enzyme (e.g., BsrG1) is used to digest only the nuclear DNA to short fragments. The digested DNA can be further treated by lambda exonuclease. The circular mtDNA will be protected from two-round digestion. This will enrich mtDNA for being labeled by EZ-Tn5 transposon. After that, UMIs labeled mtDNA can be further enriched and purified by size-selection based method, e.g. Bluepippin or gel extraction. The mtDNA after transposition contains UMIs, priming sites, and barcodes. The primers integrated into the mitochondrial genome permit amplifying only mtDNA. The barcode sequences permit multiplexing samples before final amplification. By pooling samples together, PCR can be carried out with a higher amount of starting material (template), which will improve the PCR performance.

If the transposase-directed method is still not sensitive enough, mtDNA can be first amplified from a single cell. This gives rise to an indiscriminative magnification of all mtDNA in the cell. After that either PCR-directed or transposase-directed method can be used to label mtDNA with UMIs.

C. Methods of Sequencing and Sequence Analysis

The foregoing methods can be tethered to a larger method that includes sequencing. For example, a method of determining the sequence of a target nucleic acid can include:
  (i) labeling of one or more target nucleic acids according to a labeling method disclosed herein and optionally amplifying the amplicons;
  (ii) sequencing the labeled amplicons;
  (iii) optionally grouping sequences having the same UMI into one or more groups, preferably wherein each group consist of a sequence having the same UMI;
  (iv) determining the sequence of each target nucleic acid sequence by determining the consensus sequence of each group.

Some embodiments include identifying polymorphisms or other sequence variation in one or more of the target nucleic acids, for example compared to a control sequence or another nucleic acid sample.

In more specific embodiments, the polymorphism is a single nucleotide polymorphism (SNP).

In some embodiments, the sequencing step includes use of long-read sequencing technology, such as for example, using a Nanopore sequencing (e.g., Nanopore MinION) or PacBio Sequel. Oxford Nanopore sequencing is an emerging third-generation sequencing technology, that can generate ultra-long reads exceeding 800 kb (Jain et al., *Nat Biotechnol* 36, 338-345, doi:10.1038/nbt.4060 (2018)) in a portable device called MinION. These long-reads come without much compromise on reads consensus accuracy since the sequencing errors are mostly random (Loman et al., *Nat Methods* 12, 733-U751, doi:10.1038/Nmeth.3444 (2015)). They hold great promise in calling and phasing variants, assembling scaffold, and prospectively detecting epigenetic marks (Cretu et al., *Nat Commun* 8, 1326, doi:10.1038/s41467-017-01343-4 (2017), Simpson et al., *Nat Methods* 14, 407-410, doi:10.1038/nmeth.4184 (2017)).

PacBio describes its platform as single molecule real time sequencing (SMRT), based on the properties of zero-mode waveguides.

In particular embodiments, the methods include preparing a sequencing library, for example a Nanopore sequencing library such as a 1D ligation library from the labeled amplicons.

Any of the steps can include bioinformatics tools or techniques, and can include bioinformatics analysis. Exemplary preferred analysis include, but are not limited to, basecalling, sequence alignment(s), polymorphism identification and combinations thereof. An exemplary bioinformatics analysis can include, for example, any of the steps in FIG. 3C.

The sequencing error of Nanopore comes mainly from the algorithm used to interpret raw signals, which is the basecalling process. Signal-level algorithm for analyzing variations is not relied on the basecalled reads, but works directly on the raw electronic signal. Results indicate that cwDTW, an algorithm developed for the end-to-end mapping between the raw electrical current signal sequence and the reference genome, can accurately and effectively handle the ultra-long signal sequences of Nanopore sequencing (Han et al., *Bioinformatics* 34, 722-731, doi:10.1093/bioinformatics/bty555 (2018)). This algorithm can be modified to group reads and detect mutations after single-cell individual mtDNA sequencing. The established SNPs calling pipeline as shown in the Examples (e.g., FIG. 3C) can serve as a benchmark to evaluate the performance of new algorithms.

Figure 9B:
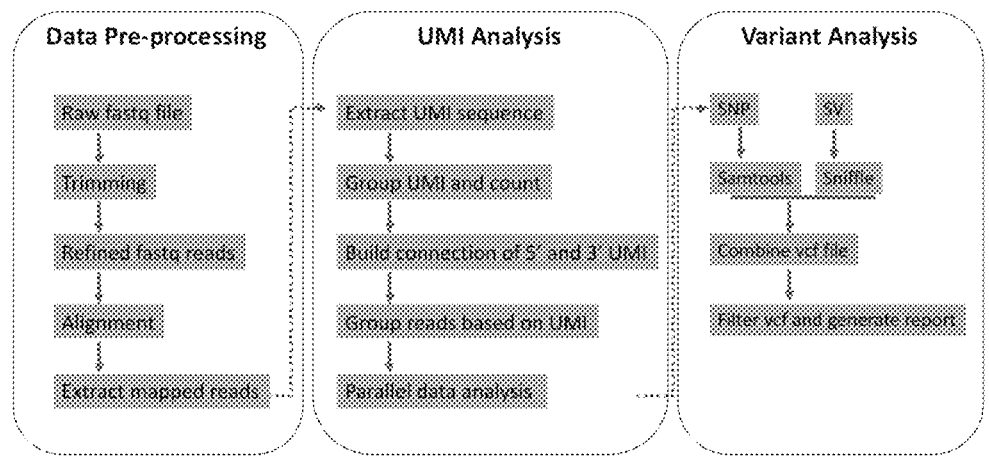
FIG. 9B is a flowchart showing an exemplary pipeline for data analysis. This embodiment is also referred to herein and in Example 5 as VAULT analysis. During data per-processing, raw reads were filtered and mappable reads were extracted. After that, VAULT applies a BLAST-like strategy to locate UMI sequence in reads by searching for the known sequences of the universal primer and gene-specific forward primer. After that, VAULT bins reads 5 according to UMI. The last steps of VAULT are variant calling for both SNVs and large SVs and report generation.

The algorithm typically needs to identify reads with the same UMI and use these to get the consensus sequence of the allele. In some embodiments, this step is done with read-clustering algorithms that work well for fixed-length reads of short-read sequencing (e.g. Illumina). However, this strategy could miss reads with complex changes such as those uncovered by long-read sequencing, which prevents detection of deletions, insertions and complex structural variants. In some embodiments, the data analysis includes a BLAST-like strategy to locate UMI sequence in reads regardless of length and structure. This type of analysis thus preserves the sequence information of all types of alleles and their frequency. An exemplary pipeline is illustrated in FIG. 9B. An algorithm referred to here VAULT carries out this pipeline.

VAULT uses several published algorithms for UMI extraction, alignment, and variant calling. The whole analysis can be done with one command. In brief, Nanopore reads are trimmed to remove adapter sequences, and then aligned to the reference gene for extraction of mappable reads. VAULT extracts UMI sequence, followed by counting of the occurrence of each UMI, which reflects the number of reads in each UMI group. If a structured UMI (e.g., NNNNTGNNNN (SEQ ID NO:2)) is used in the experiment, the program will also check the UMI structure and separate them to perfect UMIs and wrong UMIs. Next, based on a user-defined threshold of minimum reads per UMI group, the program bins reads for eligible UMIs. The grouped reads will be subjected to alignment, followed by SNP and SV calling. After finishing all variant calling, a final data cleanup is performed to combine individual variant call files (VCF) together and filter the VCF. The number of reads in UMI groups and the corresponding UMI sequence will be written in the ID field of the VCF. Individual folders named after the UMI sequence will be saved to contain the alignment summaries and BAM files of every UMI group. VAULT supports both long-read data and single-end/paired-end short-read data. The data analysis pipeline employs parallel computing for each UMI group, which avoids crosstalk during data analysis and accelerates the process. A typical analysis of 2.5 million long reads will take around four hours on a 32-core workstation. Any of the disclosed methods can include a data analysis step(s) including any one of more steps carried out by VAULT. In some embodiments, the methods include all of the steps carried out by VAULT.

D. Nucleic Acid Samples

The nucleic acid sample can be, for example, nuclear genomic DNA, mitochondrial genomic DNA, or a combination thereof. In a particular embodiment, the nucleic acid sample is maternal mitochondrial genomic DNA. The sample can be prokaryotic or eukaryotic cells. The cells can be, for example microbial (e.g., bacterial, viral, etc.), or from a higher organism, for example, an animal such as mammal including humans.

The source of the nucleic acid sample can from, for example, any integer between 1 and 1,000,000 cells inclusive, or any range formed of two integers there between, for example, between 1 and 10,000, 1 and 1,000, 1 and 100, 1 and 10, or 1 single cell.

The source of the nucleic acid sample can one single nuclei or one single mitochondrion.

In a particular embodiment, the nucleic acid sample is a mitochondrial DNA from one or more oocytes, e.g., human oocytes.

In some embodiments, any of the disclosed methods further include isolating the nucleic acid sample from, for example, a cell or cells. The isolation can include releasing the target nucleic acid sample by, for example, lysing the cell(s). The lysing can be chemical, enzymatic, osmotic, mechanical, or a combination thereof.

In some embodiments, the target nucleic acid is, or is suspected of, being related to aging or an age-related disorder.

Any of the methods can include one or more restriction digestions of the nucleic acid sample prior to the first cycle of PCR.

Any of the methods can include removing contaminants (e.g., one or more of primers, dNTPs, RNA, etc.), before the first cycle of PCR, after the first cycle of PCR, or any second or subsequent cycle of PCR, or any combination thereof.

Any of the disclosed methods can further include amplifying the nucleic acid sample, or a fraction thereof, prior to labeling.

Any of the disclosed methods can further include one or more rounds of enrichment and/or purification of the nucleic acid sample, target nucleic acid, amplicons, or otherwise labeled nucleic acid. The enrichment and/or purification can include size selection.

III. Exemplary Embodiments

Figure 1B:
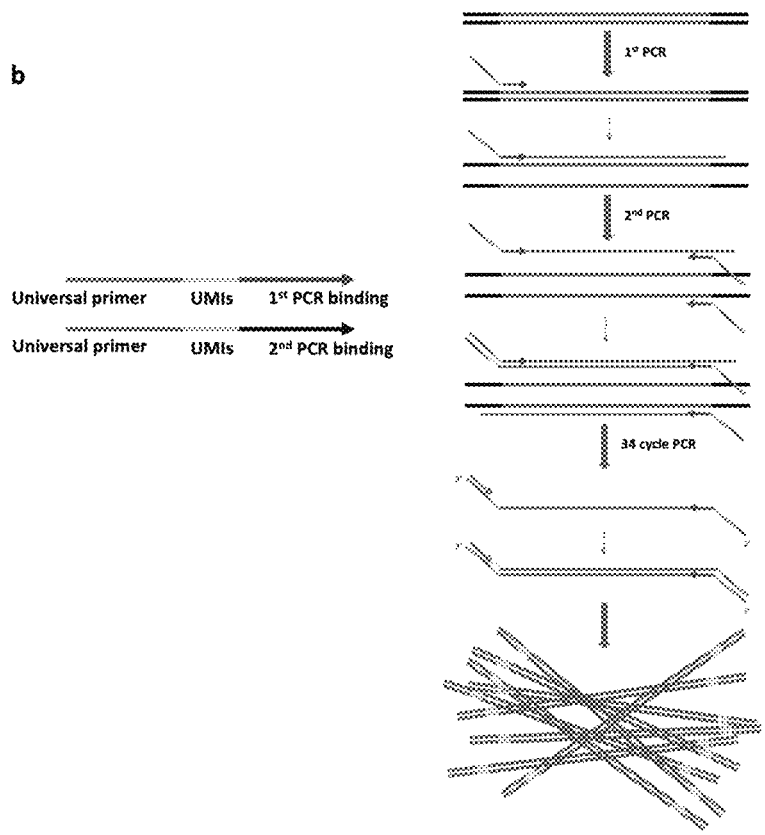
FIG. 1B is a schematic of PCR-directed single DNA labeling with two-end UMIs.

In a proof-of-concept study discussed in more detail below, total DNA was extracted from cells. For samples of limited quantity, cells were resuspended in PBS and lysed in RIPA buffer on ice to release DNA, followed by DNA cleanup with 1×AMPure XP beads. The purified DNA was subjected to PCR-directed labeling using the UMI primers (FIG. 1B).

The UMI primer contained three parts: a universal primer for amplifying the DNA, an UMI structure for labeling individual DNA molecule, and a gene-specific primer for targeted DNA amplification. An exemplary universal sequence is CATCTTACGATTACGCCAACCAC (SEQ ID NO:1). This sequence is designed to avoid forming secondary structure and nonspecific amplification of the human and the mouse genome.

Exemplary UMI sequences are NNNNTGNNNN (SEQ ID NO:2) and NNNNNTGNNNNN (SEQ ID NO:24), wherein "N" is any nucleotide (e.g., A, G, T, or C). This sequences is designed to avoid homopolymers.

The gene-specific primers can be any sequences to amplify a gene of interest using PCR.

This strategy can be used to label one or both ends of a gene of interest. An exemplary method for labeling one end of a gene of interest includes using one universal/UMI primer to label one end of the gene of interest according to the following PCR parameters: 98° C. 1 min, 70° C. 5 s, 69° C. 5 s, 68° C. 5 s, 67° C. 5 s, 66° C. 5 s, 65° C. 5 s, 72° C. 5 min (depends on the amplicon length and the polymerase), 4° C. hold.

After that, another universal/UMI primer is optionally used to label the other end of the amplicon, using the same or similar PCR parameters. In some embodiments, resulting amplicon can have a random combination of two different UMI.

The labeled DNA can be purified. In an exemplary protocol, the DNA is purified using 0.8×AMPure XP beads to remove the primers.

Next, the universal primer can be used to amplify all of the labeled DNA for sequencing.

This method can be used to label both linear DNA and circular DNA with UMIs.

Next, the amplified DNA (e.g., the amplicon(s)) is sequenced.

Any sequencing platform can be used and selected based on the application. For example, if the amplicon is long, then a long-read sequencing technology such as Oxford Nanopore, Pacific Biosciences can be used to generate reads spanning the whole amplicon with two UMIs.

An exemplary pipeline is described in more detail in the working Examples and Figures associated therewith. The example is illustrated using mitochondrial DNA, but it will be appreciated that any nucleic acid (e.g., a source of DNA, genomic or otherwise), can serve as the source material and can be substituted for mitochondrial DNA in the experiment.

Figure 4A:
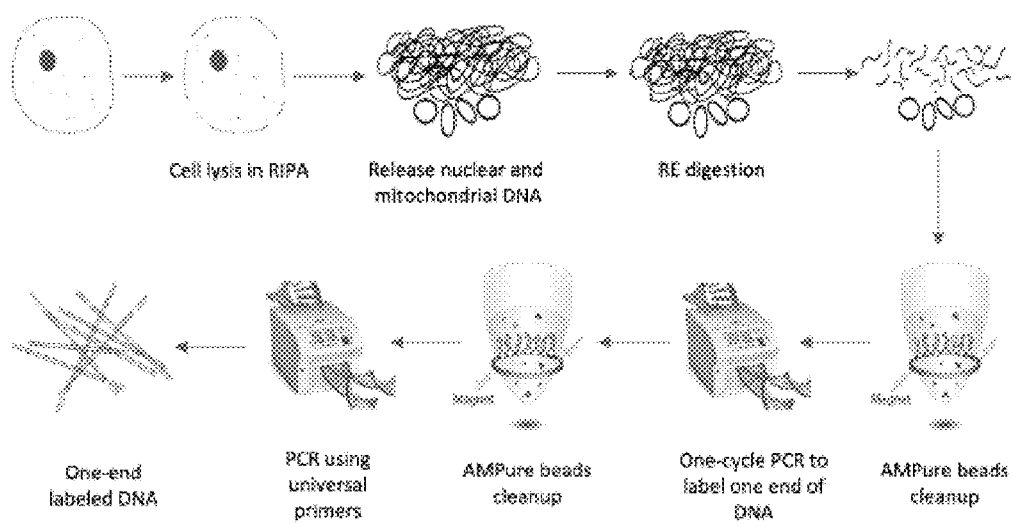
Figure 4B:
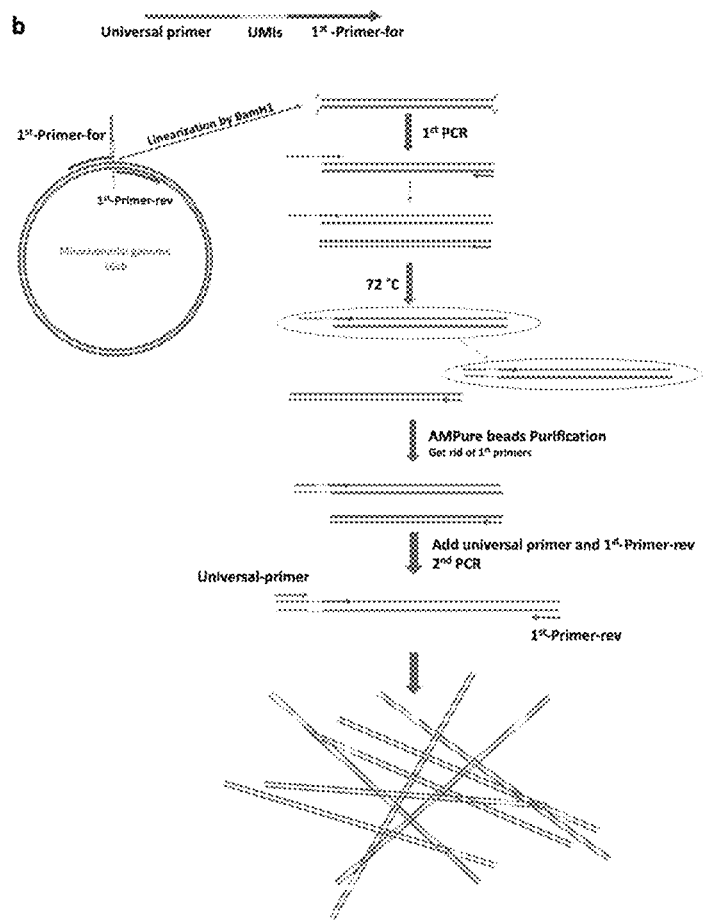

An exemplary pipeline is depicted in FIG. 4A-4B and illustrates labeling mitochondrial DNA in humans for single-cell mitochondrial sequencing. A single cell is sorted by manual pipetting and resuspended in 0.5 µl PBS, followed by lysis in 10 µl RIPA buffer on ice for 15 mins. After cell lysis, the reaction is diluted with water and the DNA is digested by BamHI in 50 µl reaction. After that, 0.8× AMPure XP beads are used to clean up the DNA and elute the purified DNA in 10 µl water. The purified DNA is subjected to PCR-directed labeling using primer CATCTTACGATTACGCCAACCACTGNNNTGNNNCTCC CGAATCA ACCCTGACCC (SEQ ID NO:3) and CTATTGGTGCGGGGGCTTTGT (SEQ ID NO:4). The PCR reaction is 11 µl Platinum™ SuperFi™ PCR Master Mix, 1 µl primer mix (final concentration 0.5 µM each), and 10 µl purified DNA. The PCR parameters are 98° C. 1 min, 70° C. 5 s, 69° C. 5 s, 68° C. 5 s, 67° C. 5 s, 66° C. 5 s, 65° C. 5 s, 72° C. 10 min, 4° C. holds.

After UMI labeling, the whole DNA is amplified using the primers 5'CTATTGGTGCGGGGGCTT3' (SEQ ID NO:5) and 5'CTATTGGTGCGGGGGCTT3' (SEQ ID NO:5). The amplicon is further purified by 0.8×AMPure XP beads.

Data reported in the Examples below indicate that this protocol can succeed in labeling mitochondrial DNA in as few as 10 cells (FIG. 4C-4E).

These UMI-labeled DNA were used to prepare an Oxford Nanopore 1D ligation library to sequence on a Nanopore MinION sequencer. 3478 unique UMIs were recovered (FIG. 4F). These results show that this method can label small amounts of DNA for downstream analysis of rare genetic variants in human cells.

QIAEX II Gel Extraction Kit with a higher DNA recovery of 80% can be used to purify DNA to increase the yield of, for example, the amplicons. The purified high molecule weight DNA can be used to make, for example, a 1D library using the ligation sequencing kit, and be sequenced on, for example, the R9.4.1 flow cell. The new-released kit and flow cell provide an improved sequencing yield up to 10 GB per flow cell.

Another consideration is the percentage of reads with UMIs. From the sequencing result of one-end labeled mtDNA, it is believed that 41.17% of reads can be grouped by UMIs for calling variants. This estimation can be revised by additional sequencing runs. Samples can be multiplexed to achieve the maximum usage of the flow cell.

These compositions and methods and be used to improve the accuracy and sensitivity of next-generation and third-generation sequencing. They are compatible with most sequencing platforms in the market and therefore holds a great promise to improve the application of genetic testing in clinical diagnosis.

Figure 16A:
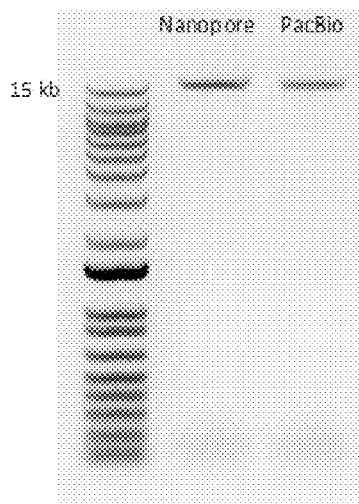
FIG. 16A is an Agarose gel picture showing full-length mtDNA amplified in iMiGseq of 293T cells.
Figure 16B:
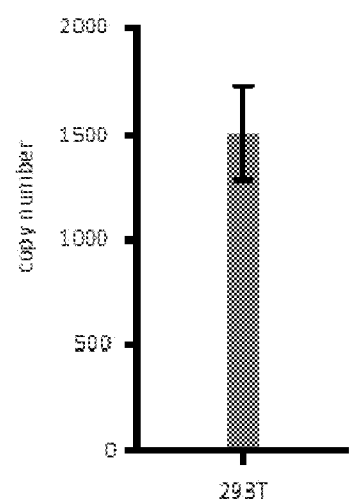
FIG. 16B shows qPCR quantitation of mtDNA copy number of 293T cells. The average mtDNA copy number is 1507 per cell.
Figure 16C:
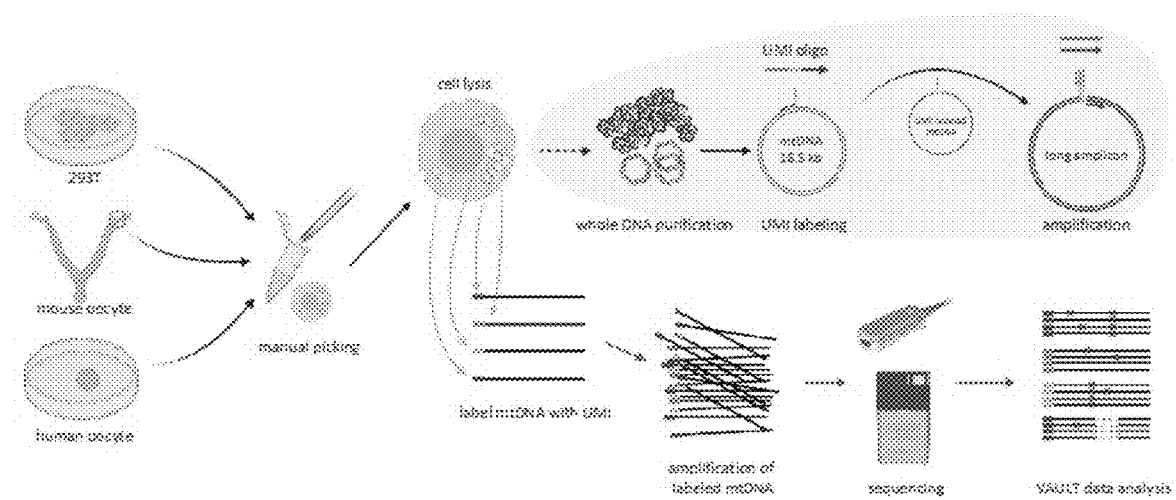
FIG. 16C is a schematic representation of iMiGseq. Single cells (5 cells for 293T) were manually picked and lysed in RIPA buffer. iMiGseq applies the IDMseq strategy to specifically label individual mtDNA with UMIs by single-oligo priming. The UMI oligo contains a 3' gene-specific sequence (red), a UMI sequence (yellow), and a 5' universal primer sequence (green). The UMI-labeled mtDNA is further amplified by long-range PCR using the universal primer (green) and gene-specific reverse primer (purple) as a single amplicon. The sequencing of long amplicons is performed on long-read Nanopore and PacBio sequencing platforms. The sequencing data is analyzed by a bioinformatic toolkit—VAULT—to identify UMI sequences, bin reads based on UMI and call variants.

Another exemplary pipeline is depicted in FIG. 16C, and thus the disclosed methods may include one or more of the steps therein, or otherwise discussed in Example 7, where the compositions and methods are used to determine and analyze the sequence of mitochondrial genomic DNA from a few as a single cell, e.g., an oocyte. Briefly, single cells can be picked and lysed in e.g., RIPA buffer. A disclosed nucleic acid labeling strategy can be used to specifically label individual mtDNA with UMIs by single-oligo priming. The UMI oligo contains a 3' gene-specific sequence, a UMI sequence, and a 5' universal primer sequence. The UMI-labeled mtDNA is further amplified by long-range PCR using the universal primer and gene-specific reverse primer as a single amplicon. See, e.g., Example 7 for exemplary primers, PCR cycles, etc.

The sequencing of long amplicons can be performed on long-read sequence platforms, e.g., Nanopore and PacBio sequencing platforms. The sequencing data can be analyzed by a bioinformatic toolkit, e.g., VAULT, to identify UMI sequences, bin reads based on UMI and call variants.

IV. Applications

The disclosed individual-nucleic acid molecule labeling can improve nuclear and mitochondrial genome analysis from a population of cells. It can provide the information of the individual nuclear allele in a population of cells, and the information of the comprehensive mitochondrial genome within one cell.

In some embodiments, UMI labeling is combined with Oxford Nanopore of PacBio sequencing technology. By combining the disclosed individual-DNA molecule labeling and long-read sequencing technology (e.g., Nanopore or PacBio), new insights into the roles of genomic alteration in aging processes are gained and can facilitate further study to improve health span and longevity.

In some embodiments, the compositions and methods are used for metagenomic analysis, e.g., analysis bacterial or viral genomes, analysis of hospital or environmental sample, e.g., for selective identification of antibiotic-resistant microbes.

Exemplary applications are discussed in more detail below.

A. Single Cell Analysis of Genomic Variation of Mitochondria

Single-mitochondrion sequencing has been achieved by isolating single mitochondrion in a single cell and subsequently amplifying it to three fragments (Morris et al., Cell Rep 21, 2706-2713, doi:10.1016/j.celrep.2017.11.031 (2017)), but sequencing only one of the thousands of mtDNA within one cell does not lead to a better interpretation of the causality of mtDNA mutation and related phenotype.

The disclosed compositions and methods can be used to label individual mitochondria in a single cell. High-throughput sequencing of the labeled mtDNA can be carried out using long-read e.g., Nanopore or PacBio sequencing. In addition, bioinformatics can be used for signal-level reads manipulation for accurately detecting mitochondrial mutations.

Thus, the compositions and methods can be used to facilitate the discovery of potentially pathogenic mtDNA mutations that lie below the current detection limit, study of the relationship between the levels of heteroplasmy and cellular phenotype, and contribute to a better understanding of mitochondrial mutations and aging.

The data below shows and individual-DNA labeling method using material from ten 293T cells. 293T cells are derived from a human embryonic kidney and qPCR data showed 293T cells have about 1000 copies of mtDNA.

In another embodiment, mtDNA is labeled in a single oocyte. Published data showed that mouse oocyte has an average 249.4 k mitochondria (Cree et al., Nat Genet 40, 249-254,doi:10.1038/ng.2007.63 (2008)), which is more than 100 times of that in the kidney (D'Erchia et al., Mitochondrion 20, 13-21, doi:10.1016/j.mito.2014.10.005 (2015)).

Because the disclosed methods, including iMiGseq as described in Example 7, permits quantitative base-resolution haplotype-resolved analysis of thousands of mtDNA in single cells, it offers an unprecedented opportunity for preimplantation genetic diagnosis (PGD) of mitochondrial diseases. Despite the prevalence (~1 in 5000) of mitochondrial diseases, current diagnostic procedures have been ineffective due to large genetic heterogeneity of mtDNA among different cells. The disclosed compositions and methods including, but not limited to, iMiGseq can be used to analyze mtDNA mutational load in single biopsied blastomeres, which have been shown by several studies [Monnot, et al., Hum Mutat. 2011 January; 32(1):116-25. doi: 10.1002/humu.21417 PMID: 21120938, Tajima, et al., J Assist Reprod Genet. 2007 June; 24(6):227-32 PMID: 17342424; Treff, et al., Fertil Steril. 2012 November; 98(5): 1236-40. doi: 10.1016/j.fertnstert.2012.07.1119. PMID: 22921075] to represent well the heteroplasmy level of in vitro fertilized embryos.

Besides the germline, the disclosed compositions and methods including, but limited to, iMiGseq, can be extended to somatic tissues to unravel the direction of causality between mtDNA mutations and aging and complex diseases. Similarly, because iMiGseq works for different species and cell types, it is believed to be widely applicable to many fields for the study this ancient organelle that energize most life forms on earth.

Thus, the disclosed compositions and methods can be used to determine if aging-associated mtDNA mutations originated from low-level heteroplasmic mutations during early embryo development or acquired during the adult life. To do so, the mtDNA mutational load is surveyed in a single cell isolated from early embryos and adult stem cells in aged subjects. In some embodiments, the materials is from humans or mice.

It has been shown that mtDNA copy number increases significantly when the replication suddenly accelerates on embryonic day 7.5 (E7.5) in mouse (Cree et al., Nat Genet 40, 249-254,doi:10.1038/ng.2007.63 (2008), Piko et al., Dev Biol 123, 364-374, doi:Doi 10.1016/0012-1606(87)90395-2 (1987)). Therefore, studying the mtDNA mutational load before and after this time allows survey of both the maternal mtDNA mutations and any potential new mutations due to replication error. Timed-pregnant C57BL/6 mice can be used for collecting single cells from E3.5 blastocyst and E7.75 epiblast (Okamura et al., *Genes Genet Syst* 90, 405-405 (2015)). Tissue can be dissociated into single cells and subjected to a single-cell individual-mtDNA labeling workflow. In an exemplary embodiment, 30 cells per stage can be sequenced in three biological replicates. The rest of the cells can be saved for repeats and validation experiments.

To produce mice with a strictly identical maternal mtDNA genetic background, embryos used in previous study can be implanted into pseudopregnant surrogate mothers. Live pups can be kept to, for example, 18 months for collecting aged tissues. A previous study reported that the mtDNA mutations cause a blockage during HSC differentiation (Norddahl et al., *Cell Stem Cell* 8, 499-510, doi:10.1016/j.stem.2011.03.009 (2011)).

Others have observed an increased level of mutations in the mtDNA control region in single HSCs in normal aged C57BL/6 mice using a PCR sequencing method (Yao et al., *Hum Mol Genet* 16, 286-294, doi:10.1093/hmg/ddl457 (2007)). However, it is unclear how the mutational load of mtDNA leads to HSC senescence. Applying single-cell individual-mtDNA sequencing to HSCs could help answer this question and also clarify the origin of aging-associated mutations. In an exemplary protocol, bone marrow cells (BMCs) can be flushed from the femur cavity by drilling holes at the tips of the femur with a 25 G needle. Red blood cells can be lysed using the ACK lysis buffer. After extensively washing, BMC will be labeled with antibodies against lineage markers, c-kit, Sca-1, mCD34 and mCD135 to FACS sorted for phenotypic HSCs (Lin-Sca-1+c-kit+ mCD34-mCD135-). HSCs can be used immediately or cryopreserved for later analysis. In particular embodiments, 30 cells per cell type are sequenced in three biological replicates. The rest of the cells can be saved for repeats and validation experiments.

By comparing the mtDNA mutation repertoire in stem cells of origin and developmental stage, the origin of mutations in aged tissues can be identified and the question how the accumulation of mtDNA mutations contribute to aging can be answered.

To validate the mutations detected, a different haplotype mtDNA from a phylogenetically distant mouse strain (NZB) can be spiked in the library to check the variant calling sensitivity and accuracy. Ultradeep Illumina sequencing and the digital droplet PCR can be used to identify the mutations.

Mitochondria are vital to life. Mutations in mtDNA can cause infertility, multi-systems diseases, stem cell dysfunction and aging. The mechanisms by which mtDNA mutations contribute to these conditions are not well understood, partly due to the limitations of current methods for the detection and quantification of mtDNA mutations. The disclosed compositions and methods can be utilized to improve the sensitivity and accuracy of mtDNA detection and increase the resolution of mtDNA mutational analysis to the single-cell level. The compositions and method allow researchers to address several key open questions in the field, including characterization of a full-range of pathogenic mtDNA mutations that lie below the current detection limit, mechanistic study of the roles of mtDNA mutation in stem cell function and aging, and provision of diagnostic tools for mitochondrial diseases. Other potential applications include sensitive detection of mtDNA mutations in minute samples for forensic testing and using mtDNA mutation signatures for lineage tracing in humans.

B. Decoding the Mutational Processes in Stem Cells

The disclosed compositions and methods can be used to study the development of somatic mutations in stem cells, e.g., hematopoietic stem cells (HSCs), and their influence on aging, by sequencing individual alleles from a population of the cells.

For example, the compositions and methods can be used to investigate HSC aging using the Fanconi anemia mouse model. Previous studies demonstrated that mice harboring the Fanca-/- deficiency give rise to a high level of DNA mutations along with a functional decline in HSCs (Walter et al., *Nature* 520, 549-552, doi:10.1038/nature14131 (2015), Kaschutnig et al., *Cell Cycle* 14, 2734-2742, doi:10.1080/15384101.2015.1068474 (2015), Parmar et al., *Mutation Research/Fundamental and Molecular Mechanisms of Mutagenesis* 668, 133-140, doi:10.1016/j.mrfmmm.2009.03.015 (2009)).

A putative mechanism for how deficiencies of Fanconi anemia repair pathway contribute to accelerated nuclear DNA mutations is described in (Walter et al., *Nature* 520, 549-552, doi:10.1038/nature14131 (2015)). In homeostatic conditions, HSCs reside in a quiescent state within the bone marrow niche. Stress-induced HSC activation initiates the DNA replication and upregulates energy production via oxidative phosphorylation within the mitochondria. This brings a high level of intracellular ROS, which increases the likelihood of the DNA replication fork colliding with repair intermediates, result in the induction of many stalled replication forks. The Fanconi anemia repair pathway can resolve the stalled replication fork by coordinating the regression of the replicative machinery followed by translesion synthesis and homologous recombination repair. This repair pathway is of high fidelity and prevents DNA mutations. However, for some lesions, the replication fork will collapse, resulting in a DNA double-strand break (DSB), which will in turn promote a locus-specific phosphorylation of cH2AX. Inefficient repair of DNA lesions will lead to cell death, or survive with the addition of DNA mutations. The deficiencies of Fanconi anemia repair pathway will favor error-prone repair of stress-induced DNA damage, leading to an accelerated accumulation of nuclear mutations.

The disclosed compositions and methods can be used to sequence and track the dynamic change and load of mutations in aging, e.g., HSC aging. Exemplary genes include, but are not limited to, those in Table 1:

TABLE 1

| List of genes to be sequenced. | |
| --- | --- |
| Gene type | Gene |
| DNA repair pathway | TP53, P21, XPB, XPD, TTDA |
| Involved in longevity | LMNA, WRN, CSA, CSB, TOR, S6K, IGF1, IIS |
| Frequently mutated in HSCs | DNMT3A, TET2, JAK2, ASXL1, SF3B1, SRSF2, RUNX1, NRAS, FLT3 |

These genes were chosen based on the following criteria: 1) genes involved in DNA repair pathway, 2) genes found to impact on longevity (Burtner & Kennedy, *Nat Rev Mol Cell Biol* 11, 567-578, doi:10.1038/nrm2944 (2010)), 3) genes frequently mutated in HSCs (Moehrle & Geiger, *Exp Hematol* 44, 895-901, doi:10.1016/j.exphem.2016.06.253 (2016), Smith & Sudbery, *Genome Res* 27, 491-499, doi:10.1101/gr.209601.116 (2017)) (Table 1).

Thus, the compositions and method disclosed herein can be used to investigate how somatic mutations accumulate in the earliest stage of stem cell aging, e.g., HSC aging, and the relationship between mutational load and stem cell, e.g., HSC, senescence. The result may unveil new ways of slowing the aging and extending the healthy lifespan.

The highly sensitive and accurate detection of rare mutations in a population of cells can be achieved by combining the individual-DNA molecule labeling method (FIG. 1C), the long-read Nanopore sequencing technology, and the signal-level data-analysis algorithm. The sensitivity of the method can be determined using an artificial "rare mutations" sample by pooling different haplotype of DNA together at a series of ratio, for example, gene edited cell lines with single nucleotide change and gene deletion.

Genomes from wild-type and gene edited cell lines can be extracted using QIAGEN DNeasy blood and tissue kits. Two genomes can be pooled at 1:1000, 1:10000, 1:100000, which equals to 0.1%, 0.01%, and 0.001% allele frequency, respectively. The individual-DNA molecule labeling method can be used to label individual alleles in the mixed genome. A 1D library can be prepared and sequenced on Nanopore MinION. Signal-level algorithm of data analysis can be used to group reads based on UMIs and call variants. In some embodiments, the sequence coverage is 200×per grouped reads. Ultra-deep Illumina sequencing of the same samples can be done as a reference.

The frequency of HSCs in bone marrow is about 0.01% of total nucleated cells and about 5000 can be isolated from an individual mouse depending on the age, sex, and strain of mice as well as purification scheme utilized (Challen et al., *Cytometry A* 75, 14-24, doi:10.1002/cyto.a.20674 (2009)). This means a sensitivity of 0.01% of allele frequency will be enough to detect one allele mutation in 5000 cells. It is believed to be difficult to detect rare mutations with less than 1% allele frequency use Illumina sequencing because of its intrinsic sequencing error (Shendure & Ji, *Nature Biotechnology* 26, 1135-1145, doi:10.1038/nbt1486 (2008)). The disclosed method is believed to be able to exceed this sensitivity. If the mutations can be called at 0.001% allele frequency, a smaller allele frequency of samples can be used to detect the sensitivity of this method.

Figure 7:
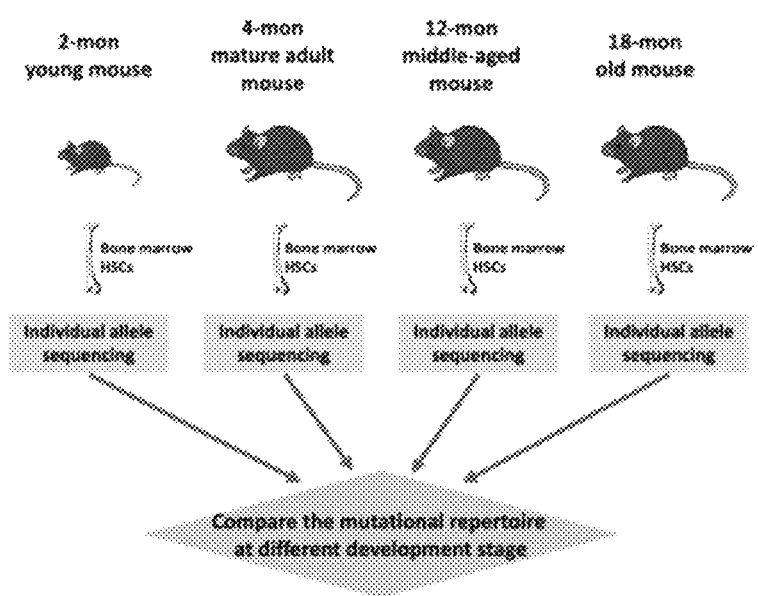
FIG. 7 is a schematic of an experimental design for analyzing the mutational processes in HSC aging in mouse.

The disclosed workflow can also be used to survey the mutational processes in HSC aging in mouse model of Fanca−/− deficiency (FIG. 7). Previous studies showed that Fanca−/− mouse appeared normal, without clear congenital malformations or growth retardation (Cheng et al., *Human Molecular Genetics* 9, 1805-1811, doi:DOI 10.1093/hmg/9.12.1805 (2000)), which make it possible to study the aspect of HSC aging. This mouse strain has a 5-fold higher level of DNA mutations in HSCs and a relatively normal number of progenitor bone marrow cells (Walter et al., *Nature* 520, 549-552, doi:10.1038/nature14131 (2015), Kaschutnig et al., *Cell Cycle* 14, 2734-2742, doi:10.1080/15384101.2015.1068474 (2015), Sperling et al., *Nat Rev Cancer* 17, 5-19, doi:10.1038/nrc.2016.112 (2017)). The impaired DNA damage (e.g. double-strand break) repair pathway by Fanca−/− deficiency gives rise to an accumulation of mutations, including single nucleotide variants, deletions, insertions, and translocations (Palovcak et al., *Cell Biosci* 7, 8, doi:10.1186/s13578-016-0134-2 (2017)). And the proportion of mutations could be very low in the whole HSCs population. The full spectrum of mutations, especially rare mutations and structural variants, is hard to be detected by short-reads Illumina sequencing.

Individual-DNA molecule labeling method together with long-range PCR (up to 16.5 kb) and long-reads Nanopore sequencing can solve this problem. The well-studied hematopoietic system allows for focus on several key genes with high mutational frequency (Moehrle & Geiger, *Exp Hematol* 44, 895-901, doi:10.1016/j.exphem.2016.06.253 (2016)).

Bone marrow cells (BMCs) can be flushed from the femur cavity by drilling holes at the tips of the femur with a 25 G needle. Red blood cells can be lysed using the ACK lysis buffer. After extensively washing, BMC can be labeled with antibodies against lineage markers, c-kit, Sca-1, mCD34 and mCD135 to FACS sorted for phenotypic HSCs (Lin-Sca-1+ c-kit+mCD34−mCD135−). HSCs can be either used immediately or cryopreserved for later analysis. In an exemplary embodiment as assay include sequence of the UMIs labeled amplicon of 22 genes in Table 1 using three mice per age (2 months, 4 months, 12 months, 18 months) in three biological replicates. 5000 HSCs can be isolated from each mouse and the cells lysed in RIPA buffer followed by DNA purification by AMPure beads. This DNA extraction method has been shown to work well in small numbers of cells in experiments described below (FIGS. 4A-4E). After that, the extracted DNA can be subjected to the workflow described herein to detect mutations in these genes. To validate detected mutations, the mutated DNA can be cloned into a plasmid and sequenced by Sanger sequencing. The digital droplet qPCR can be used to confirm the mutations. By comparing the mutation repertoire in HSCs at different developmental stage; 1) The patterns of mutational expansion in the early stage of HSCs senescence; 2) The unique mutational constitution and pattern at each stage of HSC aging; and 3) A more accurate mutational load in HSC aging, can be investigated.

It is well known that genomic instability contributes to aging. However, there is still a fundamental gap in understanding the very beginning stage of aging senescence which is how the cellular mutations get accumulated in cells. The disclosed compositions and methods can be used to address this question and lead to a better understanding of genomic mutations and HSC aging. Besides its impact on aging research, the technology can make possible DNA sequencing in allele-level sensitivity on various topics and applications (such as detection of minimal residual disease). Exemplary use such as those described herein can provide new insights into the roles of genomic alteration in aging processes and facilitate further study to improve healthspan and longevity.

Besides its influence on aging research, the disclosed compositions and methods can be used for range of other application. For example, DNA sequencing in allele-level sensitivity on various topics and applications: such as detection of minimal residual disease), single cell mitochondrial sequencing can be used for diagnosing mitochondria-related diseases, bacteria-specific gene sequencing to identify the bacterial strains, and ultra-sensitive detection of rare genetic variant in biological samples (e.g. forensic test).

The disclosed compositions and methods of use thereof can be further understood through the following numbered paragraphs.

1. A unique molecular identifier (UMI) primer comprising a universal primer sequence, a unique molecular identifier (UMI) sequence, and a first target nucleic acid binding sequence.
2. The primer of paragraph 1 wherein the orientation of the universal primer sequence, unique molecular identifier (UMI) sequence, and first target nucleic acid binding sequence is 5' universal primer sequence, unique molecular identifier (UMI) sequence, first target nucleic acid binding sequence 3'.
3. The primer of paragraphs 1 or 2 wherein the universal primer sequence comprises the sequence CATCTTAC-GATTACGCCAACCAC (SEQ ID NO:1), the reverse sequence thereof, the complementary sequence thereto, the reverse complementary sequence thereof.

4. The primer of any one of paragraphs 1-3, wherein the UMI sequence comprises a random sequence (such as NNNN or NNNNNNN), a partially degenerate nucleotide sequence (such as NNNRNYN or NNNNTGNNNN (SEQ ID NO:2), wherein "N" can be A, T, G, or C, "R" can be G or A, and "Y" can be T or C, or the reverse sequence thereof, the complementary sequence thereto, or the reverse complementary sequence thereof, optionally wherein the UMI sequence is between about 5 and about 100 nucleotides in length.

5. The primer of any one of paragraphs 1-4, wherein the first target nucleic acid binding sequence binds at or near or a gene of interest.

6. The primer of paragraph 5, wherein the first target nucleic acid binding sequence binds to mitochondrial DNA.

7. The primer of any one of paragraphs 1-6 comprising CATCTTACGATTACGCCAAC-CACTGNNNTGNNNCTCCCGAATCAA CCCTGACCC (SEQ ID NO:3)

8. A method of labeling a target nucleic acid comprising carrying out at least one cycle of polymerase chain reaction using a first primer of any of paragraphs 1-7 and a nucleic acid sample comprising a nucleic acid sequence to which the first target nucleic acid binding sequence of the primer can bind.

9. The method of paragraph 8 wherein the first cycle of PCR further comprises a second primer comprising a second target nucleic acid binding sequence and the target nucleic acid comprises a nucleic acid sequence to which the second target nucleic acid binding sequence of the second primer can bind.

10. The method of paragraphs 8 or 9, wherein a second and optionally one or more subsequent cycles of PCR further comprises a second primer alone or in combination with the first primer, the second primer comprising a second target nucleic acid binding sequence, and the target nucleic acid comprising a nucleic acid sequence to which the second target nucleic acid binding sequence of the second primer can bind.

11. The method of paragraphs 9 or 10, wherein the second primer further comprises the same or a different universal primer sequence as the first primer, or the reverse sequence thereof, the complementary sequence thereto, or the reverse complementary sequence thereof.

12. The method of any one of paragraphs 9-11, wherein the second primer further comprises the same or different UMI as the first primer, or the reverse sequence thereof, the complementary sequence thereto, or the reverse complementary sequence thereof.

13. The method of any one of paragraphs 9-12 wherein the orientation of the universal primer sequence, unique molecular identifier (UMI) sequence, and second target nucleic acid binding sequence of the second primer is 5' universal primer sequence, unique molecular identifier (UMI) sequence, second target nucleic acid binding sequence 3'.

14. The method of any one of paragraphs 9-13 comprising any integer between 1 and 100 inclusive subsequent cycles of PCR.

15. The method of any one of paragraphs 8-14, wherein the nucleic acid sample is nuclear genomic DNA, mitochondrial genomic DNA, or a combination thereof.

16. The method of any one of paragraphs 8-15, wherein the source of the nucleic acid sample is any integer between 1 and 1,000,000 cells inclusive, or any range formed of two integers there between, for example, between 1 and 10,000, 1 and 1,000, 1 and 100, 1 and 10, or 1 single cell.

17. The method of any one of paragraphs 8-16, wherein the source of the nucleic acid sample is one single nuclei or one single mitochondrion.

18. The method of any one of paragraphs 8-17, wherein the nucleic acid sample is isolated from a cell or cells.

19. The method of paragraph 18, wherein the isolation comprises releasing the target nucleic acid sample by lysing the cell(s).

20. The method of any one of paragraphs 8-19, wherein the nucleic acid sample is subjected to a restriction digestion prior to the first cycle of PCR.

21. The method of any one paragraphs 8-20 further comprising removing contaminants (e.g., one or more of primers, dNTPs, RNA, etc.), before the first cycle of PCR, after the first cycle of PCR, after the last cycle of PCR, or any combination thereof.

22. The method of any one of paragraphs 8-21 further comprising any integer between 1 and 100 inclusive cycles of PCR comprising primers that bind to the one or more universal primer sequences.

23. The method of any one of paragraphs 8-22 comprising two or more first and second primer sets, each first and second primer set comprising different target nucleic acid binding sequences designed to label and optionally amplify different target nucleic acids.

24. The method of paragraph 23, wherein the UMI sequence for each first primer of each primer set is the same.

25. The method of paragraph 23, wherein the UMI sequence for each first primer of each primer set is different.

26. The method of any one of paragraphs 23-25, wherein the UMI sequence for each second primer of each primer set is the same.

27. The method of any one of paragraphs 23-25, wherein the UMI sequence for each second primer of each primer set is different.

28. A method of determining the sequence of a target nucleic acid comprising
(i) labeling one or more target nucleic acids according to the method of any one of paragraphs 8-27;
(ii) sequencing the labeled amplicons;
(iii) optionally grouping sequences having the same UMI into one of more groups;
(iv) determining the sequence of each target nucleic acid sequence by determining the consensus sequence of each group.

29. The method of paragraph 28 further comprising (v) identifying polymorphisms in one or more of the target nucleic acids.

30. The method of paragraph 29, wherein the polymorphism is a single nucleotide polymorphism (SNP).

31. The method of any one of paragraphs 28-30, wherein the sequence comprises long-read sequencing technology.

32. The method of paragraph 31, wherein the long-read sequencing technology is comprises Nanopore MinION sequencer.

33. The method of paragraph 32, wherein the long-read sequencing technology comprises preparing a 1D ligation library from the labeled amplicons.

34. The method of any one of paragraphs 28-33, wherein any of steps (iii)-(v) are carried out using bioinformatics analysis.

35. The method of paragraph 34, wherein the bioinformatics analysis comprises basecalling, sequence alignment(s), polymorphism identification or a combination thereof.

36. The method of paragraphs 34 or 35, wherein the bioinformatics analysis comprises one or more of steps of FIG. 3C.

37. A method of labeling a target nucleic acid and optionally sequencing the labeled target nucleic comprising one or more of the steps of any of FIG. 1A, 1B, 1C, 3C 4A, 4B, 4F, or 5.

38. A method of labeling a target nucleic acid and optionally sequencing the labeled target nucleic comprising
    (i) restriction enzyme (e.g., BsrGI) digest of only the nuclear DNA in a nucleic acid sample comprising nuclear and mitochondrial DNA;
    (ii) treatment of the nucleic acid sample with lambda exonuclease;
    (iii) labeling of the remaining mtDNA with UMI labels, priming sites, and bar codes using EZ-Tn5 transposon;
    (iv) sequencing the labeled mtDNA.

39. The method or any one of paragraphs 8-38 further comprising amplifying the nucleic acid sample, or a fraction thereof, prior to labeling.

40. The method of any one of paragraphs 8-39 further comprising one or more rounds of enrichment and/or purification of the nucleic acid sample, target nucleic acid, amplicons, or otherwise labeled nucleic acid.

41. The method of paragraph 40, wherein the enrichment and/or purification comprises size selection.

42. The method of any one of paragraphs 8-41, wherein the target nucleic acid is, or is suspected of, being related to aging or an age-related disorder.

43. A method of one-end UMI labeling comprising a single round of extension of a UMI primer comprising a universal primer sequence, unique molecular identifier sequence, and target nucleic acid binding sequence that hybridizes to a target nucleic acid sequence and optionally removing the UMI primer from the reaction mixture.

44. A method of two-end UMI labeling comprising a single round of extension of a forward UMI primer comprising a universal primer sequence, unique molecular identifier sequence, and target nucleic acid binding sequence that hybridizes to a target nucleic acid sequence and optionally removing the forward UMI primer from the reaction mixture, and a single round of extension of a reverse UMI primer comprising a universal primer sequence, unique molecular identifier sequence, and target nucleic acid binding sequence that hybridizes to a target nucleic acid sequence and optionally removing the reverse UMI primer from the reaction mixture.

45. The method of paragraphs 43 or 44, further comprising amplifying the one-end or two-end labeled target nucleic acids by PCR with a universal primer alone or in combination with a target nucleic acid specific primer, wherein the cycles of PCR amplify the one- or two-end UMI labeled target nucleic acid.

46. A method of determining the sequence of a target nucleic acid comprising
    (i) labeling one or more target nucleic acids according to the method of any one of paragraphs 43-45;
    (ii) sequencing the labeled amplicons;
    (iii) optionally grouping sequences having the same UMI into one of more groups;
    (iv) determining the sequence of each target nucleic acid sequence by determining the consensus sequence of each group.

47. A method of labeling a target nucleic acid and optionally sequencing and optionally analyzing the labeled target nucleic comprising one or more of the steps of any of FIG. 8, 9A, 9B, 12A, or any combination thereof.

48. A method of labeling a target nucleic acid and optionally sequencing and optionally analyzing the labeled target nucleic comprising one or more of the steps of any of FIG. 16C, or any combination thereof.

49. The method of any one of paragraphs 1-48, wherein the target nucleic acid is mitochondrial DNA.

50. The method of paragraph 50, wherein the mitochondrial DNA is from one or more somatic or germline cells, optionally wherein the mitochondrial DNA is maternal, genomic mitochondrial DNA oocytes, optionally a single oocyte.

EXAMPLES

Bi, C. et al. Long-read individual-molecule sequencing reveals CRISPR-induced genetic heterogeneity in human ESCs. *Genome Biol,* 21, Article number: 213, 14 pages, doi:10.1186/s13059-020-02143-8 (2020), and the 18 pages of Supplemental/Additional materials associated therewith are specifically incorporated by reference herein it their entireties.

Example 1: Development of a Method for Labeling Individual DNA Molecules

Methods

Figure 1C:
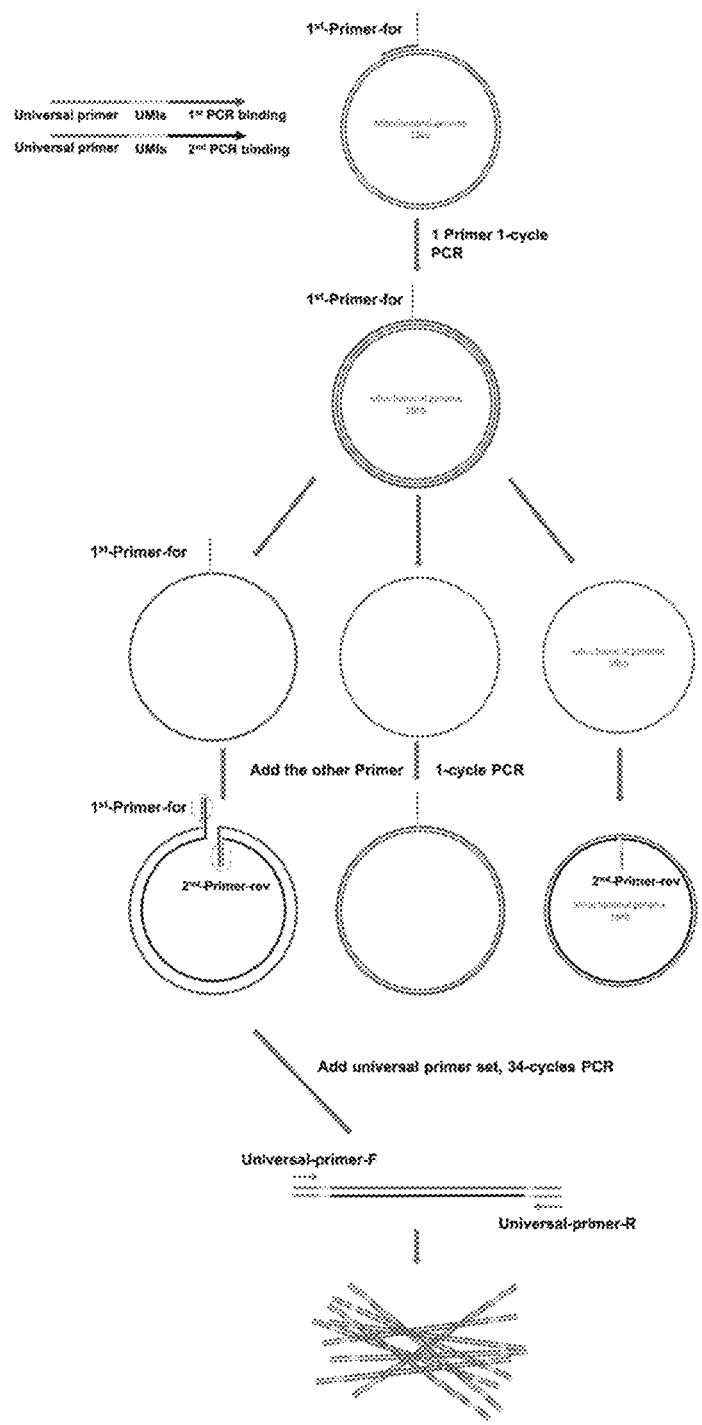
FIG. 1C is a schematic of individual DNA molecule labeling illustrated on a circular nucleic acid such as mitochondrial DNA (mtDNA).

A PCR-directed method has been developed to label individual DNA molecules in cells. The unique molecular identifiers (UMIs) are used to correct the errors during PCR (Smith & Sudbery, *Genome Res* 27, 491-499, doi:10.1101/gr.209601.116 (2017)). (FIG. 1A). In general, DNA is amplified by two rounds of one-cycle PCR with respective UMI-containing primers. After that, two universal primers are used to amplify the labeled amplicons (FIG. 1C). In the end, the labeled DNA come from different samples are pooled together to make a library that can be sequenced on a Nanopore MinION device.

Figure 1D:
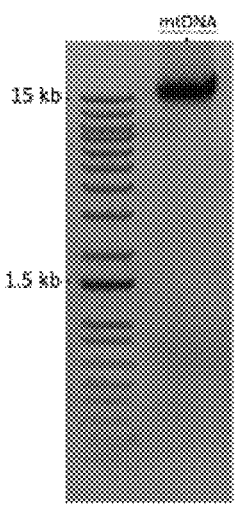
FIG. 1D is a photograph of an electrophoretic gel showing the 16.5 kb of full-length mtDNA are amplified using optimized PCR.
Figure 1E:
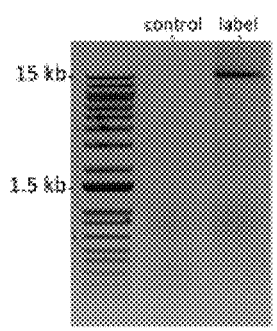
FIG. 1E is a photograph of an electrophoretic gel showing mtDNA from purified 293T genome labeled using the aforementioned method (label lane) without non-specific amplification (using only universal primers to amplify genome, control lane).

The universal primers are designed to avoid non-specific amplification in either the human or mouse genome (FIG. 1E). The UMIs structure is designed to avoid secondary structure. Because this is a PCR based method, it is applicable to label any DNA in the cell.

Different polymerases were tested in the PCR reaction to efficiently amplify the 16.5 kb of full-length mtDNA (FIG. 1D).

The whole genome extracted from 293T cells by QIAGEN DNeasy Blood & Tissue Kits are used to label the 16.5 kb of full-length mtDNA.

Results

Results showed that full-length mtDNA could be labeled with UMIs using this pipeline (FIG. 1E).

Example 2: Establishment of Nanopore MinION Sequencing Platform

Materials and Methods

To test the performance of Nanopore MinION sequencer in the Stem Cell and Regeneration lab, several trial sequencing runs were done on R9.4 and R9.5 flow cells with Rapid, 1D and 1D2 library preparation kits.

Results

The rapid and 1D kits are compatible with R9.4 flow cells to provide standard 1D reads (sequence one strand of input DNA), while the 1D2 kit is compatible with R9.5 flow cells to generate a mix of 1D reads and 1D2 reads (sequence one strand followed by its complementary strand). In general, the 1D and 1D2 kits provide the best yield and alignment identity of raw reads. A 24 h sequencing run using the 1D library preparation kit on a R9.4 flow cell can generate 1.4 GB of reads, while 48 hours of sequencing run using the 1D2 kit on a R9.5 flow cell can generate about 1.9 GB of reads (Table 2).

TABLE 2

Summary of trial sequencing run using different Nanopore kits

| DNA | Library preparation kits | Running time (hours) | Reads yield (GB) | Average reads length (bp) |
|---|---|---|---|---|
| Mouse mitochondria Amplicon | Rapid | 48 | 0.7 | 2300 |
|  | 1D | 24 | 1.5 | 5859 |
| E. coli k12 genome | Rapid | 24 | 0.6 | 9363 |
|  | $1D^2$ | 48 | 1.9 | 5353 |
|  | 1D | 4 | 0.3 | 8055 |

The alignment of reads to the reference genome showed an even coverage, which means the labeling and sequencing method comes without regional bias (FIG. 2A). In particular, reads are generated at the same time of sequencing run, which allows real-time control of reads quality and yield. Combining with the feature that flow cells can be washed and reused, this real-time control could potentially reduce the sequencing cost.

The rapid kit uses a transposase-based method to add sequencing adapters, which will fragment DNA and make it not suitable for amplicon sequencing. But it is good for whole genome sequencing since it does not ask for the fragmented genomic DNA. 1D and 1D2 kits use a ligation-based method to add sequencing adapter so that they are suitable for the disclosed application. The 1D2 reads show a higher consensus accuracy, but it takes more time to prepare library and the additional procedure lead to the shearing of DNA.

E. coli genome sequencing showed that 1D kit can generate a higher average length of reads compared with 1D2 kit (Table 2). Based on this, the 1D kit was selected for sequencing amplicon after individual-DNA molecule labeling.

Next, the ability of Nanopore sequencing by the 1D kit to generate reads spanning the full length of the amplicon was tested. Amplicons of different length, including 7.7 kb, 8.6 kb, 11 kb, 11.9 kb, 12.7 kb, and 16.5 kb, were tested. The length distribution showed that even 16.5 kb amplicons can be sequenced in a single read (FIG. 2B-2D).

In addition, a number of small fragments appeared in the reads of some sequencing runs. Further analysis showed those reads cannot be mapped to the reference. It is believed that they come from the random priming of primers in long-range PCR and can not be purified by the size selection of AMPure beads. This indicates that an additional size selection either by gel extraction or Bluepippin is preferred.

Example 3: Establishment of an Exemplary Bioinformatics Pipeline to Analyze Long-Read Data Materials and Methods Nanopore sequencing is known to generate ultra-long reads which are much longer than any other sequencing platform in the market. Those reads are error prone with an average alignment identity of 82.73% (Jain et al., Nat Biotechnol 36, 338-345, doi:10.1038/nbt.4060 (2018)). An exemplary bioinformatic pipeline using published algorithms for a proof-of-principle study.

Several of prevalent algorithms were tested to determine the performance of alignment and SNPs calling, including bwa-mem v0.7.17, mininap2.1, graphrmap v0.5.2. samtools v1.9, nanopolish vW.11.0 (Jain et al., Nat Biotechnol 36, 338-345, doi:10.1038/nbt.4060 (2018), Li, Bioinformatics 34, 3094-3100, doi:10.1093/bioinformatics/bty191 (2018), Sovic et al., Nat Commun 7, 11307, doi:10.1038/ncomms11307 (2016)).

The reads in this test come from a multiplexed amplicon (8.6 kb and 7.7 kb) sequencing of mouse mtDNA, basecalled by the official algorithm termed Albacore.

Results

Figure 3A:
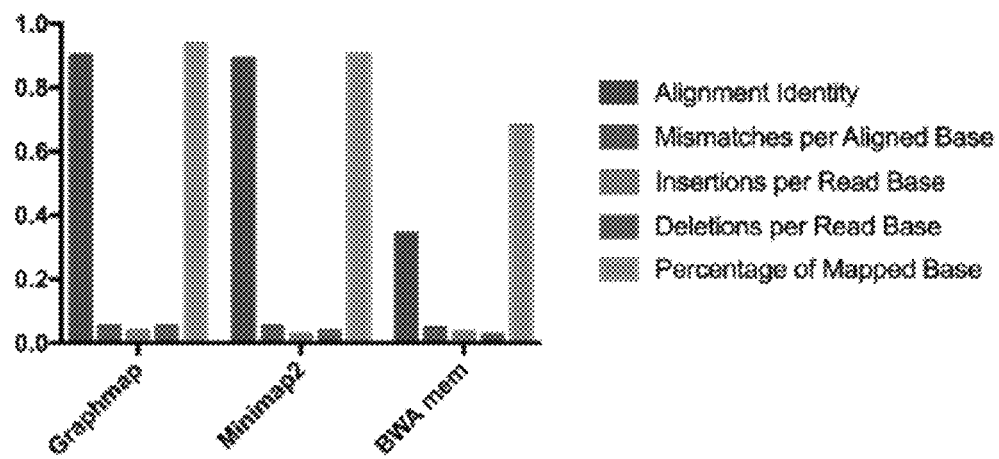
FIGS. 3A-3C illustrate the establishment of a data-analysis pipeline.

Results showed that graphmap has the best performance among the three alignment algorithms, with 89.81% of median alignment identity and 93.40% of base mapped to the reference (FIG. 3A). The alignment shows a comparable amount of errors of mismatches, insertions and deletions. Bwa-mem struggled in phasing those long reads (FIG. 3A).

Figure 3B:
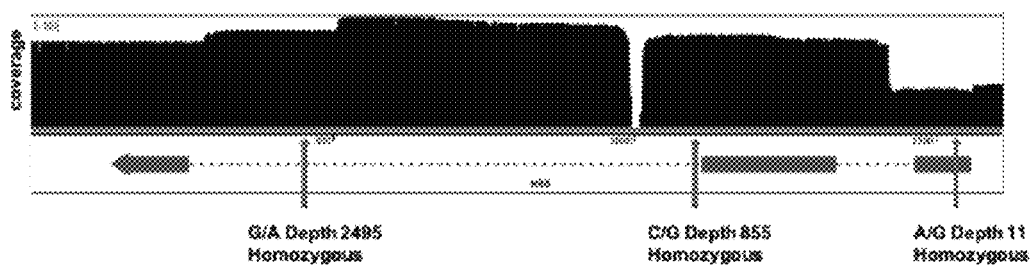

Targeted sequencing of human HBB locus with distinct coverage distribution was performed to determine if reliable SNPs calling is accessible for Nanopore reads. Sanger sequencing identified that there are the only 3 SNPs located in this gene. Targeted locus amplification was used to enrich this locus and gave rise to uneven coverage after sequencing (de Vree et al., Nat Biotechnol 32, 1019-1025, doi:10.1038/nbt.2959 (2014)) (FIG. 3B). Samtools and nanopolish were used to call the SNPs individually using the default parameters.

Figure 3C:
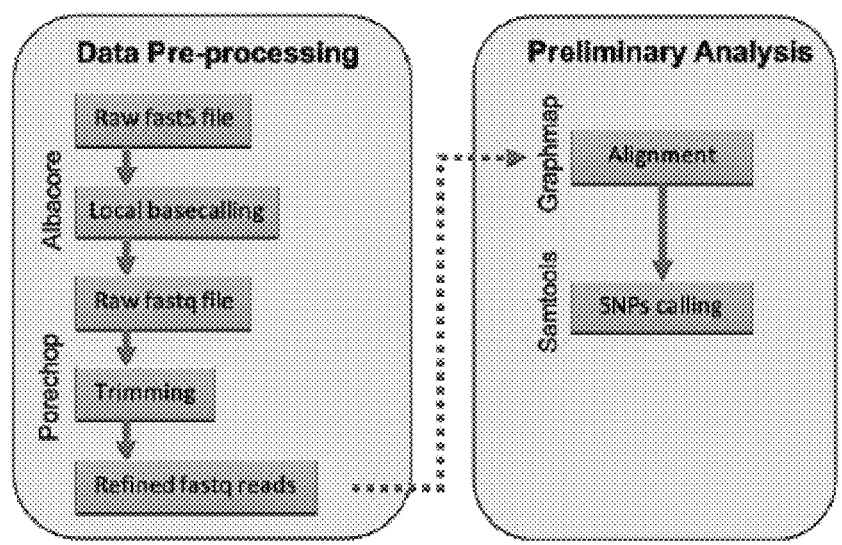

Results showed that samtools successfully called the only three SNPs in the HBB gene without any false positive, and the quality score are 222, 217 and 41, respectively. Nanopolish called the three SNPs together with ten false positives, those false positive SNPs come with relatively high-quality score, which makes it hard to filter the SNPs after initially SNP calling. Taken all together, an emplary bioinformatic pipeline to analyze Nanopore data by using graphmap and samtools was established (FIG. 3C). This pipeline can also be utilized with other signal-level algorithms

Example 4: mtDNA Labeling in One Hundred 293T Cells

Materials and Methods

The single molecule labeling method was first tested on mitochondrial DNA with a less developed version (only labeling one end of DNA with a UMI). A complete protocol to work from cell lysis to DNA labeling was also developed (FIG. 4A).

Cells are prepared in PBS, and then lysed in RIPA buffer on ice to release mtDNA. After the reaction is diluted and the DNA digested with restriction enzyme to linearize mtDNA.

An AMPure beads-based size selection is performed to clean up DNA and remove small fragments for downstream PCR. One-cycle PCR as described above is used to label mtDNA with UMIs.

The labeled DNA is amplified using universal primers.

A second round of PCR can be done if the yield is not enough for preparing sequencing library.

Currently, this protocol is effective for labeling mtDNA from as few as ten 293T cells (FIG. 4C).

Results

In this Example, the protocol was used to label mtDNA in one hundred 293T cells with UMIs. After collecting enough UMIlabeled DNA, DNA was purified by Bluepippin and AMPure beads. The results showed the size selection by Bluepipin can remove all of the small fragments, while size selection by AMPure beads cannot eliminate them (FIG. 4D). DNA from the two purifications were combined and made into a 1D library for sequencing in MinION. A 12-hour of sequencing run generated 407 MB of reads.

A further pipeline was established to extract UMIs and group reads (FIG. 4E). First, the 5' end sequence of reads was extracted based on the designed adapter structure. A 20% error tolerance is set to cope with the low raw-read accuracy of Nanopore sequencing. 38% of reads are processed. After that, the two flanking sequences were trimmed off the adapter using the same error tolerance, leaving the potential UMIs for downstream analysis.

3478 unique UMIs were identified, and the initial reads can be grouped together based on the UMI sequence.

In summary, the preliminary data show that: (1) The PCR-directed method for individual DNA molecule labeling is feasible to label DNA either from the extracted genome (for nuclear DNA labeling) or from 10 cells (for mtDNA labeling). (2) Nanopore MinION sequencing is capable of sequencing the whole amplicon in one read without bias or compromise in yield. (3) It is possible to use only the long reads produced by Nanopore sequencing to call DNA mutations, even in low-coverage regions.

Example 5: Long-read Individual-molecule Sequencing Reveals CRISPR-induced Heterogeneity in Human ESCs Materials and Methods Generation of the Knock-In hESC Line The H1 hESC line was purchased from WiCell and cultured in Essential 8™ medium (ThermoFisher) on hLaminin521 (ThermoFisher) coated plate in a humidified incubator set at 37° C. and 5% CO2.

Electroporation of CAS9 RNP was done using a Neon Transfection System (ThermoFisher) using the following setting: 1600 v/10 ms/3 pulses for 200,000 cells in Buffer R (Neon Transfection kit) premixed with 50 pmol Cas9 protein (CAT #M0646T, New England Biolabs), 50 pmol single guide RNA (sgRNA) and 30 pmol single-stranded oligodeoxynucleotides (ssODN, purchased from Integrated DNA Technologies, Inc.) template.

After 48 hours, single cells were collected and seeded at 1,000 single cells per well (6-well format). Seven days later, single colonies were picked for passaging and genotyping. The EPOR sgRNA sequence including protospacer adjacent motif (PAM) is 5'GCTCCCAGCTCTTGCGTCCA-TGG (PAM)3' (SEQ ID NO:8), which was synthesized in vitro by MEGAshortscript™ T7 Transcription Kit (ThermoFisher).

CRISPR-Cas9 Editing of hESCs

CRISPR-Cas9 editing of the PANX1 locus in H1 hESCs were performed in the same way as the generation of knock-in hESCs except for the omission of the ssODN template. After 48 hours, cells are collected for the genome extraction and library preparation. The Pan1 sgRNA sequence is 5'ATCCGAGAACACGTACTCCG-TGG (PAM)3' (SEQ ID NO:9) and Pan3 sgRNA is 5'GCTGCGAAACGCCAGAACAG-CGG(PAM)3' (SEQ ID NO:10).

UMI Primer Design

The UMI primer contains a 3' gene-specific sequence, a UMI sequence, and a 5' universal primer sequence. The 3' gene-specific sequence is designed with the same principle as PCR primers. A sequence with an annealing temperature higher than 65° C. was chosen to improve specificity to the target gene. The internal UMI sequence consists of multiple random bases (denoted by Ns). The number of random bases is determined by the number of targeted molecules. A short UMI sequence (10-12 nt) was chosen to reduce the sequencing errors within the UMI. A unique sequence structure in the UMI (e.g. NNNNTGNNNN (SEQ ID NO:2)) was chosen to avoid homopolymers that may introduce errors due to polymerase slippage or low accuracy of Nanopore sequencing in these sequences. Several studies have also pointed out that both Illumina and PacBio are prone to errors in such regions (Minoche et al., *Genome Biol* 12, (2011), Weirather et al., F1000Res 6, 100 (2017)). The structured UMI design also serves as a quality control in the UMI analysis. The 5' universal primer sequence is used to uniformly amplify all UMI tagged DNA molecules. It is designed to avoid non-specific priming in the target genome.

UMI Labeling

The primers used in this study are shown in Table 3.

| Primer | Sequence |
|---|---|
| Universal primer | CATCTTACGATTACGCCAACCAC (SEQ ID NO: 1) |
| EPOR UMI primer | CATCTTACGATTACGCCAACCACNNNNNNNN NNNGTTGAGATGCCAGAGTCAGATAC (SEQ ID NO: 11) |
| EPOR short reverse | TGCCAGCTTTGAGTACACTATC (SEQ ID NO: 12) |
| EPOR long reverse | TAACCTCCCGGACCCCAAGTTCG (SEQ ID NO: 13) |
| Pan1 UMI primer | CATCTTACGATTACGCCAACCACTGCGGNN NNNTGNNNNNGACACATTCTCCCAGGCCCT ACTT (SEQ ID NO: 14) |
| Pan1 reverse | CAGAGTCCCTTCTGCTCTCTGTCC (SEQ ID NO: 15) |
| Pan3 UMI primer | CATCTTACGATTACGCCAACCACTGCGGNN NNNTGNNNNNGCATCCCAGGCCTAATGTGG AGTT (SEQ ID NO: 16) |
| Pan3 reverse | GTCAGATTTCCCCACTGGGCTCTT (SEQ ID NO: 17) |

Table 3 sequences identifiers: SEQ ID NO: 1 (universal primer), SEQ ID NO: 11 (EPOR UMI primer), SEQ ID NO: 12 (EPOR short reverse), SEQ ID NO: 13 (EPOR long reverse), SEQ ID NO: 14 (Pan1 UMI primer), SEQ ID NO: 15 (Pan1 reverse), SEQ ID NO: 16 (Pan3 UMI primer), SEQ ID NO: 17 (Pan3 reverse).

Genomic DNA is extracted using the Qiagen DNeasy Blood & Tissue Kit. The concentration is determined using a Qubit 4 Fluorometer (ThermoFisher). The UMI labeling step is done by one round of primer extension with a high-fidelity DNA polymerase. The reaction setup is similar to a standard PCR reaction, but with only one UMI primer. The UMI labeling reaction is set up as follows: 50 ng DNA, 1 µM UMI primer, 12.5 µl 2× Platinum™ SuperFi™ PCR Master Mix, and H$_2$O in a total volume of 25 µl. The UMI labeling is performed on a thermocycler with a ramp rate of 1° C. per second using the following program: 98° C. 1 min, 70° C. 5 s, 69° C. 5 s, 68° C. 5 s, 67° C. 5 s, 66° C. 5 s, 65° C. 5 s, 72° C. (5 min for the 7 kb targets, 10 s for the 168 bp target), 4° C. hold. After UMI labeling DNA is purified by AMPure XP beads, followed by PCR amplification using the universal primer and the gene-specific reverse primer. This amplification will generate enough UMI-labeled DNA for downstream sequencing. In addition to one-ended labeling, two-ended UMI labeling can also be achieved by performing an additional UMI-labeling step with a reverse primer tagged with a UMI (FIG. 9A). Two-ended UMI labeling could increase analyzable reads and provides extra benefit in accuracy. However, because it was found that UMI labeling is limited by primer efficiency, one-ended labeling is believed to cover more molecules. Additional UMI-labeling and purification steps result in higher loss of DNA of interest. Since the procedure of one-ended labeling is simple and efficient, one-end UMI labeling for all experiments in Examples 5 and 6.

Library Preparation and Sequencing

For Nanopore sequencing, library preparations were done using the ligation sequencing kit (Cat #SQKLSK109, Oxford Nanopiore Technologies). The sequencing runs were performed on an Oxford Nanopore MinION sequencer using R9.4.1 flow cells. Base calling of Nanopore reads was done using the official tool termed Guppy (v3.2.1). For PacBio sequencing, library preparations were done using the Sequel Sequencing Kit 3.0. The sequencing runs were performed by the BIOPIC core facility at Peking university (Beijing, China) on a PacBio Sequel using Sequel SMRT Cell 1M v3. HiFi Reads were generated by the official tool termed ccs (v3.4.1). All procedures were preformed according to manufacturer's protocols. For Illumina sequencing, library preparations were performed using the NEBNext Ultra II DNA Library Prep Kit for Illumina. An unrelated RNA library prepared using the same kit was pooled to increase the complexity of final library. The sequencing of paired-end 150 bp reads was done on an Illumina Miniseq.

Data Processing

VAULT was developed for data analysis. Most of the codes were written in Python 3.7, while some modules were written in Bash. In general, VAULT uses several published algorithms for UMI extraction, alignment, and variant calling. By default, it utilizes cutadapt (Martin, Cutadapt removes adapter sequences from high-throughput sequencing reads. 2011 17, 3 (2011)), minimap2 (Li, *Bioinformatics* 34, 3094-3100 (2018)), samtools (Li et al., *Bioinformatics* 25, 2078-2079 (2009)), and sniffles (Sedlazeck et al., *Nat Methods* 15, 461-468 (2018)). The whole analysis can be done with one command. In brief, Nanopore reads are trimmed to remove adapter sequences, and then aligned to the reference gene for extraction of mappable reads. Cutadapt is used to extract UMI sequence, followed by counting of the occurrence of each UMI, which reflects the number of reads in each UMI group. If a structured UMI (NNNNTGNNNN (SEQ ID NO:2)) is used in the experiment, the program will also check the UMI structure and separate them to perfect UMIs and wrong UMIs. Next, based on a user-defined threshold of minimum reads per UMI group, the program bins reads for eligible UMIs. The grouped reads will be subjected to minimap2 for alignment, followed by SNP calling by samtools and SV calling by sniffles. After finishing all variant calling, a final data cleanup is performed to combine individual variant call files (VCF) together and filter the VCF. The number of reads in UMI groups and the corresponding UMI sequence will be written in the ID field of the VCF. Individual folders named after the UMI sequence will be saved to contain the alignment summaries and BAM files of every UMI group. VAULT supports both long-read data and single-end/paired-end short-read data. The data analysis pipeline employs parallel computing for each UMI group, which avoids crosstalk during data analysis and accelerates the process. A typical analysis of 2.5 million long reads will take around four hours on a 32-core workstation.

Results

Figure 8:
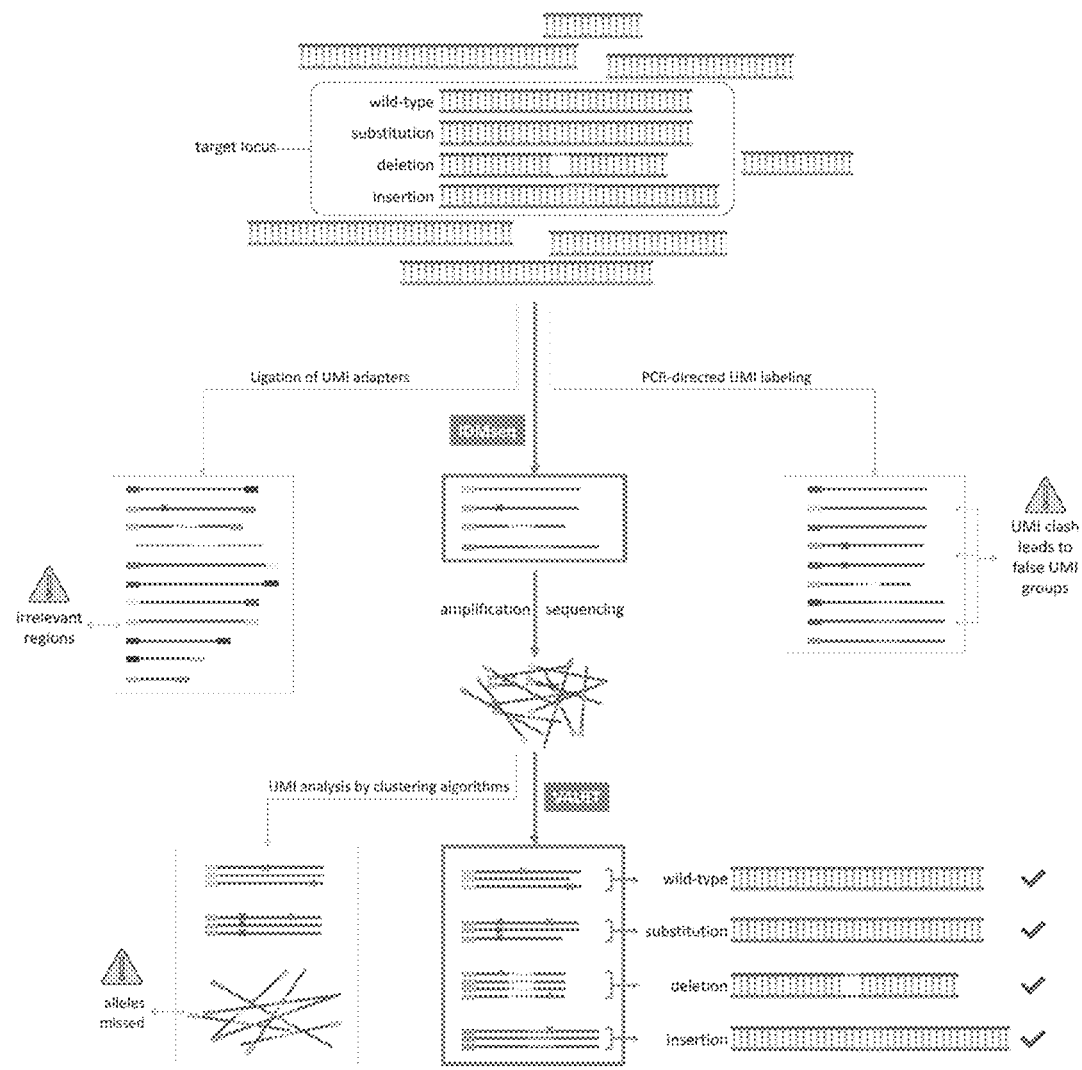
FIG. 8 is a schematic representation showing steps utilized in some embodiments of the disclosed methods, and a particular embodiment also referred to in Example 5 as IDMseq (center workflow) contrasted with ligation of UMI adaptors (left side workflow) and PCR-directed UMI labeling (right side workflow), and analyzed by VAULT (center workflow) contrasted with UMI analysis by clustering algorithms (right side workflow). A given population of cells (symbolized by dotted oval) may contain different alleles of a target locus, which accounts for a small proportion of the pool of genomic DNA. The first step of targeted molecular consensus sequencing is labeling of the variant alleles with UMI. Ligation-based and PCR-directed UMI labeling are two alternative methods. Ligation-based UMI labeling will label irrelevant regions and the low efficiency of ligation will also omit a proportion of target alleles (greyed out in the middle left panel). PCR-directed UMI labeling is highly efficient but will result in UMI clashes (one original molecule labeled with multiple UMIs, leading to false UMI groups, middle right panel). IDMseq is the only method with high labeling efficiency and can faithfully retain the allele information (variants and frequency). After UMI labeling, the DNA with UMIs are amplified for sequencing in appropriated platforms (e.g., Illumina, Nanopore or PacBio). In the data analysis step, the algorithm needs to identify reads with the same UMI and use these to get the consensus sequence of the allele. This step can be done with read-clustering algorithms that work well for fixed-length reads of short-read sequencing (e.g. Illumina). However, this strategy could miss reads with complex changes such as those uncovered by long-read sequencing, which prevents detection of deletions, insertions and complex structural variants (lower left panel). VAULT performs a BLAST-like strategy to locate UMI sequence in reads regardless of length and structure. VAULT analysis thus preserves the sequence information of all types of alleles and their frequency (lower middle and right).

Molecular consensus sequencing has been developed to enhance the accuracy of next-generation sequencing (NGS) using unique molecular identifier (UMI)(Kinde et al., *Proc Natl Acad Sci USA* 108, 9530-9535 (2011), Hiatt et al., *Nat Methods* 7, 119-122 (2010), Salk et al., *Nat Rev Genet* 19, 269-285 (2018)). The main concepts of this strategy include barcoding each molecule before amplification, and correcting sequencing error using the consensus sequence of reads containing the same barcode, and hence eliminating the random errors introduced by sequencing chemistry or detection. However, current strategies are inadequate for many types of sequences especially the large structural variants or repetitive sequences (FIG. 8). Single molecule sequencing technologies can better resolve complex genetic variants by providing long reads, but they have a lower raw read accuracy (Salk et al., *Nat Rev Genet* 19, 269-285 (2018)).

To overcome these limitations, a treated termed targeted Individual DNA Molecule sequencing (IDMseq) was developed. IDMseq ensures that each original DNA molecule is uniquely represented by one UMI group (a set of reads sharing the same UMI) after sequencing, thus preventing false UMI groups and allowing quantification of allele frequency in the original population (FIGS. 8 & 9A). It is designed to be adaptable to various sequencing platforms, and combines error correction by molecular consensus with long-read sequencing, thus enabling sensitive detection of all classes of genetic variants, including SNVs, indels, large deletions, and complex rearrangements.

Figure 10A:
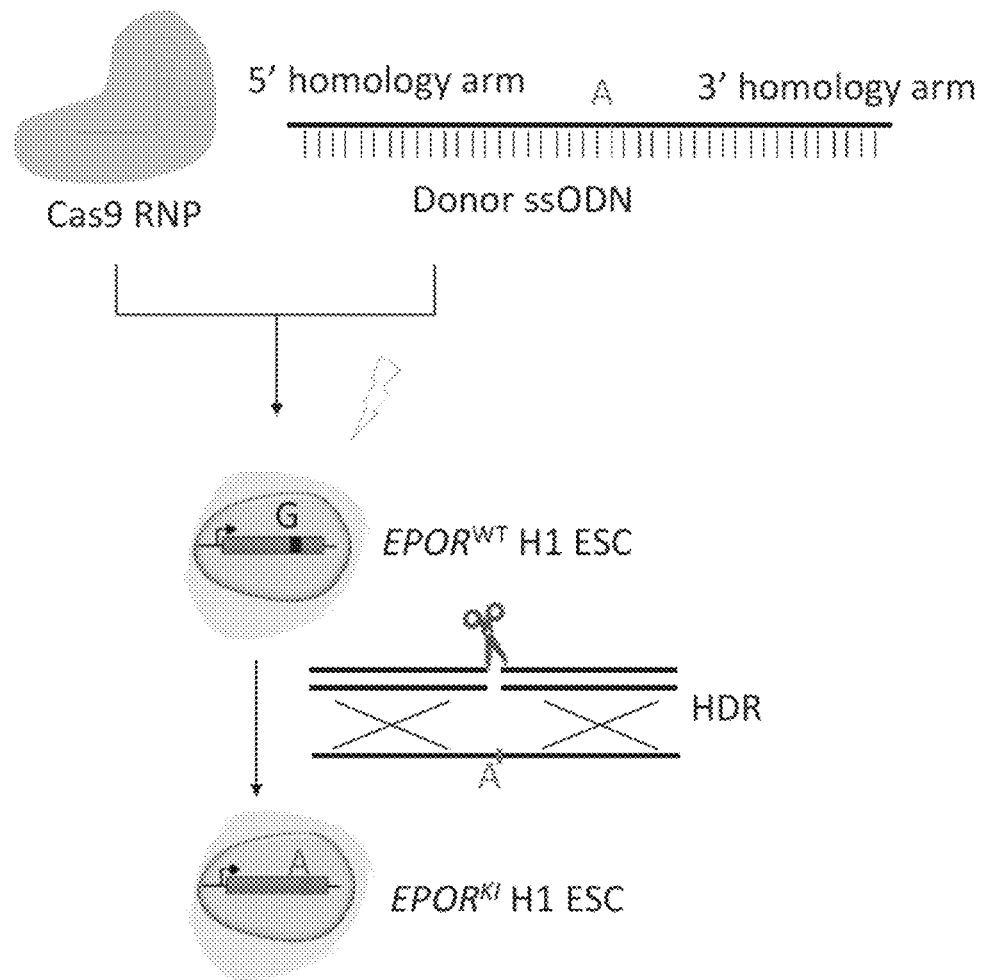
FIG. 10A is a schematic representation of an experimental design utilized in the experiments of Example 5. Cas9 RNP and ssODN were electroporated to H1 ESCs to generate homozygous G>A single-base substitution in the EPOR gene.
Figure 10B:
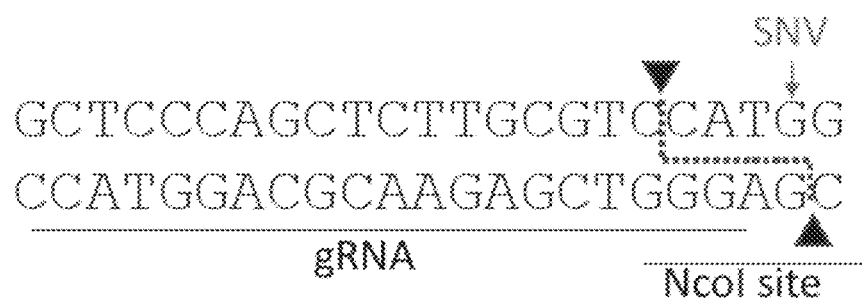
FIG. 10B is a schematic of the Cas9 target site and the NcoI restriction site (SEQ ID NOS:8; 25). A restriction enzyme digestion assay was used to identify the knock-in hESC clones. Wild-type EPOR gene contains a NcoI site and thereby can be digested. The Knock-in allele will lose the NcoI site and cannot be digested.

To determine if IDMseq can detect subclonal variants below the sensitivity limit of NGS (~1% (Ley et al., *Nature* 456, 66-72 (2008), Zagordi et al., *Nucleic Acids Res* 38, 7400-7409 (2010))), synthetic cell populations harboring a mutation at various pre-determined allele frequencies were constructed. A homozygous single nucleotide variant (SNV) was knocked into the EPOR 20 gene using CRISPR-Cas9 in the H1 human embryonic stem cells (hESCs) (FIGS. 10A-10B). A rare subclonal mutation in a population of cells is simulated by admixing the genome of knock-in and wild-type cells at different ratios.

First, tests were executed to determine if IDMseq could overcome the high base-calling error of Nanopore sequencing in rare mutation detection. A 168 bp stretch of DNA encompassing the knock-in SNV was labeled with UMIs and amplified from a population with the ratio of 1:100 between knock-in and wild-type alleles.

A bioinformatic toolkit called Variant Analysis with UMI for Long-read Technology (VAULT) was also developed to analyze the sequencing data (see methods). The results showed that 36.5% of reads contained high-confidence UMI sequences (Table 4).

TABLE 4

Summary of Individual Sequencing Runs

| Gene | Mutant allele frequency (%) | Amplicon Size | Sequencing platform | Read count | Reads with UMI | UMI groups for variant calling (>=5 reads) | UMI groups with introduced mutation | Somatic SNV count | Somatic SNV load Per megabase | SV Groups |
|---|---|---|---|---|---|---|---|---|---|---|
| EPOR | 1:100 (1%) | 168 bp | Nanopore | 17,634 | 6,444 | 284 | 2 (0.7%) | 0 | N/A | N/A |
| EPOR | 1:1,000 (0.1%) | 6,789 bp | PacBio | 227,206 | 136,399 | 3,184 | 4 (0.126%) | 273 | 8.9 | 3 |
| EPOR | 1:10,000 (0.01%) | 168 bp | Nanopore | 1,093,683 | 494,009 | 15,598 | 1 (0.006%) | 10 | 3.8 | N/A |
| EPOR | 1:10,000 (0.01%) | 168 bp | Illumina | 7,488,257 | 7,236,007 | 132,341 | 5 (0.004%) | 85 | 3.9 | N/A |
| PANX1 | N/A | 7077 bp | Nanopore | 2,761,805 | 613,147 | 3,566 | N/A | 293 | 11.6 | 200 (5.6%) |
| PANX1 | N/A | 6595 bp | Nanopore | 3,078,165 | 1,042,582 | 8,870 | N/A | 843 | 14.4 | 232 (2.6%) |

Based on a pre-set threshold of a minimum of 5 reads per UMI group, those reads are binned into 284 UMI groups. It is worth noting that every UMI group represents an original allele in the genome of the initial population.

Figure 11A:
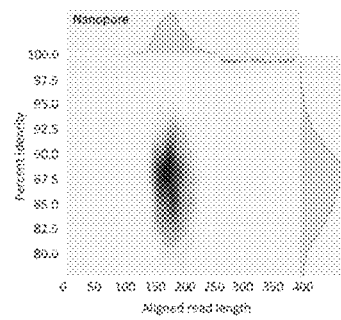
FIGS. 11A-11C are aligned read length vs. percent identity plot using kernel density estimation for Nanopore sequencing of the 1:10,000 population, Illumina sequencing of the 1:10,000 population, PacBio sequencing of the 1:1, 000 population.
Figure 11B:
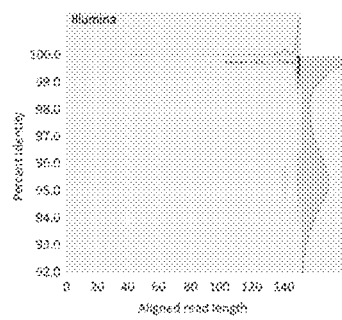
Figure 11C:
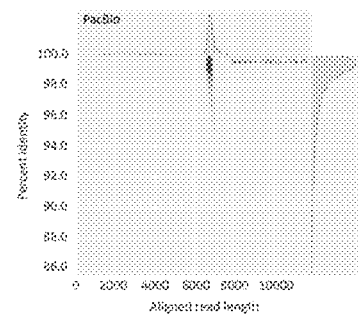

VAULT analysis showed that 2 UMI groups contained the knock-in SNV (FIGS. 11A-11C). Furthermore, no spurious mutation was detected. Importantly, when the trimmed reads were pooled for variant analysis without considering UMIs, no variant could be detected 35 by the same algorithms, proving the superior sensitivity afforded by IDMseq. These results suggest that IDMseq on the single-molecule Nanopore sequencing platform is able to accurately call rare variants without false positives.

Detection of rare variants in clinical settings often demands sensitivities well below that of prevailing NGS platforms (ca. $10^{-2}$). For instance, early cancer detection using circulating tumor DNA is estimated to require a sensitivity of at least 1 in 10,000 (Aravanis et al., Cell 168, 571-574 (2017)). To simulate this scenario, the same 168 bp region was sequenced in a population with the ratio of 1:10,000 between knock-in and wild-type alleles. It is worth noting that the UMI-labeling reaction contained only around 5 copies of the knock-in allele.

Figure 12A:
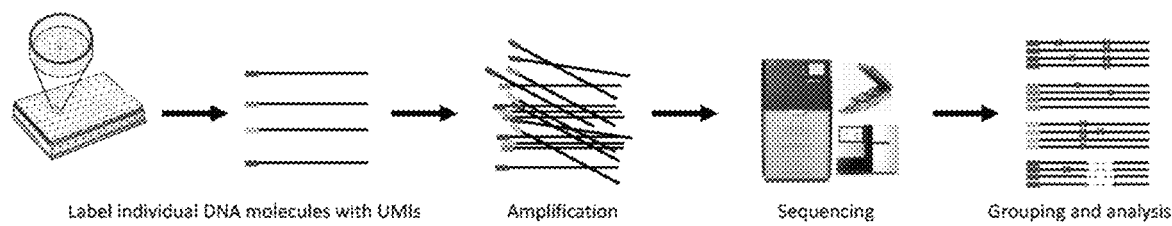
FIG. 12A is a schematic representation showing steps utilized in some embodiments of the disclosed methods, and a particular embodiment also referred to in Example 5 as IDMseq. Individual DNA molecules are labeled with unique UMIs and amplified for sequencing on appropriate platforms (e.g. Illumina, PacBio, and Nanopore). During data analysis, reads are binned by UMIs to correct errors introduced during amplification and sequencing. Both SNV and SV calling are included in the analysis pipeline.
Figure 12B:
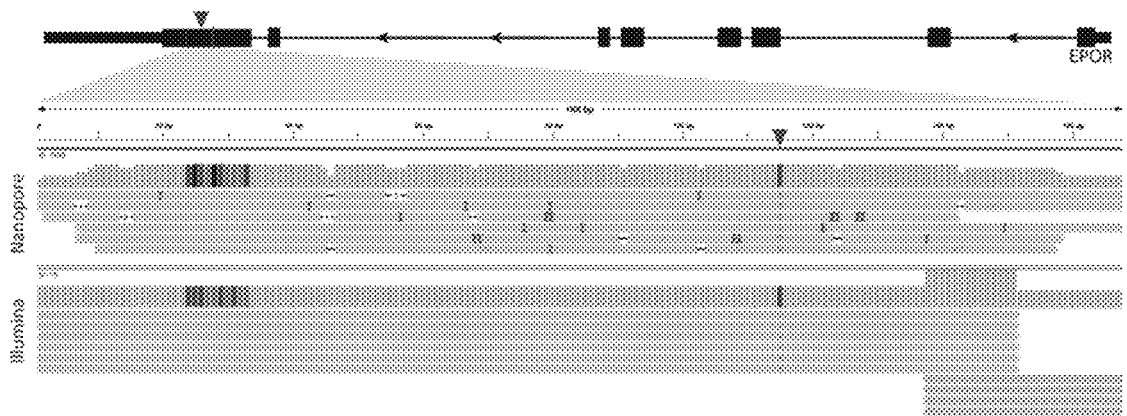
FIG. 12B is an illustration showing examples of Integrative Genomics Viewer (IGV) tracks of UMI groups in which the spike-in SNV in the 1:10000 population was identified by IDMseq and VAULT. The knock-in SNV is indicated by the triangle in the diagram of the EPOR gene on top, and also shown as "T" base in the alignment map. The gray bars show read coverage. The ten colored bars on the left side of the coverage plot represent the UMI sequence for the UMI group. Individual Nanopore (top) and Illumina (bottom) reads within the group are shown under the coverage plot.

A 48-hour sequencing run on the MinION acquired 1.1 million reads (FIGS. 11A-11C). VAULT showed that 45.2% of reads contained high-confidence UMI sequences (Table 4). These reads were binned into 15,598 UMI groups of which one ($0.6 \times 10^{-4}$) contained the knock-in SNV (FIG. 12B). Ten other SNVs were also identified in ten UMI groups. Consideration was given as to whether or not there were PCR artifacts, as the main source of errors in UMI consensus sequencing originates from polymerase replication error in the barcoding step (Filges et al., Scientific reports 9, 3503 (2019)). The Platinum SuperFi DNA polymerase used has the highest reported fidelity (>300× that of Taq polymerase). It not only significantly reduces errors in the barcoding and amplification steps, but also captures twice more UMIs in the library than Taq (Filges et al., Scientific reports 9, 3503 (2019)). Theoretically, Platinum SuperFi polymerase introduces ~6 errors in $10^6$ unique 168-bp molecules in the UMI-labeling step. Accordingly, this type of inescapable error is expected to be around 0.09 in 15,598 UMI groups, and thus cannot account for the observed SNV events. It was thus concluded that the ten SNVs are rare somatic mutations that reflect the genetic heterogeneity of hESCs as described previously (Merkle et al., Nature 545, 229-233 (2017)). These data provided an estimate of 3.8 somatic SNVs per megabase (Mb), which is consistent with the reported frequency of somatic mutation in coding sequence in normal healthy tissues (Martincorena et al., Science 348, 880-886 (2015)).

The length of 168-bp amplicon also allowed benchmarking against the industry standard Illumina sequencing, which features shorter reads but higher raw-read accuracy. The same 1:10,000 mixed population was then sequenced on an Illumina MiniSeq sequencer and obtained 7.5 million paired-end reads (FIG. 11A-11C). The results showed that 96.6% of reads contained high-confidence UMI sequences that were binned into 132,341 UMI groups, in which 5 ($4 \times 10^{-5}$) contained the knock-in SNV (Table 4, FIG. 12B). The calculated somatic SNV load was 3.9 per Mb, which closely matches the Nanopore data.

Figure 12C:
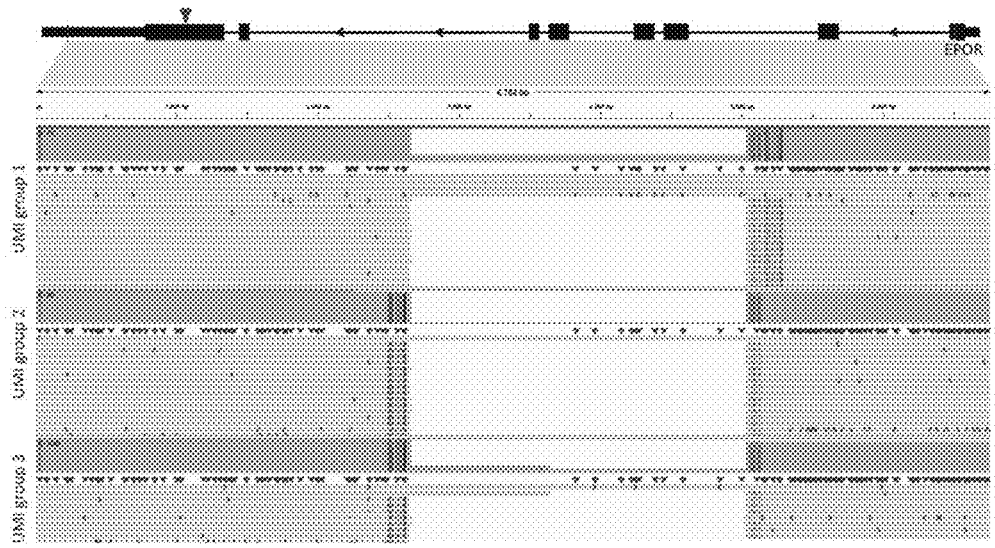
FIG. 12C is an illustration of showing large SVs detected by IDMseq in the 1:1000 population on the PacBio platform. Three UMI groups are shown with the same 2375 bp deletion. Group 1 represents one haplotype, and Group 2&3 represent a different haplotype. Colored lines represent the SNPs detected in each group. Thick boxes: exons; thin boxes UTRs. Thin vertical lines in the gene diagram represent PCR primer location.
Figure 12D:
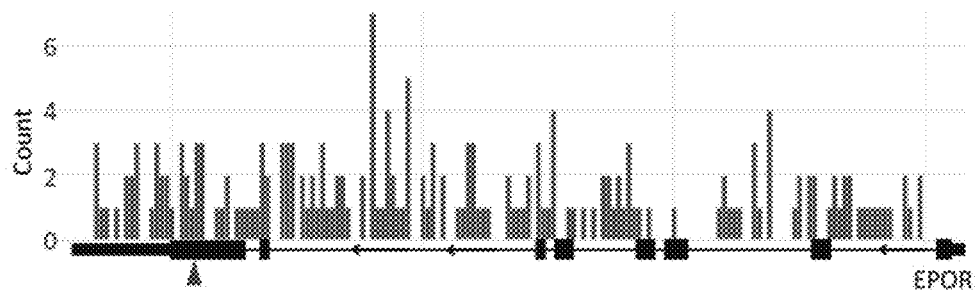
FIG. 12D is a plot showing distribution of SNVs detected by PacBio sequencing in conjunction with IDMseq and VAULT. One of the SNVs was also found in the Nanopore dataset. The spike-in SNV (1:1000) is indicated by the triangle.

IDMseq was next applied to a larger region (6,789 bp) encompassing the knock-in SNV in a population with 0.1% mutant cells on a PacBio platform (FIGS. 11A-11C). VAULT showed that 60.0% of the high-fidelity long reads contain high-confidence UMIs, binned into 3,184 groups. Four UMI groups ($1.26 \times 10^{-3}$) contained only the knock-in SNV. Another 186 groups contained 273 SNVs (174 groups with 1 SNV, 9 groups with 2 SNVs, and 3 groups with 27 SNVs, Table 4). Again, 30 polymerase error during barcoding (~0.82 error in 3,184 UMI groups) cannot account for the observed SNVs, indicating that most SNVs are true variants. Interestingly, structural variant (SV) analysis showed that the three groups with 27 SNVs shared the same 2,375 bp deletion. Haplotyping using the SNVs revealed that the three groups came from two haplotypes (FIG. 12C). This large deletion is far away from the Cas9 target site and thus less likely the result of genome editing. After excluding the SNVs in the large-deletion alleles, the remaining 192 SNVs distributed evenly in the region (FIG. 12D, Table 5).

TABLE 5

Summary of the frequency of SNVs in different annotation categories.

| Type | Count | Percent |
|---|---|---|
| downstream | 150 | 27.1% |
| exon | 98 | 17.7% |
| intron | 263 | 47.6% |
| splice site region | 2 | 0.4% |
| transcript | 19 | 3.4% |
| UTR 3 prime | 21 | 3.8% |

Figure 12E:
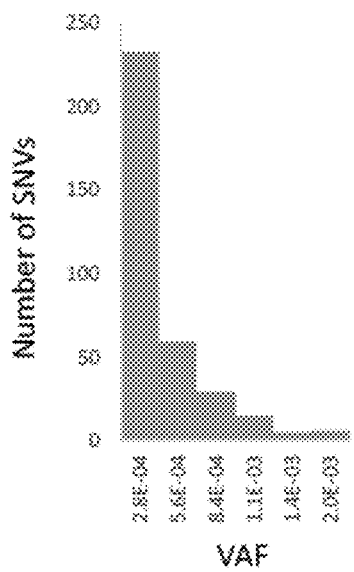
FIG. 12E is a plot showing the frequency distribution of the variant allele fraction of SNVs detected by IDMseq in PacBio sequencing of the EPOR locus.
Figure 12F:
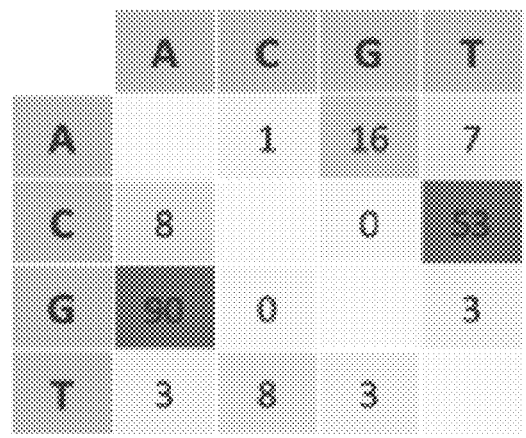
FIG. 12F is a chart showing the spectrum of base changes among somatic SNVs. The majority of base changes are G to A and C to T.

Functional annotation of the SNVs showed that 17 of 192 caused an amino acid change. The spectrum of base changes and distribution of variant allele frequency (VAF) are consistent with published work (Martincorena et al., Science 348, 880-886 (2015)) (FIGS. 12E, 12F). These data provide an estimate of about 8.9 somatic SNVs per Mb.

Figure 12G:
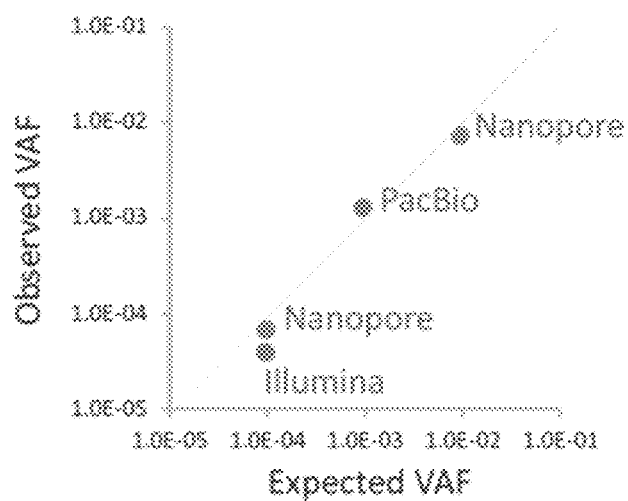
FIG. 12G is a plot showing comparison between observed VAF and expected VAF in different experiments and sequencing platforms.

Taken together these data showed that IDMseq provides reliable detection of rare variants (at least down to $10^{-4}$) and accurate estimate of variant frequency (FIG. 12G). It is useful for characterizing the spectrum of somatic mutations in human pluripotent stem cells (hPSCs).

Furthermore, it revealed a previously unappreciated phenomenon of spontaneous large deletion in hPSCs. Due to its large size and low frequency (VAF≈0.1%), this SV would have been missed by short-read sequencing or ensemble long-read sequencing. Yet, it is conceivable that such an SV could confer growth advantage to the cell carrying it, and therefore has implications for the safety of hPSC in clinical settings. These findings nicely demonstrate the power of the combination of long-read sequencing and IDMseq in resolving complex genetic heterogeneity.

Example 6: IDMseq Offers an Unbiased Quantification of the Frequency and Molecular Feature of the DNA Repair after Induced Double-Strand Breaks Induced by CRISPR-Cas9

Despite its widespread adoption of the CRISPR-Cas9 system as an efficient and versatile genome-editing tool, the impact of CRIPSR on human genome integrity remains poorly understood (Kosicki et al., *Nat Biotechnol* 36, 765-771 (2018), Ihry et al., *Nature medicine* 24, 939-946 (2018), Haapaniemi et al., *Nature medicine* 24, 927-930 (2018)). Previous work indicated that the most prevalent DNA repair outcomes after Cas9 cutting are small indels (typically <20 bp) (van Overbeek, et al., *Molecular Cell* 63, 633-646 (2016), Koike-Yusa et al., *Nature Biotechnology* 32, 267-273 (2014)). Recent studies revealed large and complex SVs over several kilobases represent a significant portion of the on-target mutagenesis effect of Cas9 (Kosicki et al., *Nat Biotechnol* 36, 765-771 (2018), Adikusuma et al., *Nature* 560, E8-E9 (2018)). Importantly, to date, the analysis of large-deletion alleles came either from ensemble amplicon sequencing (Kosicki et al., *Nat Biotechnol* 36, 765-771 (2018), Adikusuma et al., *Nature* 560, E8-E9 (2018)) or whole-genome sequencing (Adikusuma et al., *Nature* 560, E8-E9 (2018)). The former is prone to amplification bias, and the latter cannot adequately detect large and complex variants due to the limited read length. Thus, IDMseq was applied to hESCs following CRISPR-Cas9 editing, to offer an unbiased quantification of the frequency and molecular feature of the DNA repair outcomes of double-strand breaks induced by Cas9.

Figure 13A:
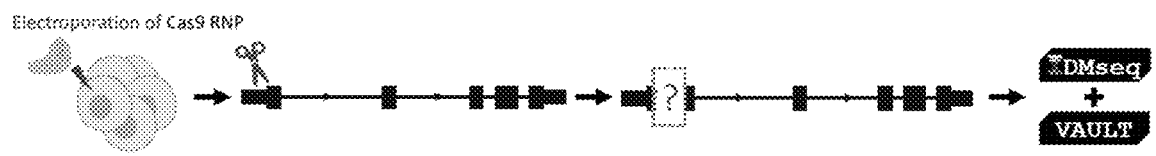
FIG. 13A is a schematic representation of an experimental design utilized in Example 5. Cas9 RNPs designed to cleave the first exon of PANX1 were electroporated to H1 hESCs. IDMseq was used to analyze the locus in edited hESCs 48 hours later.
Figure 13B:
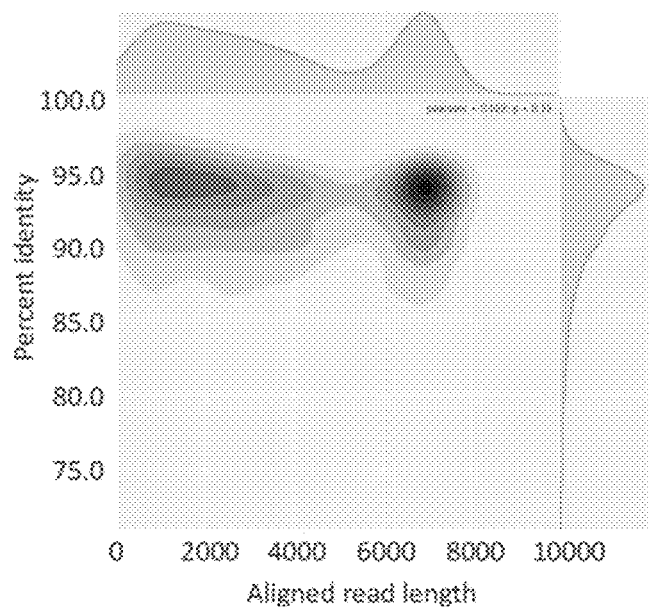
FIG. 13B is an aligned read length vs. percent identity plot using kernel density estimation of Nanopore sequencing data of a 7077 bp region encompassing the Cas9 cleavage.

Exon 1 (Pan1) and exon 3 (Pan3) of the Pannexin 1 (PANX1) gene were targeted with two efficient gRNAs (FIG. 13A). Forty-eight hours after electroporation of Cas9 complexed with the Pan1 or Pan3 gRNA, H1 ESCs were harvested for IDMseq. The surveyed region is 7,077 bp for Pan1 and 6,595 bp for Pan3. A 48 h Nanopore sequencing run yielded 2.8 million and 3.1 million reads for Pan1 and Pan3, which were binned into 3,566 and 8,870 UMI groups, respectively (Table 4, FIG. 13B, FIG. 14A).

Figure 13C:
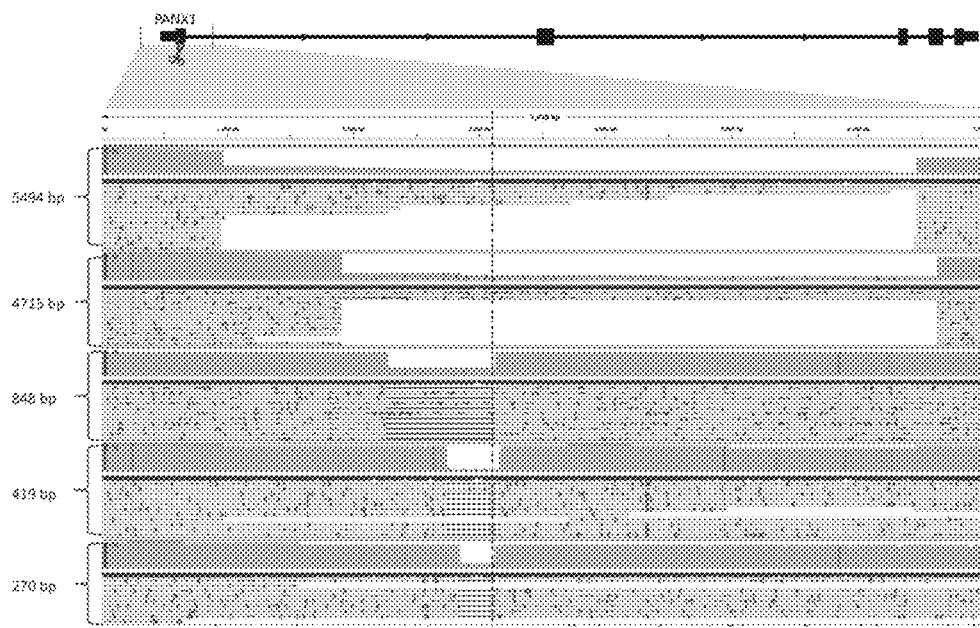
FIG. 13C is an illustration of large SVs detected by IDMseq and VAULT in edited hESCs. Five SV groups were shown with deletion length ranging from 270 bp to 5494 bp. The dotted line represents the Cas9 cutting site. The coverage of Nanopore reads is shown on top of each track in gray. The colored lines on the left side of the coverage plot represent the UMI for the group. Individual Nanopore reads within the group are shown under the coverage plot.
Figure 15A:
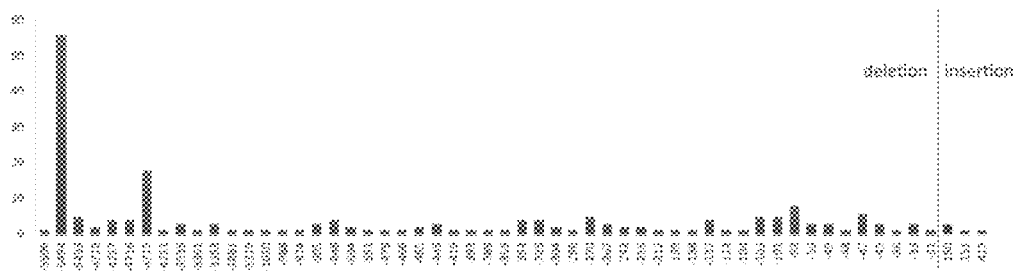
FIG. 15A is a plot showing that the frequency of deletions or insertions of different size detected in Pan1-edited hESCs. Certain deletions and insertions occur at disproportionally high frequencies. For example, a 5494 bp deletion was found in 56 UMI groups, which indicates a possible hotspot of Cas9-induced large deletion.

First, SVs (>30 bp) were surveyed in UMI groups. After SV calling and filtering out lowly supported SVs (see methods), 200 (5.6%) of the 3,566 UMI groups contained 200 SVs in Pan1-edited cells, including 195 deletions and 5 insertions. The size of SVs ranged from 31 to 5,506 bp (FIG. 13C, FIG. 15A). Intriguingly, some large deletions were independently captured multiple times. For example, 56 (28.0%) UMI groups have the same 5,494-bp deletion and 18 (9.0%) UMI groups have the same 4,715-bp deletion. For the insertion variants, 3 of the 5 UMI groups shared the same SV.

Figure 15B:
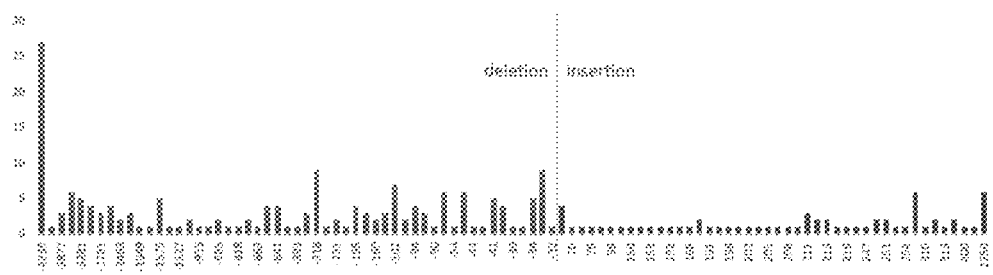
FIG. 15B is a plot showing the frequency of different size deletions or insertions detected in Pan3-edited hESCs. Certain deletions and insertions occur at disproportionally high frequencies. For example, a 4238 bp deletion was found in 27 UMI groups, which indicates a possible hotspot of Cas9-induced large deletion.

When a different gRNA (Pan3) was used, 232 (2.6%) of 8,870 UMI groups contained 240 SVs 35 (178 deletions, 50 insertions and 12 inversions), with size ranging from 31 to 4,238 bp (FIG. 15B). Importantly, reoccurring SVs were also detected with Pan3. Twenty-seven (32.1%) UMI groups shared the same 4,238-bp deletion, and 6 (2.5%) groups shared a 2,750-bp insertion. These data provided the first quantitative evidence that the repair outcome of Cas9 cutting is not random and there are likely hotspots for Cas9-induced large deletions or insertions.

Figure 13D:
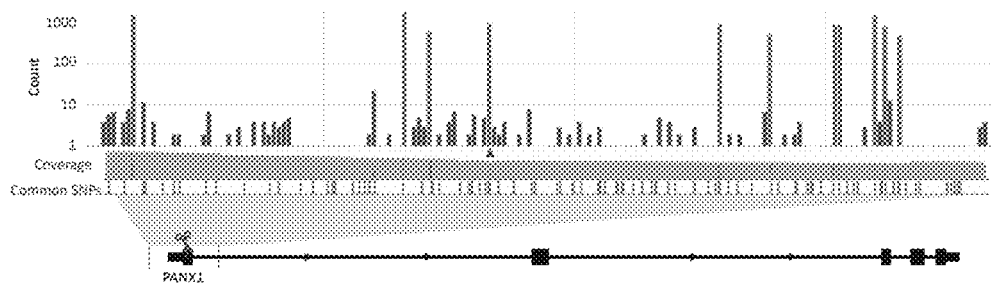
FIG. 13D is a plot showing distribution of SNVs detected by IDMseq and VAULT in edited hESCs. Somatic SNVs and cell-line specific SNVs are shown. Somatic SNVs cannot be detected if variant calling is done en masse without UMI analysis (see the coverage track). Cell-line specific SNVs are detected in ensemble analysis (see colored lines in the coverage track) and most of them have been reported as common SNPs in dbSNP-141 database (Common SNPs track). The Cas9 cut site is indicated by a triangle.
Figure 13E:
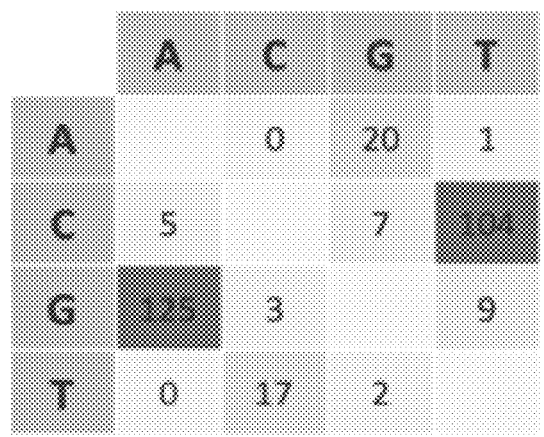
FIG. 13E is a chart showing analysis of somatic mutations detected in CRISPR-edited hESCs based on base change. The majority of base changes are G to A and C to T.
Figure 15C:
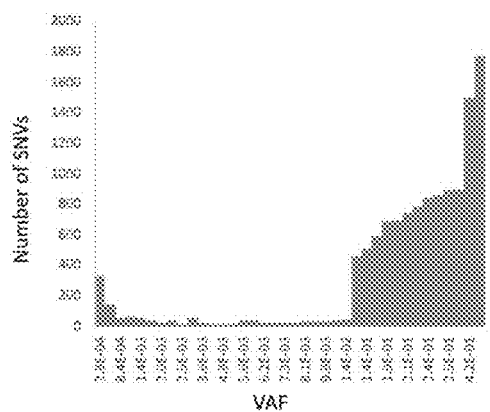
FIGS. 15C-15D are plots showing the frequency distribution of the variant allele fraction of SNVs detected by IDMseq in Nanopore sequencing of the PANX1 locus in Pan1-edited hESCs (15C), and Nanopore sequencing of the PANX1 locus in Pan3-edited hESCs (15D).
Figure 15D:
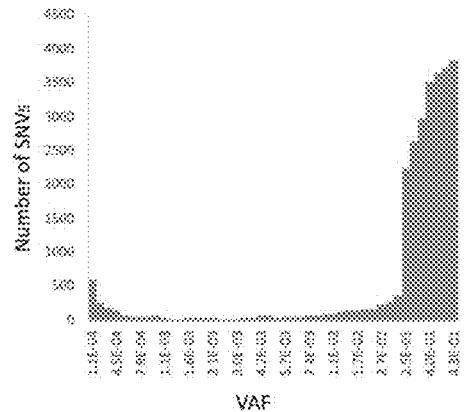
Figure 15E:
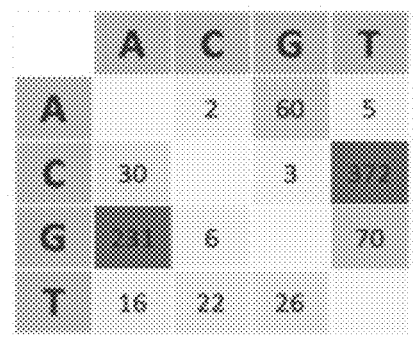
FIG. 15E is a chart showing analysis of somatic mutations detected in Pan3-edited hESCs based on base change. The majority of base changes are G to A and C to T.

Next SNVs were analyzed in these two data sets. Cas9 editing with the Pan1- and Pan3 gRNAs resulted in similar SNV patterns (FIG. 13D). The results of Pan1 showed that 2,731 (76.6%) of 3,566 UMI groups contained 10,871 SNPs, while for Pan3 8,018 (90%) of 8,870 UMI groups contained 23,477 SNVs. In both cases, the SNVs fell into two frequency ranges. Most SNVs in the high-frequency category (FIG. 13D) have been reported in the common SNP database. The low-frequency SNVs (FIG. 13D) distributed evenly in the locus and did not overlap with known SNPs, likely representing somatic mutations. There was no clear enrichment of SNVs around the cutting site, which is consistent with previous reports (Wang et al., *BMC Genomics* 19, 397 (2018)). The frequency of presumed somatic mutations for Pan1 (293 somatic mutations) and Pan3 (843 somatic mutations) is 11.6 and 14.4 per Mb, respectively, which is slightly higher than the average value (~7/Mb) reported by NGS (Martincorena et al., *Science* (New York, N.Y 348, 880-886 (2015)). The spectrum (FIGS. 13D-13E, Table 6) and VAF (FIGS. 15C-15E, Table 7) of single nucleotide substitutions were consistent with published data (Martincorena et al., *Science* (New York, N.Y 348, 880-886 (2015)).

TABLE 6

Analysis of somatic mutations detected in CRISPR-edited hESCs based on functional annotation.

| Type | Count | Percent |
|---|---|---|
| exon | 20 | 4.5% |
| intergenic | 139 | 31.5% |
| intron | 107 | 24.3% |
| transcript | 7 | 1.6% |
| upstream | 139 | 31.5% |
| UTR 5 prime | 29 | 6.6% |

TABLE 7

Analysis of somatic mutations detected in Pan3-edited hESCs based on functional annotation.

| Type | Count | Percent |
|---|---|---|
| exon | 149 | 16.2% |
| intron | 639 | 69.3% |
| splice site acceptor | 3 | 0.3% |
| transcript | 79 | 8.6% |
| UTR 3 prime | 52 | 5.6% |

Figure 14C:
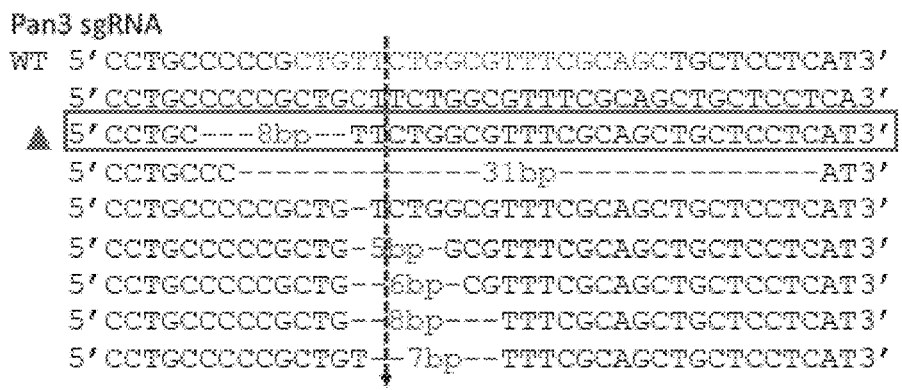

Besides SNVs and SVs, VAULT also reported many small indels around the Cas9 cleavage site. The indels were compared with the Sanger sequencing data of single-cell derived clones. The results showed that IDMseq correctly identified a subset of the deletion alleles (FIGS. 14B-14C).

In summary, IDMseq and VAULT enable quantitation and haplotyping of both small and large genetic variants at the subclonal level. They are easy to implement and compatible with all current sequencing platforms, including the portable Oxford Nanopore MinION. IDMseq provides an unbiased base-resolution characterization of on-target mutagenesis induced by CRISPR-Cas9, which could facilitate the safe use of the CRISPR technology in the clinic. The high sensitivity afforded by IDMseq and VAULT may be useful for early cancer detection using circulating tumor DNA or detection of minimal residual diseases. Results showed that IDMseq is accurate in profiling rare somatic mutations, which could aid the study of genetic heterogeneity in tumors or aging tissues. IDMseq in its current form only sequences one strand of the DNA duplex, and its performance may be further improved by sequencing both strands of the duplex.

Example 7: iMiGseq Yields Single-Cell Sequencing of Individual Mitochondrial Genome in Human and Mouse Oocytes Bi, et al., "Single-cell Individual Complete mtDNA Sequencing Uncovers Hidden Mitochondrial Heterogeneity in Human and Mouse Oocytes," *bioRxiv*, 2020.12.28.424537; doi.org/10.1101/2020.12.28.424537 (64 pages), and all of the Supplemental/Additional information associated therewith are specifically incorporated by reference herein in their entireties.

Materials and Methods
Cell Line and Human Oocytes

The 293T cell line was cultured in Gibco™ DMEM medium (high glucose) containing 10% Gibco™ Fetal Bovine Serum (heat inactivated) and 1× Gibco™ Penicillin-Streptomycin (5,000 U/mL). Cells were maintained at 37° C. in a humidified incubator with sea-level air enriched with 5% $CO_2$. All human immature oocytes were collected from the reproductive medical center in the Third Affiliated Hospital of Guangzhou Medical University. The study of human oocytes collection was approved by the Institutional Review Board (IRB) of the Third Affiliated Hospital of Guangzhou Medical University and KAUST Institutional Biosafety and Bioethics Committee (IBEC). All of the oocyte donors signed the inform consent voluntarily after they were clearly informed all of the content and details of the experiments. The women were in intracytoplasmic sperm injection (ICSI) cycles because of male infertility were involved in this study, and the immature oocytes were found after oocyte retrieval and cumulus cells removal. In general, such immature oocytes will be discarded as a medical waste and not used for the fertilization during the process of assisted reproductive technology. The endometrium tissues were donated by women with mitochondria diseases who signed the informed written consent voluntarily after learning the study aims and methods. The protocol was approved by the Institutional Review Board of Peking University Third Hospital. Endometrium tissues were collected into a 50 ml centrifuge tube with DMEM/F12 culture media (no phenol red, Invitrogen, Carlsbad, CA, USA) containing 100 U/ml penicillin and 100 µg/ml streptomycin (Invitrogen) during a routine gynecological examination. The tube with endometrial sample was put in the ice, and quickly transported to the laboratory. The endometrial tissue was rinsed using Hanks buffered salt solution (HBSS, Invitrogen) three times and minced into 1 $mm^8$ fragments. After digested with 2 mg/ml collagenase type I (Life Technologies, New York, NY, USA) for 45 minutes and DNase I for 30 min subsequently, the dissociated cellular suspension was treated with ACK lysis buffer (Life Technologies, New York, NY, USA) to remove red blood cells. The cells were then centrifuged for 200 g for 10 minutes, and resuspended using DMEM/F12 supplemented with 10% fetal bovine serum (Charcoal/Dextran Stripped, Gemini, California, USA), and plated on 35 mm dishes (Corning) at 37° C. in 5% $CO_2$ In Vitro Maturation of Human Oocytes Human immature oocytes were cultured following previous protocols including IVM basal medium, 0.075 IU/ml FSH, 0.075 IU/ml luteinizing hormone (LH), 10 ng/ml EGF, 10 ng/ml BDNF and 10 ng/ml IGF-1[54]. The oocytes expelling the first polar body were regarded as mature oocytes at metaphase II stage. Single matured ME oocyte was transferred into 0.5 ml EP tube without medium using mouth pipette and frozen in −80° C. refrigerator before further molecular analysis.

Mouse Oocyte Isolation

The animal experiments in this study were approved by the Institutional Animal Care and Use Committee (IACUC) of KAUST and the Salk institute for biological studies. The NSG and C57BL/6 mice were purchased from the Jackson Laboratory and Charles River Laboratories and kept in KAUST animal resources core lab. The NSG oocytes were collected from naturally ovulating female mice. For B6 oocytes, superovulation was induced in C57BL/6 (6 weeks) female mice by sequential intraperitoneal injection of 5 international units (IU) of pregnant mare's serum gonadotrophin (PMSG) (USBiological Life Sciences G8575A) and 5 IU of human chorionic gonadotrophin (hCG) (Sigma-Aldrich C1063) 46-48 h later. C57BL/6 mice were sacrificed 14 h after hCG injection. Oviducts were dissected from NSG mice (16-20 weeks) or from the super-ovulated C57BL/6 mice, and the oocytes were isolated by mouth pipette and washed in cold PBS. Then, the oocytes were dissociated from cumulus cells using Accutase (5-10 min RT), washed in cold PBS by pipetting up and down, transferred to PCR tubes in a small volume of PBS, and frozen at −80° C.

Derivation and Culture of h EPS Cells

To generate mitochondria diseases iPSCs, endometrium tissues fibroblast cells were transfected with a Sendai virus reprogramming kit (Life Technologies, A16517). The transfected cells were then plated onto Matrigel-coated culture dishes according to the manufacturer's instructions. The iPSCs were cultured on Matrigel-coated tissue culture dishes (ES-qualified, 13) Biosciences) with mTeSR1 (STEMCELL Technologies) at 37° C. and 5% CO2 in a humidified atmosphere incubator. The iPSCs culture medium was changed daily. The cells were passaged every 3-4 days using Accutase (Stemcell Technologies). The iPS cells conversion to EPS as previous reported[57].

ddPCR ddPCR was performed on a Bio-Rad QX200 Droplet Digital PCR System using ddPCR Supermix for Probes (No dUTP) kit (Bio-Rad, 1863024) according to manufacturer's protocols. The probes were synthesized by Integrated DNA Technologies Inc. as PrimeTime qPCR Probes. The wildtype probes were labeled as 5'HEX/ZEN/3'IBFQ, while the mutant probes were labeled by 5'FAM/ZEN/3'IBFQ. The primer/probe ratio was set as 3.6:1. For each reaction, 0.5 ng of purified 293T cell genome were used. All experiments were performed in three independent replicates, and the positive events were combined for the analysis.

Cell Lysis and DNA Purification

The 293T cells or single oocytes were pelleted by centrifuge at 200 g for 3 mins, and then lysed in 5 µl RIPA buffer (150 mM sodium chloride, 1.0% NP-40, 0.5% sodium deoxycholate, 0.1% sodium dodecyl sulfate, 50 mM Tris, pH 8.0) on ice for 15 mins. The cell lysate was diluted by adding 10 µl H$_2$O, and further purified to extract total DNA with 15 µl Beckman Coulter AMPure XP beads (A63882). Two-round of 70% ethanol washes were performed to remove detergents. The DNA was eluted in 10 µl H$_2$O to be used for the UMI labeling of mtDNA.

UMI Labeling and Amplification of mtDNA

The targeted UMI labeling of individual mtDNA was achieved by mtDNA specific UMI oligos. The oligos were selected to enable the efficient amplification of full-length human or mouse mitochondrial genomes. A 5' universal primer sequence and middle UMI sequence were added to the five-prime end of mtDNA specific oligos to form UMI oligos.

| Primer | Sequence | SEQ ID NO. |
|---|---|---|
| Universal primer | CATCTTACGATTACGCCAACCACT | 1 |
| mouse UMI primer | CATCTTACGATTACGCCAACCACT GCGGNNNNNTGNNNNNCCTCCACG AAACAGGATCAAACAACC | 18 |
| mouse reverse primer | ATTGCTAGGGCCGCGATAATAAAT GGTA | 19 |
| 293 UMI primer | CATCTTACGATTACGCCAACCACT GCGGNNNNNTGNNNNNCGCCTGCC TGATCCTCCAAATCAC | 20 |
| 293 reverse primer | TGAGCCGAAGTTTCATCATGCGGA GA | 21 |
| hOO UMI primer | CATCTTACGATTACGCCAACCACT GNNNNNTGNNNNNTAACAACATAC CCATGGCCAACCT | 22 |
| hOO reverse primer | AGTTTTATGCGATTACCGGGCTCT | 23 |

A screen of DNA polymerase was performed to ensure the high efficiency in the UMI labeling and PCR amplification.

The UMI labeling reaction is set up as follows: 10 µl purified DNA, 2.5 µl UMI oligos (10 µM), 12.5 µl 2× Platinum™ SuperFi™ PCR Master Mix (Invitrogen, 12358010). The reaction was incubated on a thermocycler with a ramp rate of 1° C. per second using the following program: 98° C. 1 min, 70° C. 5 s, 69° C. 5 s, 68° C. 5 s, 67° C. 5 s, 66° C. 5 s, 65° C. 5 s, 72° C. 10 min, 4° C. hold. After UMI labeling DNA is purified by 0.8×AMPure XP beads, washed twice by 70% ethanol and eluted 10 µl H$_2$O. The universal primer and mtDNA specific reverse primer were used to amplify only the UMI labeled mtDNA. The 50 µl PCR reaction contains 1.25 U PrimeSTAR GXL DNA Polymerase (Takara, R050), 1× PrimeSTAR GXL Buffer, 200 µM dNTP mixture, 0.2 µM each primer, and 10 µl of purified UMI-labeled DNA. The thermocycler program is set as follows: 95° C. 1 min, (98° C. 10 s, 68° C. 14 min, 30 cycles), 68° C. 5 min, 4° C. hold. The amplicon was validated by agarose gel electrophoresis. If a specific DNA band was observed, the rest DNA will be purified by 0.8× AMPure XP beads. A second round of PCR amplification for 15-20 cycles with PrimeSTAR GXL DNA Polymerase could be performed to obtain enough DNA for sequencing.

Whether or not the variant calling results could be affected by PCR artifacts, which is the main source of errors in UMI consensus sequencing originating from polymerase replication error in the barcoding step was considered (Filges et al., Scientific reports 9, 3503 (2019)). The Platinum SuperFi DNA polymerase used has the highest reported fidelity (>300× that of Taq polymerase), and meanwhile captures twice more molecules in the library than Taq (see Examples above, and Bi, et al., Genome biology 21, 213, doi:10.1186/s13059-020-02143-8 (2020)). Theoretically, this polymerase introduces one error in ~1,600 unique 16556-bp molecules in the UMI labeling step. Accordingly, this type of inescapable error is expected to be around 1 in 1,600 UMI groups, thus representing a minor fraction of the observed SNVs.

Library Preparation and Sequencing

For Nanopore sequencing, library preparations were done using the ligation sequencing kit (Oxford Nanopore Technologies, SQK-LSK109). The sequencing runs were performed on an Oxford Nanopore MinION sequencer using R9.4.1 flow cells. Base calling of Nanopore reads was done using the official basecaller termed Guppy (v3.2.1). For PacBio sequencing, library preparations were done using the Sequel Sequencing Kit 3.0. The sequencing runs were performed by the BIOPIC core facility at Peking university (Beijing, China) on the PacBio Sequel with SMRT Cell 1M v3 LR Tray. HiFi Reads were generated by the official tool termed ccs (v3.4.1). All procedures were preformed according to manufacturer's protocols.

Bioinformatic Analysis

All iMiGseq data were analyzed by VAULT with —unmapped_reads and—group_filter options, to remove unmapped reads before UMI analysis and filter out low-confidence UMI groups after variants calling. For Nanopore data, the error tolerance threshold—error in UMI identification was set to 0.11, while for PacBio CCS data, it was set to 0.05. Only prefect UMIs with correct length and structure (NNNNNTGNNNNN (SEQ ID NO:24)) were subjected to downstream analysis. The SNV calling and filter were performed using default parameters of VAULT, and involved in Samtools v1.9[47]. SNVs in primer regions were filtered out before downstream analysis.

The reference sequence—refer used in VAULT analysis was the designed amplicon sequence, which is based on CM004185.1 for NOD oocytes, NC_005089 for B6 oocytes, and NC_012920 for 293T cells and human oocytes. This gave rise to a different coordinate to the canonical mitochondria reference genome. The vault position command was used to revise the DNA coordinate and reference chromosome name in VCF files, to enable further functional analysis by SnpEff v4.3[48]. In the SNV annotation, the positions of SNVs in NOD oocytes were converted to the corresponding coordinates of B6 mouse strain. GRCm38.86 database of SnpEff was used in mouse SNV annotation, while hg38 kg database was used for human SNVs.

The SV calling of VAULT utilized minimap2.1[49] and sniffles v1.0.11[50]. The detected SVs were first filtered by variant allele frequency of 0.6 and then manually checked. This SV calling pipeline had been validated in the original work of VAULT[3]. However, in this study large SVs (≥35 bp) were not detected from mtDNA of healthy samples. The consensus sequence of high coverage UMI groups was called using vault consensus command. It utilized canu v2.0[51] to do de novo assembly, and the Nanopore official tool medata v0.12.1 to polish the assembled sequence. Most UMI groups failed to generate contigs in canu assembly, thus lead to a reduction of assembled mtDNA. Further assemblers with improved performance could potentially solve this problem and lead to more assembled mtDNA.

The synonymous and nonsynonymous sites of mouse mitochondrial genome was calculated using the pS_pN_count tool of VAULT, and based on the Nei-Gojobori method[52]. The dN/dS ratio was calculated using bash command based on the Nei-Gojobori method. The mutational spectrum was analyzed using SomaticSignatures[53].

SNV allele frequency (VAF, also mentioned as NHL) is calculated as

UMI group number with this SNV/effective UMI group number at this position

Effective UMI group number is defined as the number of UMI groups with depth ≥3 at the position of this SNV.

SNV number per genome is calculated as

SNV number in UMI group/surveyed length(depth ≥3)in that group*genome length.

Data and Materials Availability

VAULT and sample data in this study are accessible at GitHub (github.com/milesjor/vault).

Validate iMiGseq Using 293T Cells iMiGseq of individual mtDNA in HEK 293T cells was tested. IMiGseq relies on long reads to cover both UMI and the whole mitochondrial genome. The sequencing technology should offer both ultra-long reads (~16.5 kb) and low sequencing error. Thus, two state-of-the-art long-read platforms-Oxford Nanopore MinION and PacBio Sequel were tested. Quantitative PCR showed that the 293T cell line contains on average 1.5 k mtDNA per cell FIG. 16C). Five 293T cells were obtained by serial dilutions, visually verified, and subsequently subjected to DNA purification and UMI labeling of full-length mtDNA (FIG. 16B).

Figure 16D:
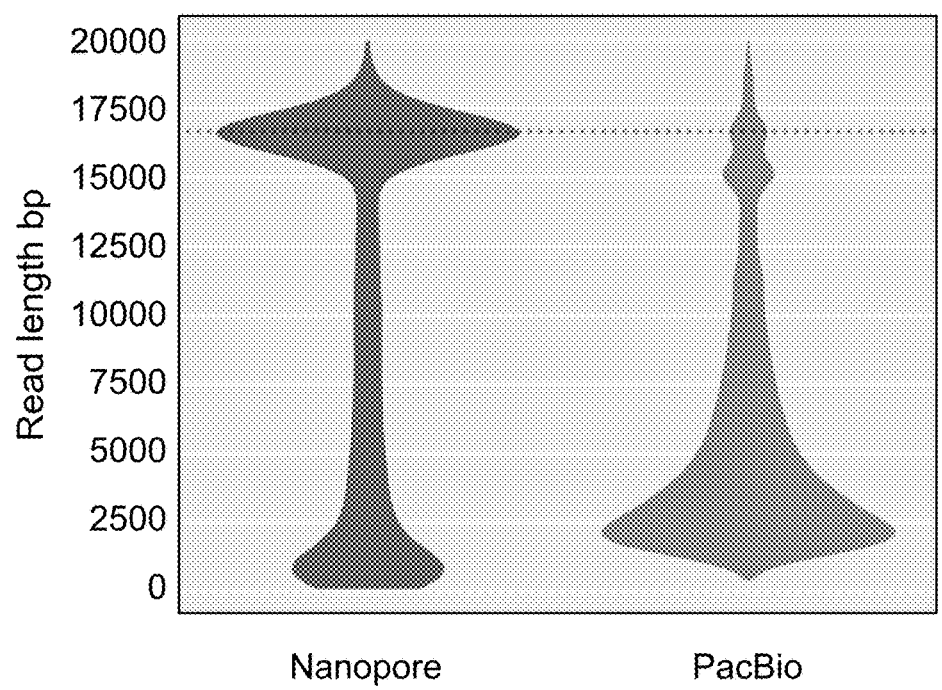
FIG. 16D shows comparison of read length distribution in iMiGseq of 293T cells on the Nanopore and PacBio platforms. The dotted line represents the size of the human mtDNA.
Figure 17A:
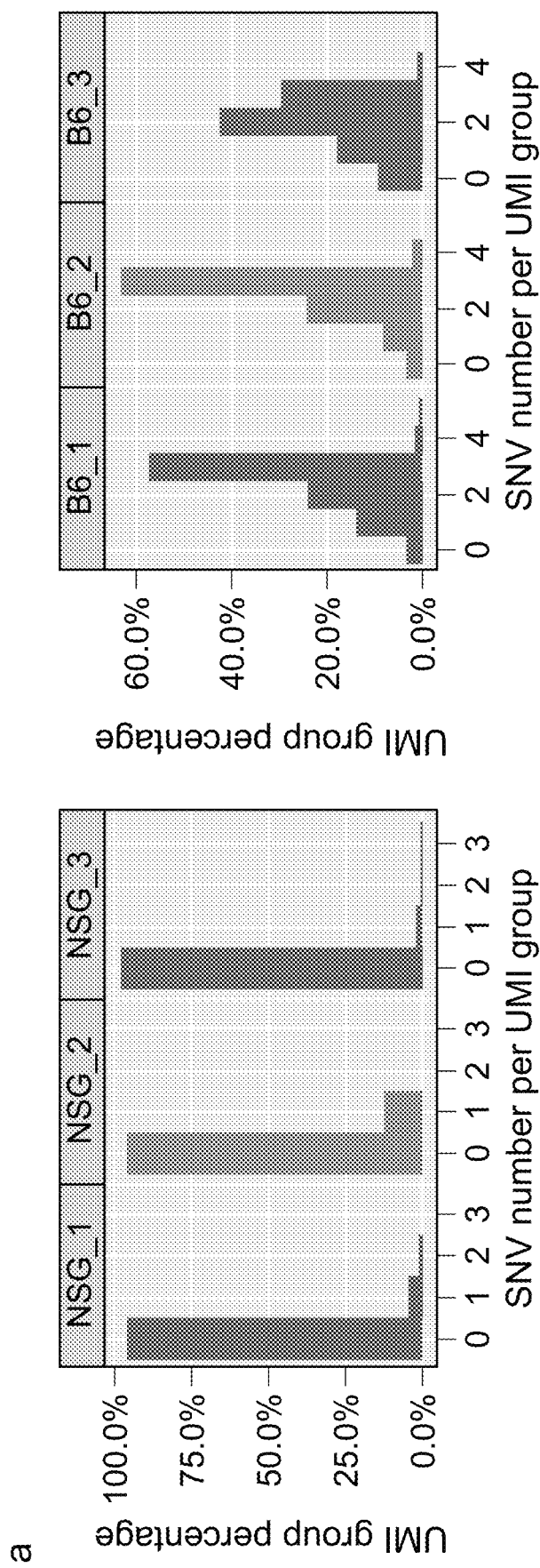
FIG. 17A is a histogram of SNV load per mtDNA in the three NSG (left) and B6 (right) mouse oocytes. The three oocytes of the same strain show a similar pattern of SNV load.

Nanopore sequencing generated 81.8 k reads, of which 26.4% contained high-confidence UMI sequences (Table 9, FIG. 16D, FIG. 17A).

TABLE 9

Summary of individual sequencing runs

| Sample | Mapped Read count | Reads with UMI | Detected mtDNA (with ≥5 reads) | mtDNA with SNV | SNV count | Median covered region of UMI groups | high coverage mtDNA* | Average SNV load per mtDNA | unique SNV number | somatic SNV (<0.01 VAF)* | somatic SNV load per mb* | mtDNA with SV | Assembled full-length mtDNA genome* |
|---|---|---|---|---|---|---|---|---|---|---|---|---|---|
| 293T Nanopore | 81,798 | 21,635 | 426 | 426 | 8,986 | 16546 | 390 | 21.72 | 88 | 64 | 9.9 | 0 | 11 |
| 293T PacBio | 166,194 | 51,096 | 637 | 637 | 9,368 | 7510 | 0 | N/A | 57 | N/A | N/A | 0 | N/A |
| NSG mouse oocyte 2 | 1,086,723 | 245,363 | 4,078 | 175 | 182 | 10494 | 1322 | 0.05 | 85 | 47 | 2.2 | 0 | 103 |
| NSG mouse oocyte 2 | 959,528 | 193,793 | 1,165 | 131 | 134 | 15704 | 596 | 0.13 | 44 | 36 | 3.7 | 0 | 158 |
| NSG mouse oocyte 3 | 1,992,516 | 612,227 | 19,697 | 225 | 237 | 5562 | 4384 | 0.03 | 98 | 117 | 1.7 | 0 | 276 |
| B6 mouse oocycte 2 | 988,865 | 200,174 | 2,493 | 1,173 | 2,145 | 7782 | 436 | 2.44 | 44 | 14 | 2.0 | 0 | 41 |
| N6 mouse oocyte 2 | 549,736 | 116,430 | 1,849 | 945 | 1,818 | 8573 | 363 | 2.57 | 40 | 13 | 2.2 | 0 | 36 |
| B6 mouse oocyte 3 | 325,899 | 63.039 | 615 | 329 | 557 | 9926 | 129 | 1.97 | 14 | 2 | 1.0 | 0 | 4 |
| Human oocyte 1 | 763,582 | 95,387 | 2,308 | 2,301 | 75,483 | 16531 | 2072 | 34.80 | 141 | 128 | 3.7 | 0 | 125 |
| Human oocype 2 | 397,426 | 64,646 | 1,461 | 1,457 | 32,276 | 16413 | 1009 | 27.30 | 81 | 59 | 3.6 | 0 | 81 |
| Human oocyte 3 | 506,082 | 99,404 | 1,535 | 1,514 | 22,522 | 15568 | 712 | 23.00 | 69 | 20 | 1.7 | 0 | 46 |
| hEPS$^{m.8993T>C}$ | 72,496 | 34,959 | 536 | 536 | 12,173 | 16,573 | 515 | 23.19 | 117 | 72 | 8.5 | | |

*data analyzed using extensive-coverage UMI groups

Results

IMiGseq applied the IDMseq strategy to label each mtDNA in single cells with a unique molecular identifier (UMI, FIG. 16A). IDMseq had been proved to enable base-resolution haplotype-resolved quantitative characterization of diverse types of rare variants[3]. In iMiGseq, UMI-labeled mtDNA will be further amplified by high-fidelity long-range PCR (FIG. 16A). The sequencing is performed on third-generation long-read sequencing platforms to obtain full-length mtDNA reads with UMIs. The sequencing data are analyzed by the bioinformatic toolkit termed VAULT[3], to generate variant details and assemble the genome for individual mtDNA (FIG. 16B). The key components of iMiGseq, IDMseq and VAULT have been validated to be able to overcome the raw base calling errors of long-read sequencing through error correction by the molecular consensus strategy thus enabling sensitive detection of diverse classes of genetic variants[3]. The design of iMiGseq further eliminated the influence of NUMT contaminations that perplexed the current NGS-based analysis of mtDNA variants (see methods).

The low percentage of reads with UMI is potentially due to base calling errors in the UMI region and/or DNA fragmentation during library preparation and sequencing. The reads were assigned to 542 UMI groups (a set of reads sharing the same UMI), of which 92.6% covered more than 95% of the entire mtDNA and the median covered length is 16556 bp (position with depth ≥3, FIG. 16E). After further filtering based on in-group read consistency (see methods), 426 high-confidence UMI groups were obtained, of which 390 covered ≥95% of the mtDNA, which represented 390 individual complete mitochondrial genomes. Variant analysis by VAULT showed that 426 UMI groups contained a total of 8986 high-confidence single nucleotide variants (SNVs). No structural variants (SVs) were detected. The variant allelic frequencies (VAFs) of SNVs (see methods) ranged from 0.23% to 96.47% (FIGS. 16F & 16G). Functional annotation showed that 24.11% of SNVs were missense variants and high frequency SNVs were enriched in the CYTB gene and D-loop region (FIG. 16F). Based on the number of detected SNVs in each UMI group, the distribution of SNV load (number of SNVs per genome, calculation in methods) among the individual mtDNA were plotted (FIG. 16H). The major base changes were A>G (T>C) and C>T (G>A) (FIG. 16I), which were consistent with previous reports[26, 28, 30] and significantly different from somatic mutation in the nuclear genome. Consensus mtDNA sequences were assembled using reads in extensive-coverage (covering >95% of the entire mtDNA with depth ≥3) UMI groups, and due to limitations of the assembler (see methods) 11 full-length mtDNA were obtained from 390 UMI groups. All of the 11 mtDNA were placed into the U5a1 mitochondrial haplogroup by MITOMASTER[31] (mitomap.org), which fit the Dutch origin of 293 cells[32]

Figure 16E:
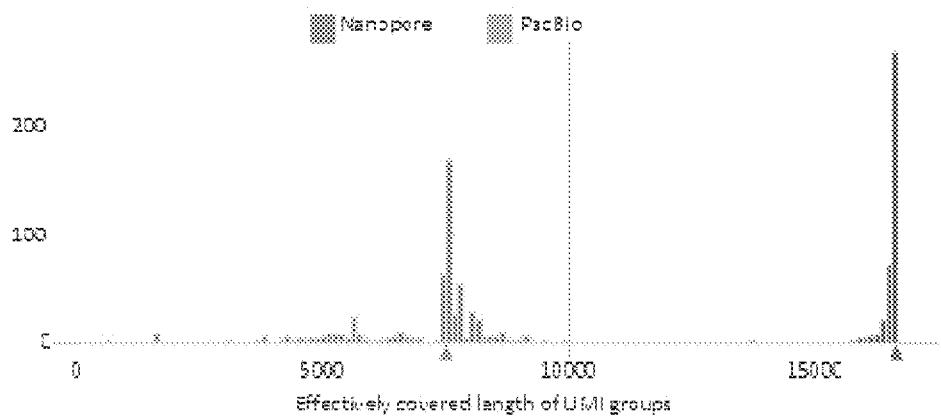
FIG. 16E shows distribution of effectively covered length of UMI groups detected by Nanopore and PacBio sequencing. N50 of either sequencing technology is indicated as triangles on the X-axis.
Figure 16F:
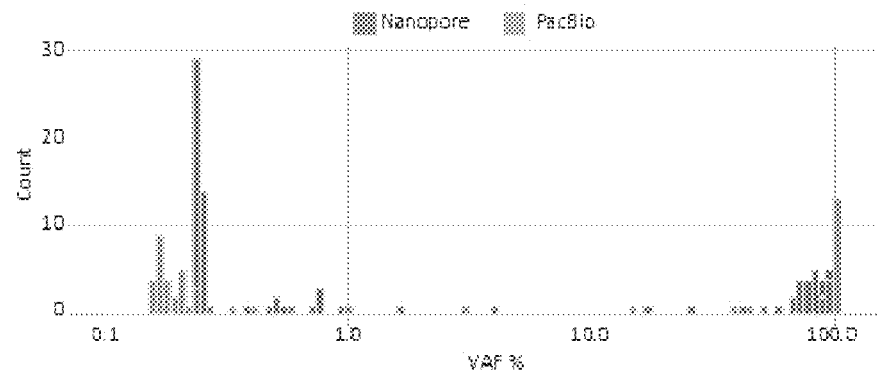
FIG. 16F shows VAF distribution of SNVs detected in iMiGseq of 293T cells. The SNVs fall into two VAF ranges in both Nanopore and PacBio data. High-frequency SNVs have VAFs greater than 60%, while low-frequency SNVs have VAFs less than 1%.
Figure 16G:
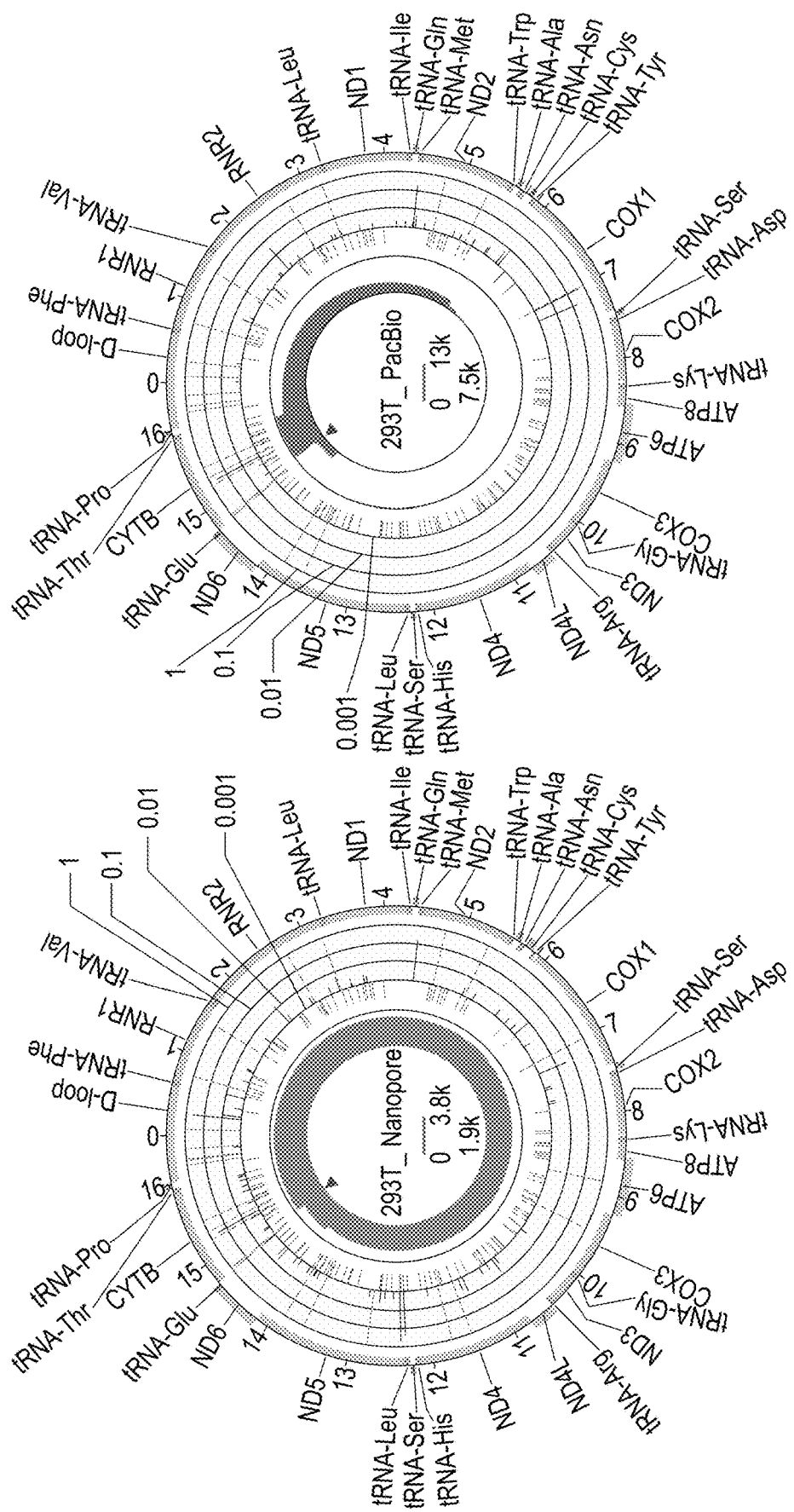
FIG. 16G is circular plots showing the distribution of SNVs in the mitochondrial genome of 293T cells determined by Nanopore and PacBio sequencing. The innermost circle (grey) shows the depth of reads of all detected UMI groups in linear scale as indicated by the scale bar in the center. The red triangle indicates the position of the primers. The middle circle (light blue) represents common SNPs from the human dbSNP-151 database. Individual SNVs are plotted in the outer barplot circle, in which the height of bar represents the VAF. Red color indicates VAF>0.6. The outermost circle is a color-coded diagram of the human mtDNA. Blue: protein-coding genes. Yellow: rRNA genes. Dark green: tRNA genes. Light green: D-loop.
Figure 16H:
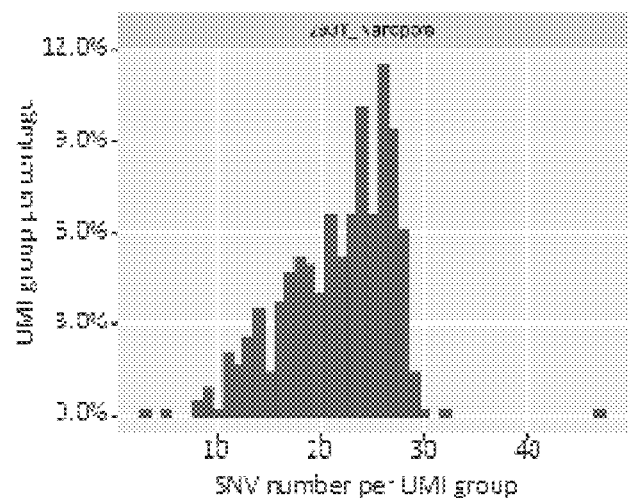
FIG. 16H is a histogram of SNV load per mtDNA in 293T cells based on Nanopore iMiGseq.
Figure 16I:
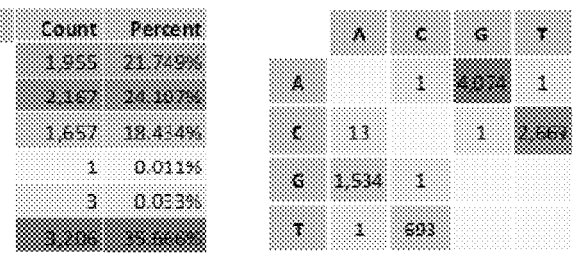
FIG. 16I shows analysis of SNVs detected by Nanopore iMiGseq based on functional annotation and base change. The majority of base changes are A>G (T>C) and C>T (G>A).

PacBio sequencing generated 637 high-confidence UMI groups from 166 k reads, of which none covered more than 95% of the full length of mtDNA (Table 10, FIG. 16E). The median covered length was 7510 bp, less than half of that of Nanopore sequencing. The same pipeline was applied to filter out low-confidence UMI groups and perform variant calling. There were 637 high-confidence UMI groups containing 9368 SNVs with frequencies from 0.16% to 100.00% (FIG. 16F). All of the high frequency SNVs (VAF ≥0.6) existed in the Nanopore data, and of them had been reported as common SNPs in the human dbSNP-151 database, thus cross-validating these called variants (FIG. 16G). Only 10.53% of low frequency SNVs were in the Nanopore data. Consistent with the Nanopore data, the major base changes were A>G (T>C) and C>T (G>A). Importantly, the mutation signatures were highly consistent between the PacBio and Nanopore data, and showed no evidence of artifactual mutations in homopolymer regions, which were purported to be more error prone in Nanopore sequencing (FIG. 19B). Unlike the Nanopore data that supported de novo assembly of mitochondrial genomes, the PacBio data resulted in none (Table 9). Because Nanopore sequencing showed high concordance with the PacBio data, which had low raw sequencing error, and PacBio struggled in generating sufficiently long reads to cover the whole mtDNA, it was concluded that Nanopore was better suited for iMiGseq, at least under these conditions.

Figure 16J:
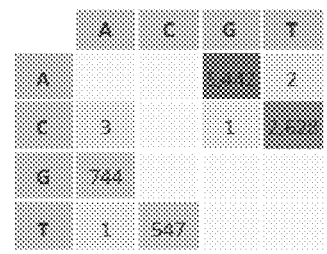
FIG. 16J is similar to 16C but for PacBio iMiGseq data.

All of the PacBio high-frequency SNVs (VAF ≥0.6) existed in the Nanopore data, and all of them are common SNPs (dbSNP-151), thus cross-validating these called variants (FIG. 16G). Importantly, the mutational spectra and signatures were highly consistent between the PacBio and Nanopore data, and showed no evidence of artifactual mutations in homopolymer regions, which were purported to be more error-prone in Nanopore sequencing (FIG. 19B, 16J). These data indicate the variants identified by Nanopore iMiGseq are of high confidence.

Figure 16K:
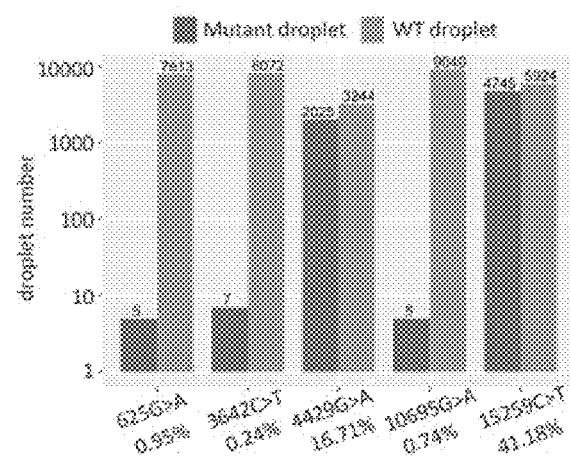
FIG. 16K is a bar graph showing ddPCR results showing the detected events (droplets) for variants with different VAFs. The VAFs calculated by Nanopore iMiGseq are shown under the variants. Around 80 cells were used in ddPCR to ensure the generation of enough events for analysis, as compared to 5 cells in iMiGseq.

The extent of false-positive variants due to polymerase replication error in the barcoding step (the main source of errors in UMI consensus sequencing (Filges et al., *Scientific reports* 9, 3503 (2019)) were examined and it was determined that this type of error introduced roughly 1 mutation in 1,600 labeled full-length mtDNA (see methods, see Examples above, and Bi, et al., *Genome biology* 21, 213, doi:10.1186/s13059-020-02143-8 (2020)), thus representing a miniscule fraction of the SNVs (0.004% in the Nanopore iMiGseq). To further validate the ultra-rare variants detected by iMiGseq, digital droplet PCR (ddPCR) assays were preformed for five SNVs representing a wide range of VAFs (0.24% to 41.18%) in the Nanopore iMiGseq data. The three rare SNVs with a VAF<1% (detected in one UMI group) were confirmed by ddPCR (FIG. 16K). The VAFs obtained by ddPCR were comparable to iMiGseq. The two high-frequency SNVs showed consistent VAFs in the iMiGseq by Nanopore and PacBio (m.4429G>A, 16.71% in Nanopore and 15.08% in PacBio; m.15259C>T, 41.18% in Nanopore and 39.12% in PacBio), and were further validated by ddPCR (m.4429G>A, 38.29%; m.15259C>T, 44.46%, FIG. 16K). It is worth noting that the difference in the VAF of m.4429G>A between iMiGseq and ddPCR is potentially due to the different population of cells in the experiments and heterogeneity of mtDNA in 293T cells.

Because Nanopore sequencing showed high concordance with PacBio CCS, which rivalled Illumina NGS in accuracy[55] (FIG. 16D), and PacBio failed to generate sufficiently long reads to cover the whole mtDNA, we concluded that Nanopore-based iMiGseq could produce highly accurate and complete mtDNA sequences. These results provided a quantitative analysis of the genetic heterogeneity of mitochondria in human cells beyond the analysis of individual SNVs to include the linkage between SNVs in the mitochondrial genome for the first time.

These results provided a quantitative analysis of the genetic heterogeneity of mitochondria in human cells beyond the analysis of individual SNVs to include the linkage between SNVs in the haploid mitochondrial genome for the first time.

iMiGseq of NSG and B6 Mouse Oocytes

Figure 17B:
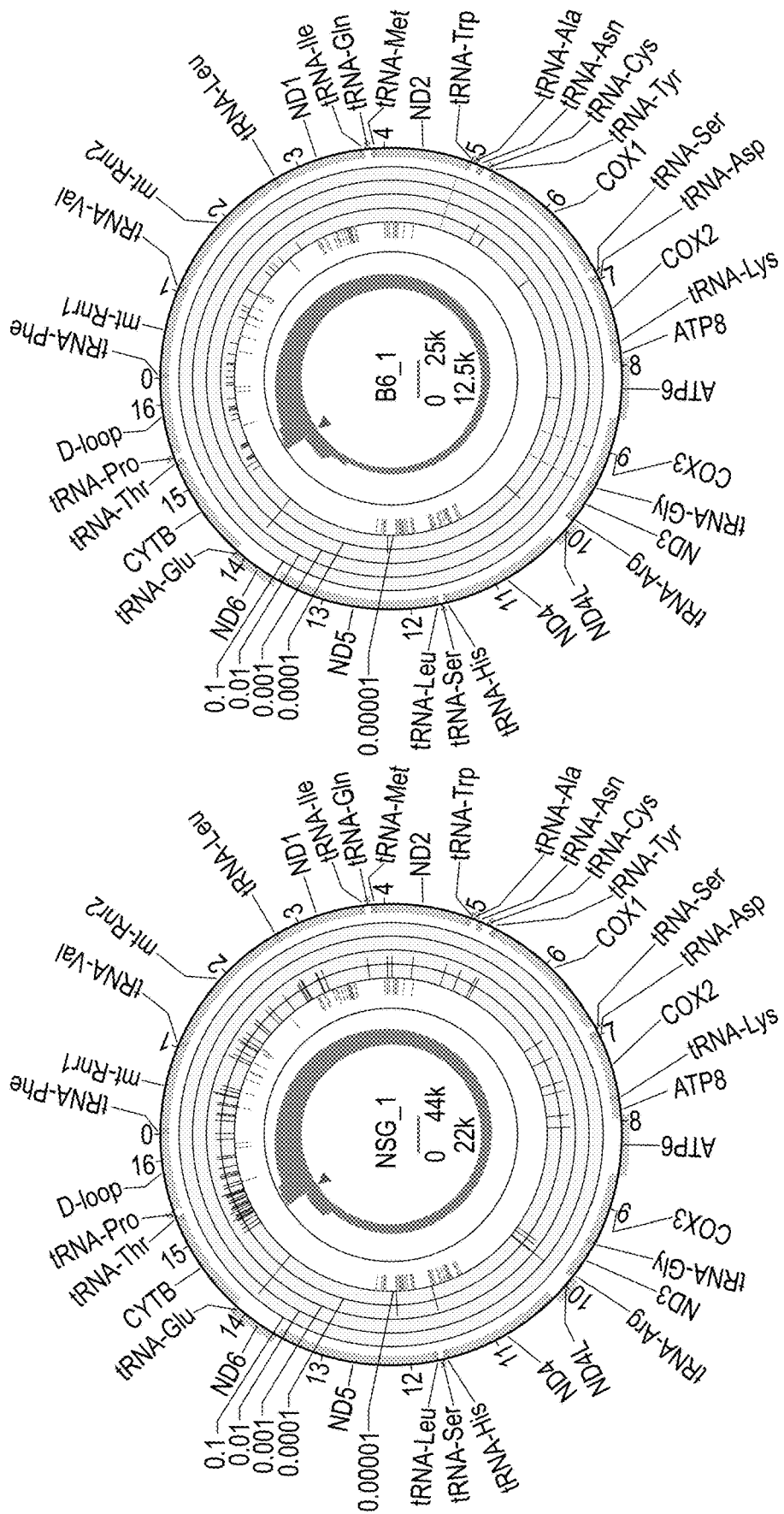
FIG. 17B are circular plots showing the distribution of SNVs in the mitochondrial genome of the three NSG (left) and B6 (right) mouse oocytes. The arrangement of the circular plots is similar to FIG. 1e, except that the middle circle (light blue) represents the common SNPs from the mouse dbSNP-142 database.
Figure 17C:
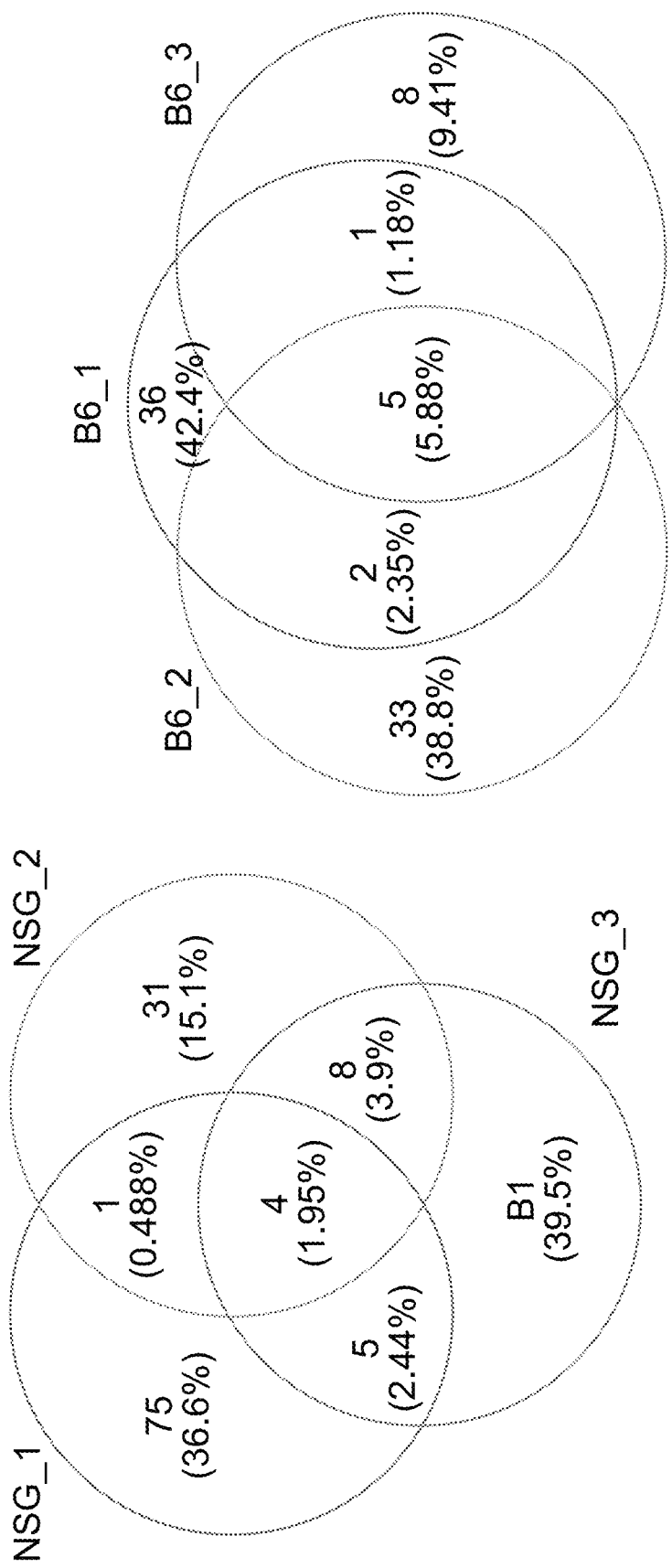
FIG. 17C is Venn diagrams showing the overlap of mtDNA SNVs detected in the three NSG (left) and B6 (right) mouse oocytes.
Figure 17F:
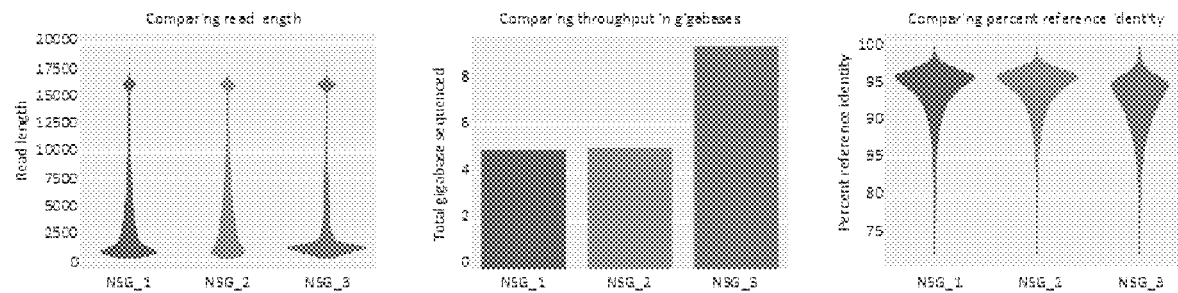
FIG. 17F is a comparison of read length, throughput and percent reference identity of reads in the NSG mouse oocyte sequencing.
Figure 18A:
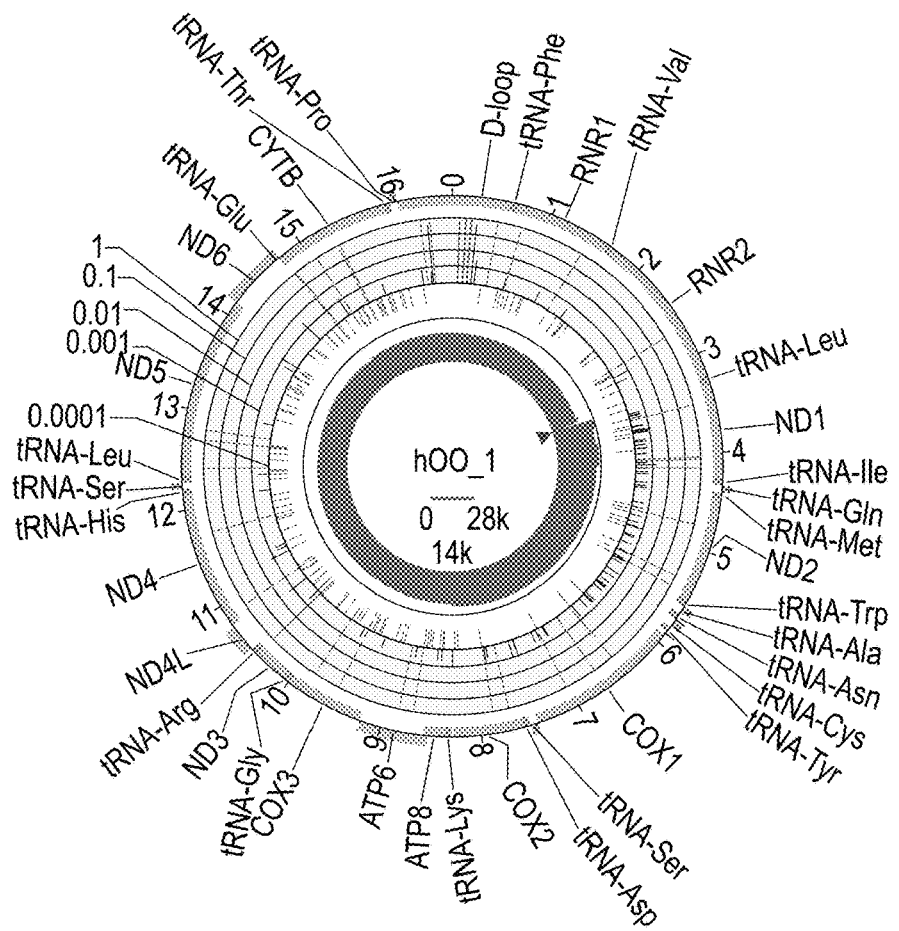
FIG. 18A is circular plots showing the distribution of SNVs in the mitochondrial genome of hOO_1. The arrangement of the circular plots is similar to FIG. 16E.
Figure 18B:
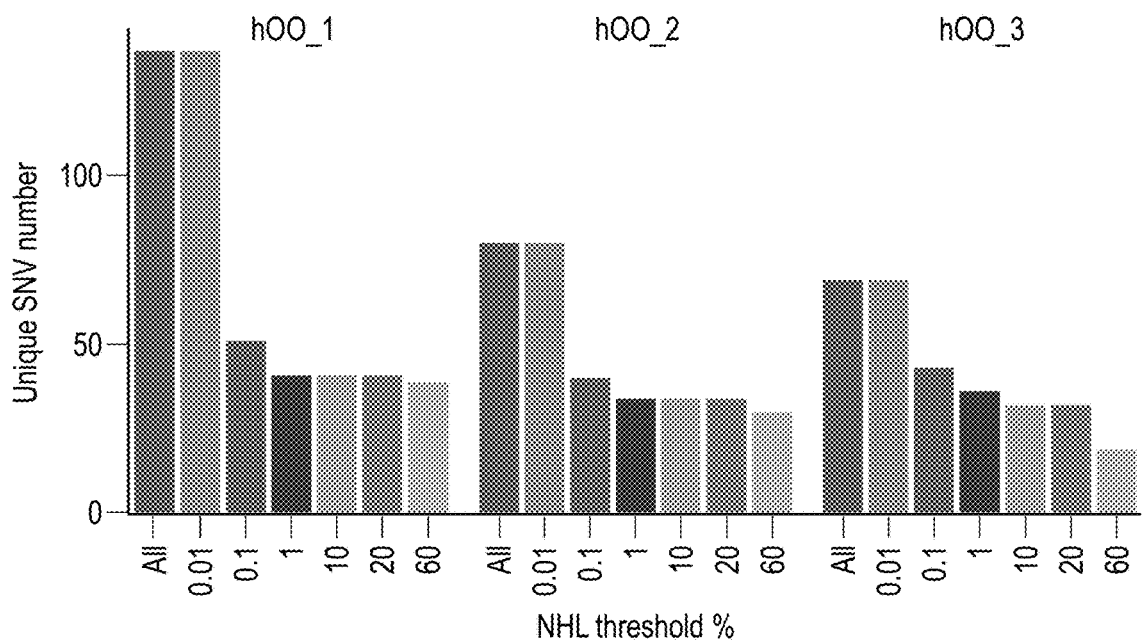
FIG. 18B shows unique SNV number above different heteroplasmy threshold. For all three hOOs, a significant amount of unique SNVs had an NHL below the 1% detection limit of current methods.
Figure 18C:
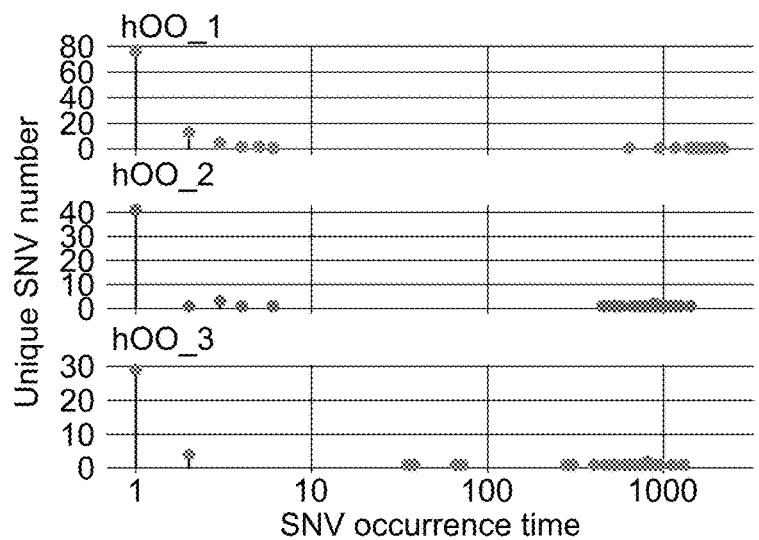
FIG. 18C shows the occurrence time of unique SNVs detected in iMiGseq of human oocytes. Most of the unique SNVs appear one time (exist in one UMI group).
Figure 18D:
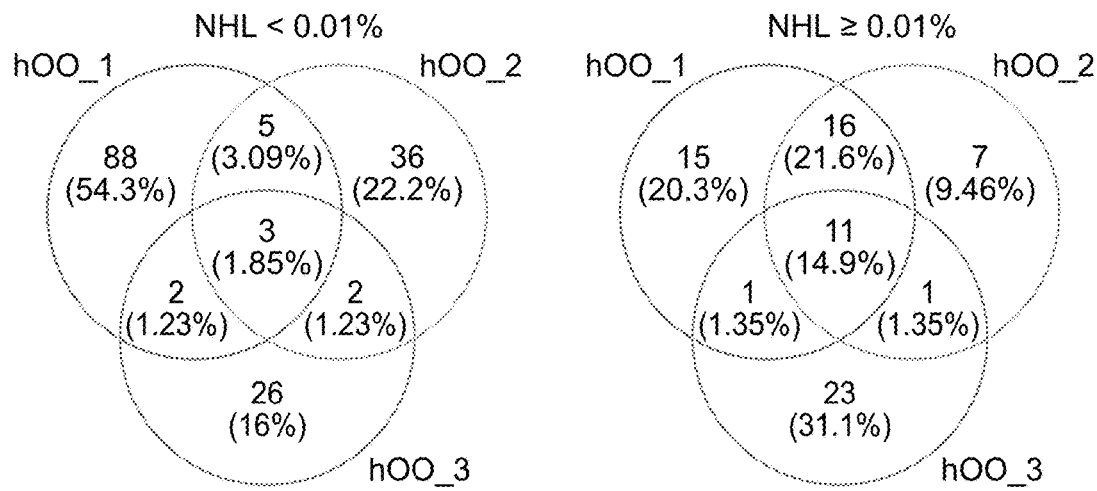
FIG. 18D, is Venn diagrams showing the overlap of mtDNA SNVs between the hOOs at different heteroplasmy levels. A higher proportion of SNVs with an NHL≥0.01 (right) were shared among hOOs than those with an NHL<0.01 (left).

Experimental data and population genetics modeling indicate that heteroplasmies arisen in mature oocytes strongly influence the inheritance of mtDNA mutations in the offspring[7, 8]. Yet, many key questions remain unanswered, such as whether the ostensibly somatic mutations found in old individuals originate from low-level heteroplasmic mutations in the oocyte or de novo mutations. Experiments were designed to test if iMiGseq may provide a quantitative understanding of the genetics of mtDNA in oocytes.

iMiGseq was applied to single oocytes of the NOD-scid IL2Rgamma$^{null}$ (NSG) and C57BL/6 (B6) mouse strains. Three oocytes from one female per strain were sequenced. Each oocyte was subjected to the same iMiGseq protocol to extract and label mtDNA and sequenced in one flow cell on the MinION. The three NSG oocytes generated 1.09, 0.96 and 1.99 million reads, which led to 4078, 1165 and 19697 high-confidence UMI groups, respectively (Table 9, FIG. 17F). VAULT analysis based on the NSG mouse reference genome (GenBank: CM004185.1) identified 182, 134 and 237 SNVs from oocytes NSG_1, NSG_2 and NSG_3, respectively. No large SV was detected. SNV load per mitochondrial genome were calculated using extensive-coverage UMI groups. The results showed that the vast majority of the mtDNA in the three NSG oocytes contained no variant, which fit the expectation of a homogenous female germ line resulted from extensive backcrosses to an inbred strain (Table 9, FIG. 17A). Most SNVs had a nominal heteroplasmy level (NHL, no. of UMI groups with SNV/no. of UMI groups with ≥3 coverage in the SNV position) less than 1%, which is incidentally the detection limit of most published studies[8, 24-26] (FIG. 17B, FIG. 18H). It is worth noting that the NHL of the rarest SNVs (e.g. appear in 1 UMI group) tends to be more affected by sequencing depth and may not be accurate. Interestingly, the three oocytes shared a very small fraction of the SNVs despite being from the same female (FIG. 17C), and the shared SNVs tended to have high maximum occurrence times (no. of times a SNV is discovered in a UMI group). For example, the m.1442A>G, m.5421G>A, and m.14027C>A variants, shared by all three oocytes, had maximum occurrence of 40, 30, and 66, respectively, as opposed to the median of 1. These observations were consistent with an independent germline bottleneck in oocyte Lineages7.

Figure 17D:
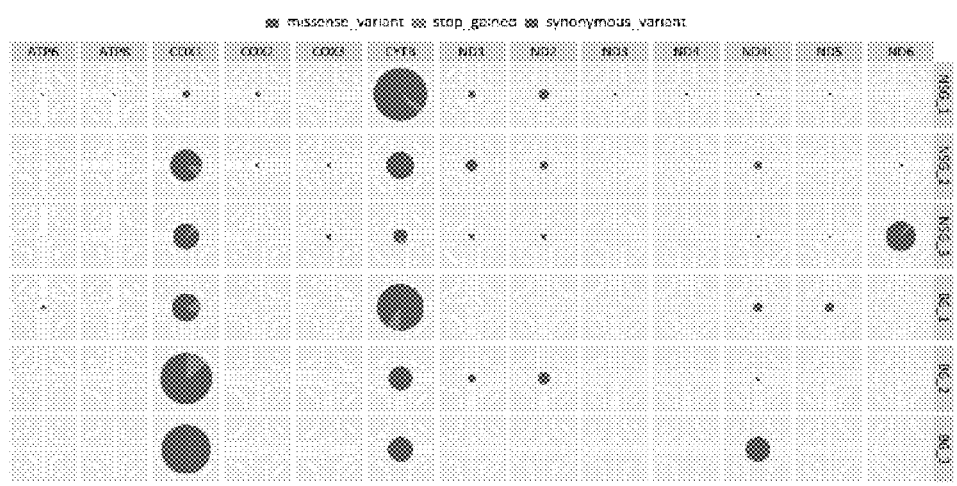
FIG. 17D shows functional annotation of SNVs in protein-coding regions detected by iMiGseq of single mouse oocytes. The size of the pie chart is proportional to overall mutation frequency, and the color corresponds to the type of mutation. Variants called in all UMI groups (not limited to extensive-coverage groups) were used to generate this plot.
Figure 17E:
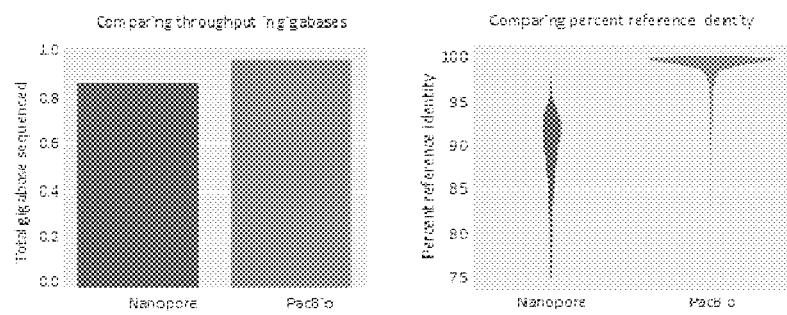
FIG. 17E is a comparison of throughput and percent reference identity of reads in the 293T sequencing by Nanopore and PacBio sequencers. PacBio ccs reads have a higher accuracy than Nanopore 1D reads.

Functional annotation showed that deleterious SNVs (missense and stop-gained variants) affecting amino acid sequence were prevalent among heteroplasmic SNVs and accounted for 64.13%, 17.17% and 51.06% of SNVs discovered in NSG_1, NSG_2 and NSG_3, respectively (FIG. 18I). These heteroplasmic mutations were enriched in the Cox1, Cytb and Nd6 genes (FIG. 17D).

Figure 17G:
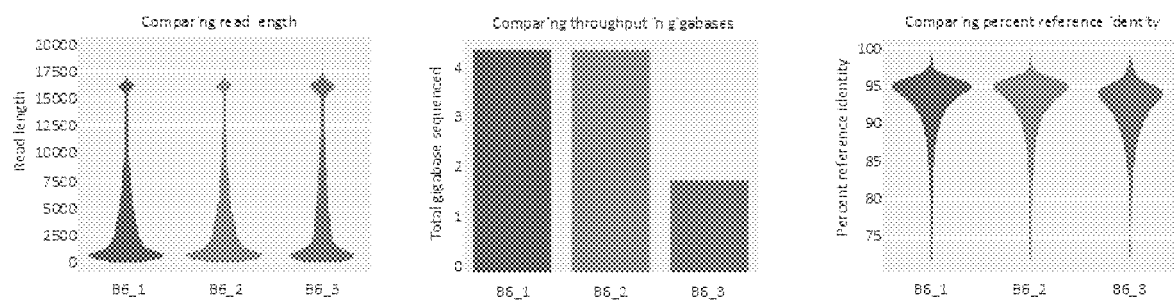
FIG. 17G and FIG. 17H, are similar to FIG. 17F but for the B6 mouse oocyte and human oocyte sequencing, respectively.

Similarly, individual mtDNA sequences were obtained from three oocytes from one female of the B6 inbred strain (Table 9, FIG. 17G). Variants were called using the NC_005089 reference genome, and their NHL ranged from 0.04% to 72.82% (FIG. 17B, FIG. 19E). Again, SV was not observed. As seen in the NSG data, only 5 (5.88%) SNVs were shared among the B6 oocytes (FIG. 17B). The distribution of SNVs in extensive-coverage UMI groups showed that the majority of mtDNA in the three oocytes contain three high frequency SNVs (FIG. 17A), i.e., m.4891T>C, m.9027G>A and m.9461T>C (NHL 42.80% to 72.82%), of which m.9027G>A caused a glycine to serine mutation in codon 141 of the COX3 gene, while the other two were synonymous. The three SNVs were not in the mouse common SNP database (dbSNP-142), but were reported in a previous study[33]. Like in NSG oocytes, deleterious SNVs in protein-coding sequences were prevalent among heteroplasmic SNVs (23.96% for B6_1, 24.20% for B6_2, 20.29% for B6_3, respectively) in wild-type B6 oocytes (FIG. 19F). Most low-frequency SNVs existed in solo UMI groups, however, several reoccurred in multiple UMI groups and/or oocytes, such as m.14027C>A (p.Gly15Val, in B6_1), m.10102G>A (p.Ala76Thr, in all oocytes) and m.5421G>A (p.Ala32Thr, in all oocytes).

Figure 17H:
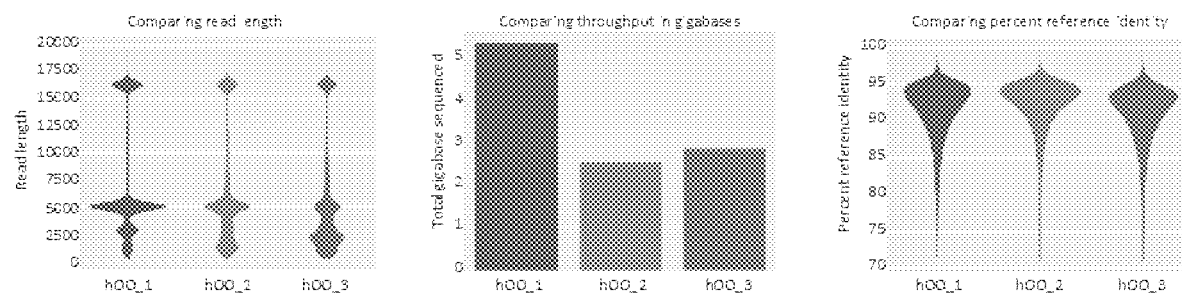
Figure 17I:
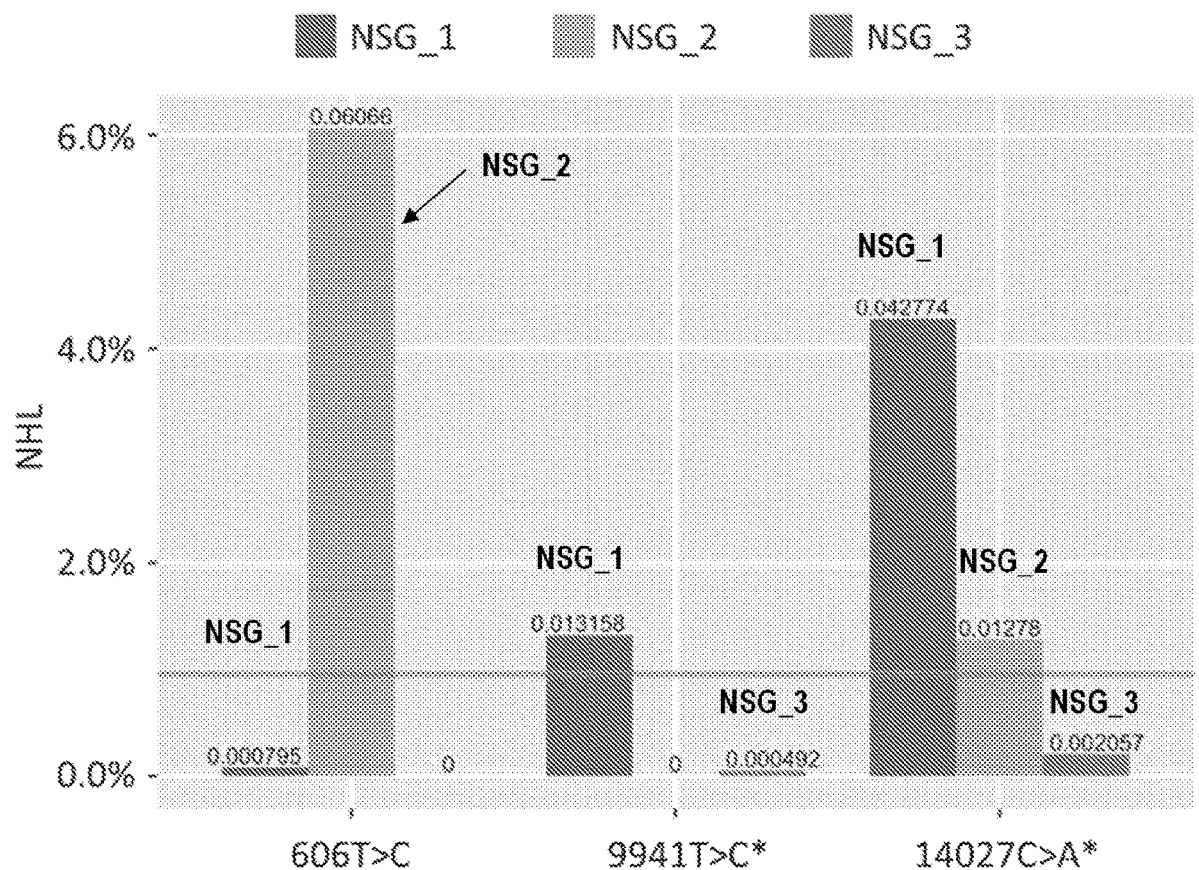
FIG. 17I is a bar graph showing comparison of common SNVs in the three NSG oocytes. * indicates detrimental variant. The detection limit of current NSG mtDNA sequencing is indicated by the horizontal line.

The NSG and 136 reference mtDNA differ in the position m.9348 (B6/NSG:G/A), which served as the ground truth for estimating false discovery rate (FDR) of iMiGseq. Despite deep coverage (e.g., 10,876×) of UMI groups, this position showed zero non-reference SNV in either mouse strain, giving a conservative FDR estimate of <9.2×10$^{-5}$. These variants were taken advantage of to construct in silico ground-truth heteroplasmies by mixing various numbers of reads subsampled from NSG_2 with all reads of B6_2. iMiGseq accurately determined the heteroplasmy levels in iterated sub-samplings (71-105 times) even when the number of reads was limited. These data were consistent with other IDMseq data (see methods, see Examples above, and Bi, et al., *Genome biology* 21, 213, doi:10.1186/s13059-020-02143-8 (2020)) and showed that the methods provide accurate quantitation of the heteroplasmy levels that are reported in published mtDNA studies.

iMiGseq allowed comparison of the frequencies of variants shared by oocytes of the same mouse. High frequency SNVs (>1% NHL) in NSG oocytes were surveyed and a significant difference in the frequency of the same variant was observed (FIG. 17I). Two SNVs, m.606T>C and m.9941T>C (detrimental, p.Phe22Ser), showed ultra-low frequencies (<0.1% NIHL) in two oocytes but a drastically higher frequency in the third oocyte (FIG. 17I). These results indicated that ultra-rare detrimental variants could under some circumstances accumulate to frequencies above 1% during oogenesis, which supports the need for unbiased studies on these variants using ultra-sensitive methods such as iMiGseq.

Figure 19A:
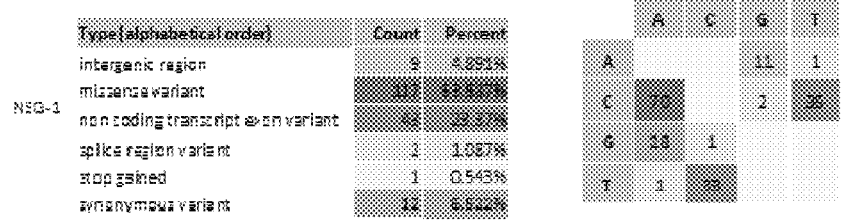
FIGS. 19A-19D show analysis of mtDNA SNVs detected in human oocytes.
Figure 19A:
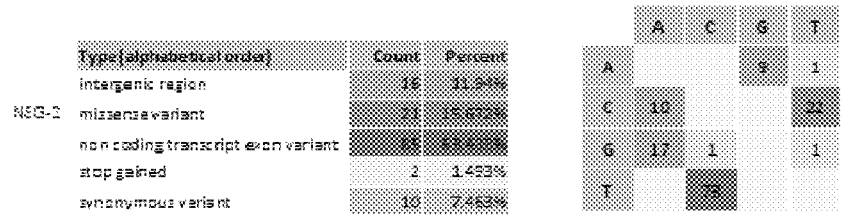
Figure 19A:
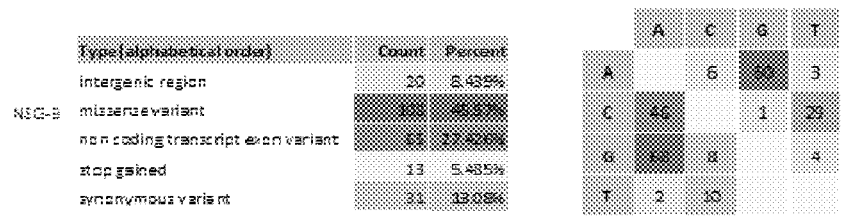
Figure 19A:
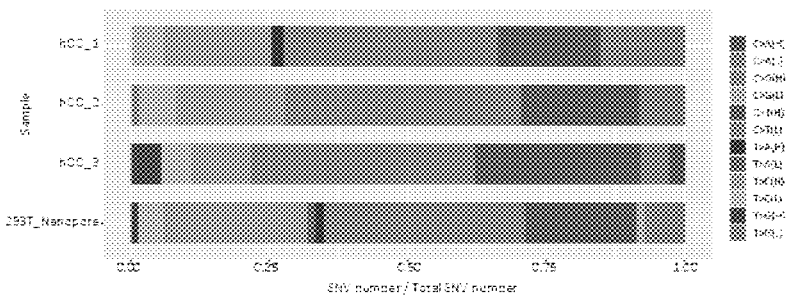
Figure 19B:
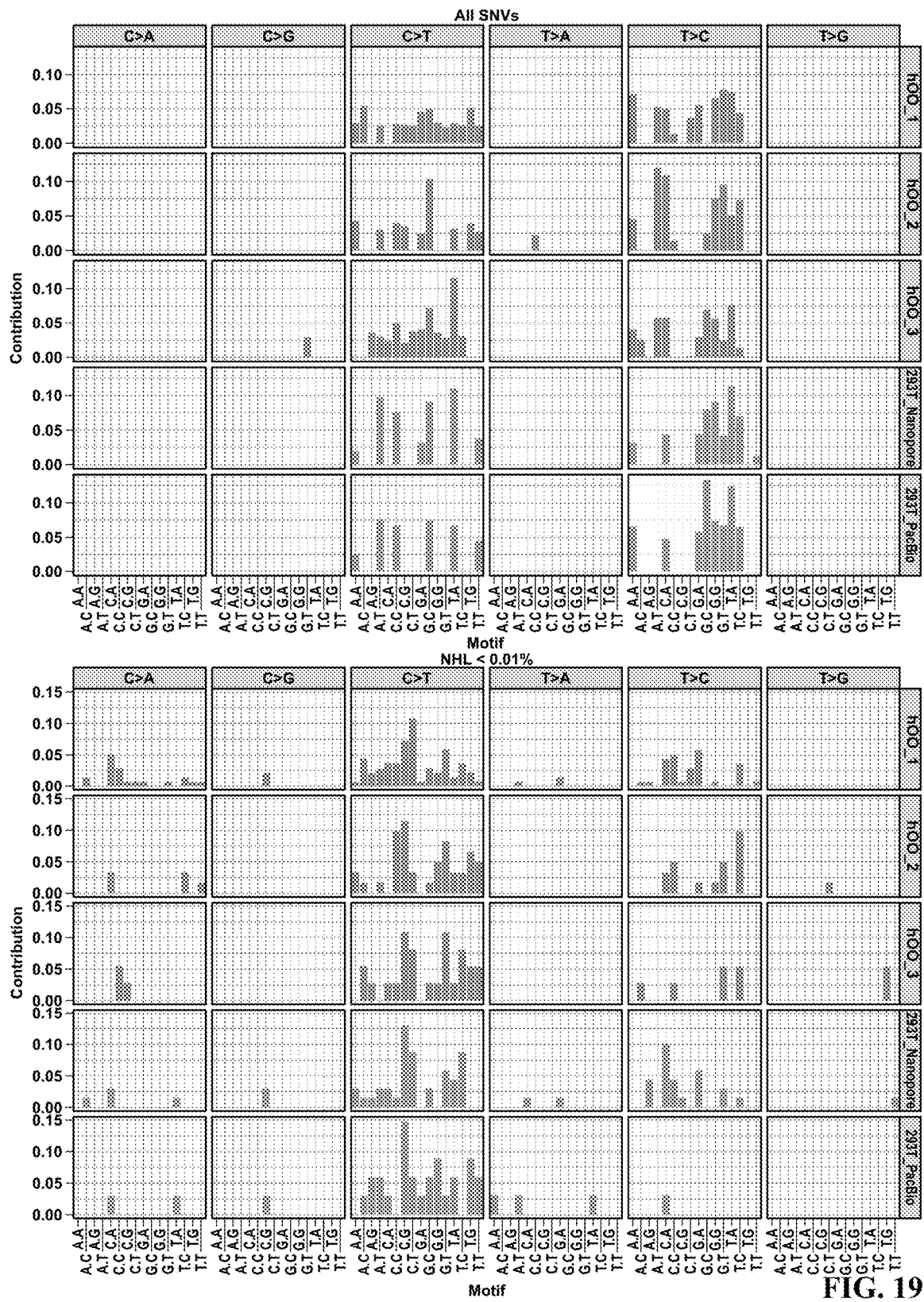
Figure 19C:
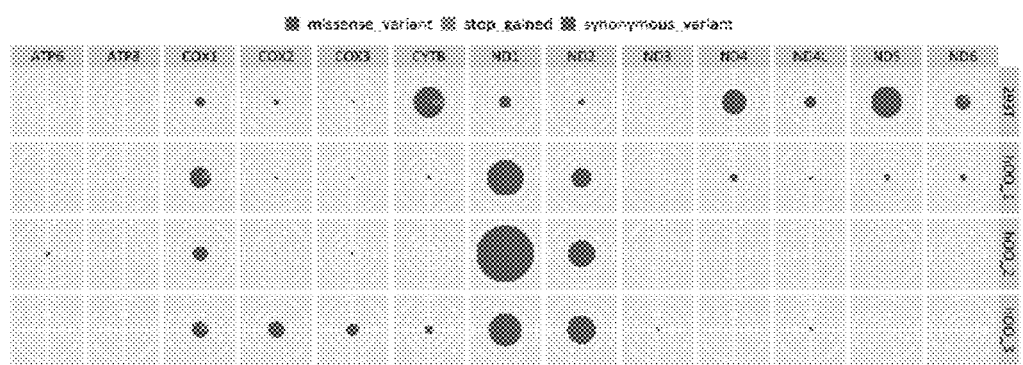
Figure 19D:
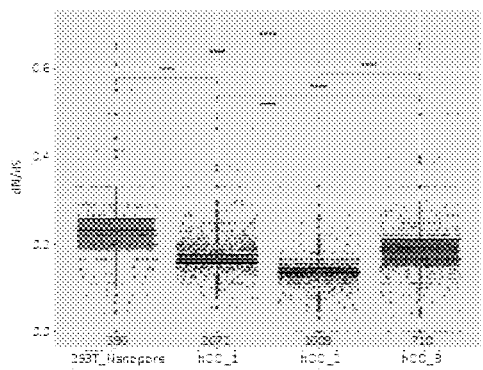
Figure 19E:
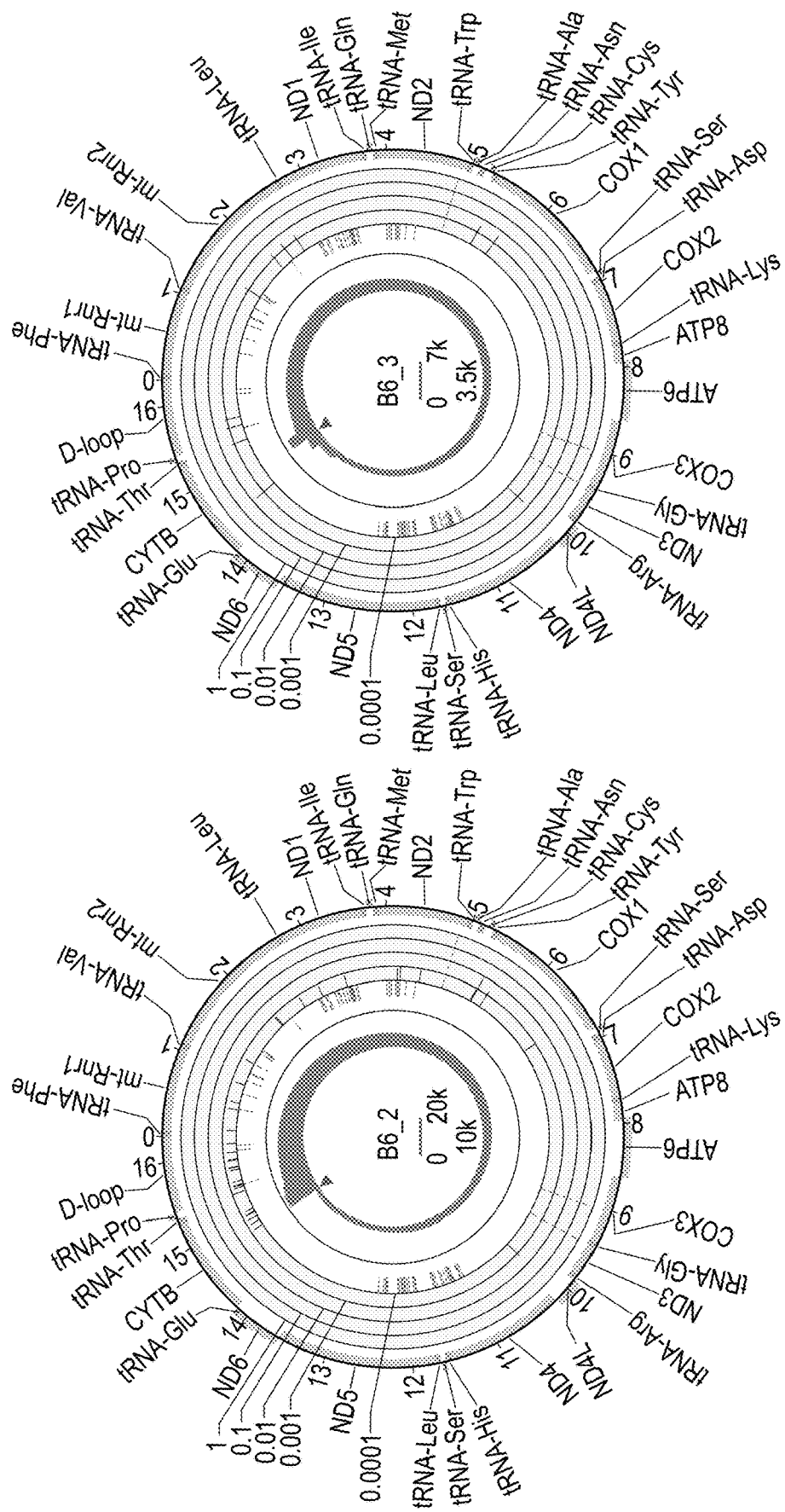
FIGS. 19E-19I show SNV analysis in the iMiGseq of B6 mouse oocytes.
Figures 19F, 19G:
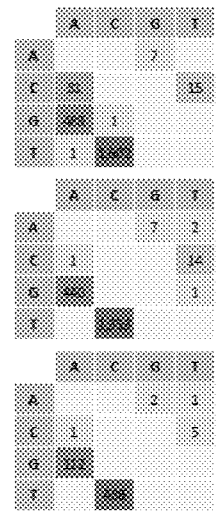
Figure 19H:
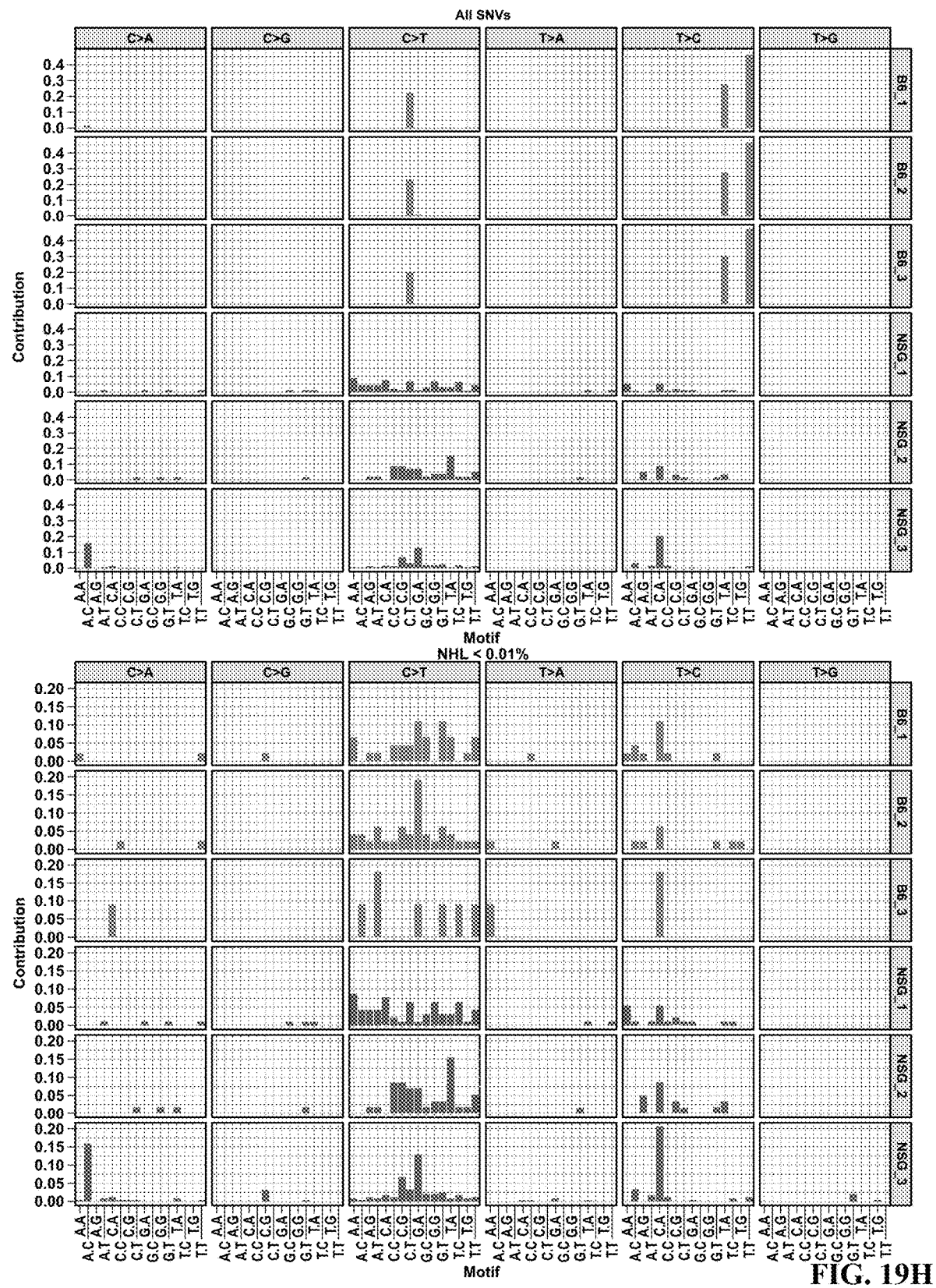
Figure 19I:
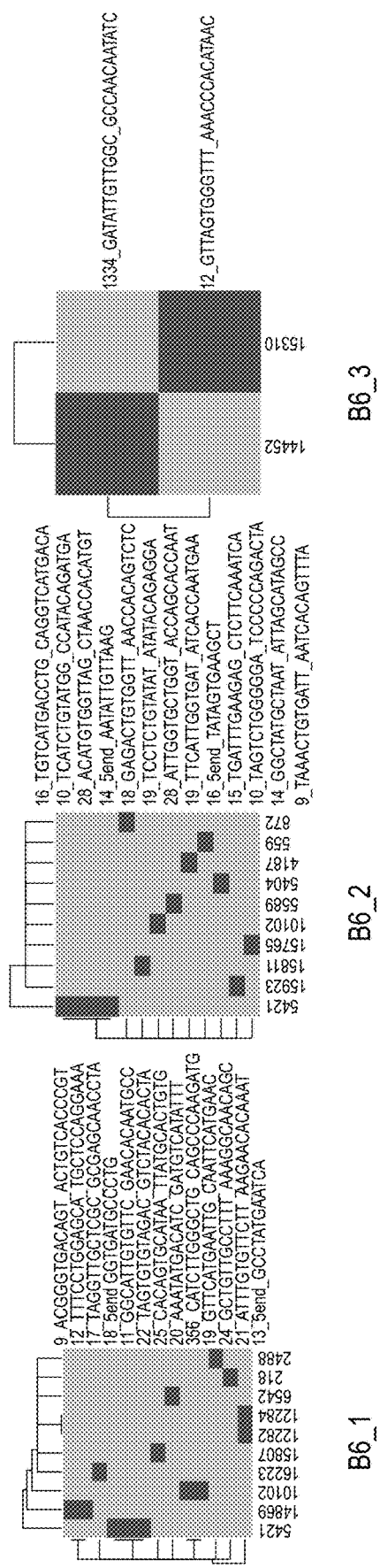
Figure 20A:
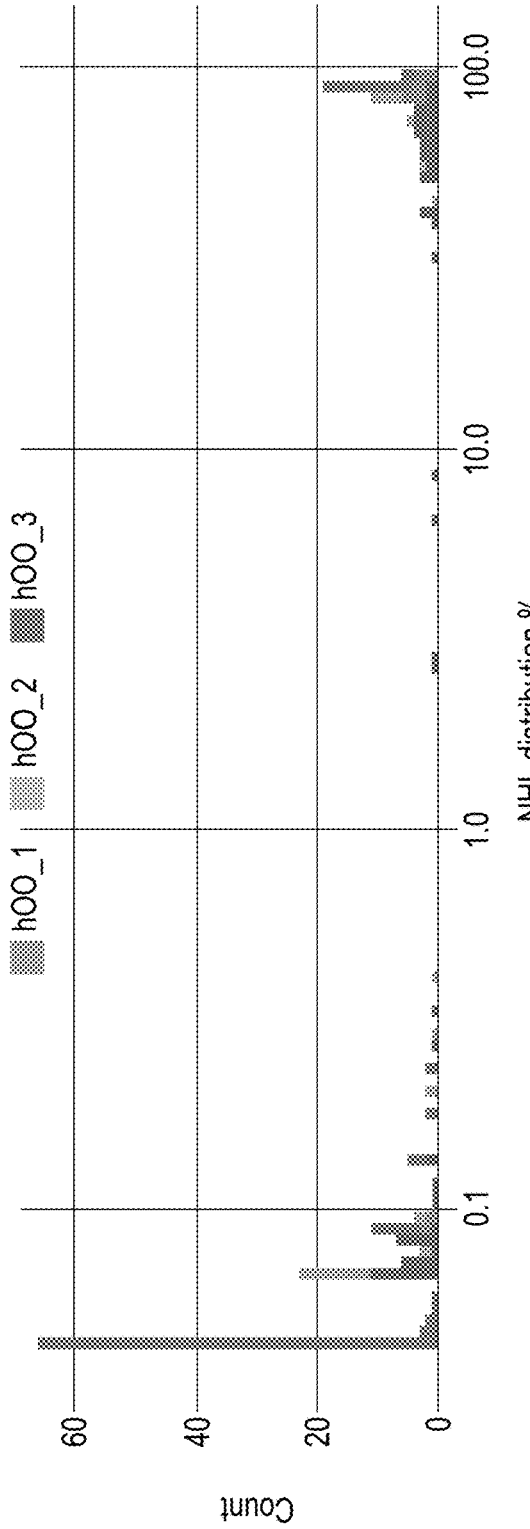
FIGS. 20A-20C show SNV analysis in the iMiGseq of human oocytes.
Figure 20B:
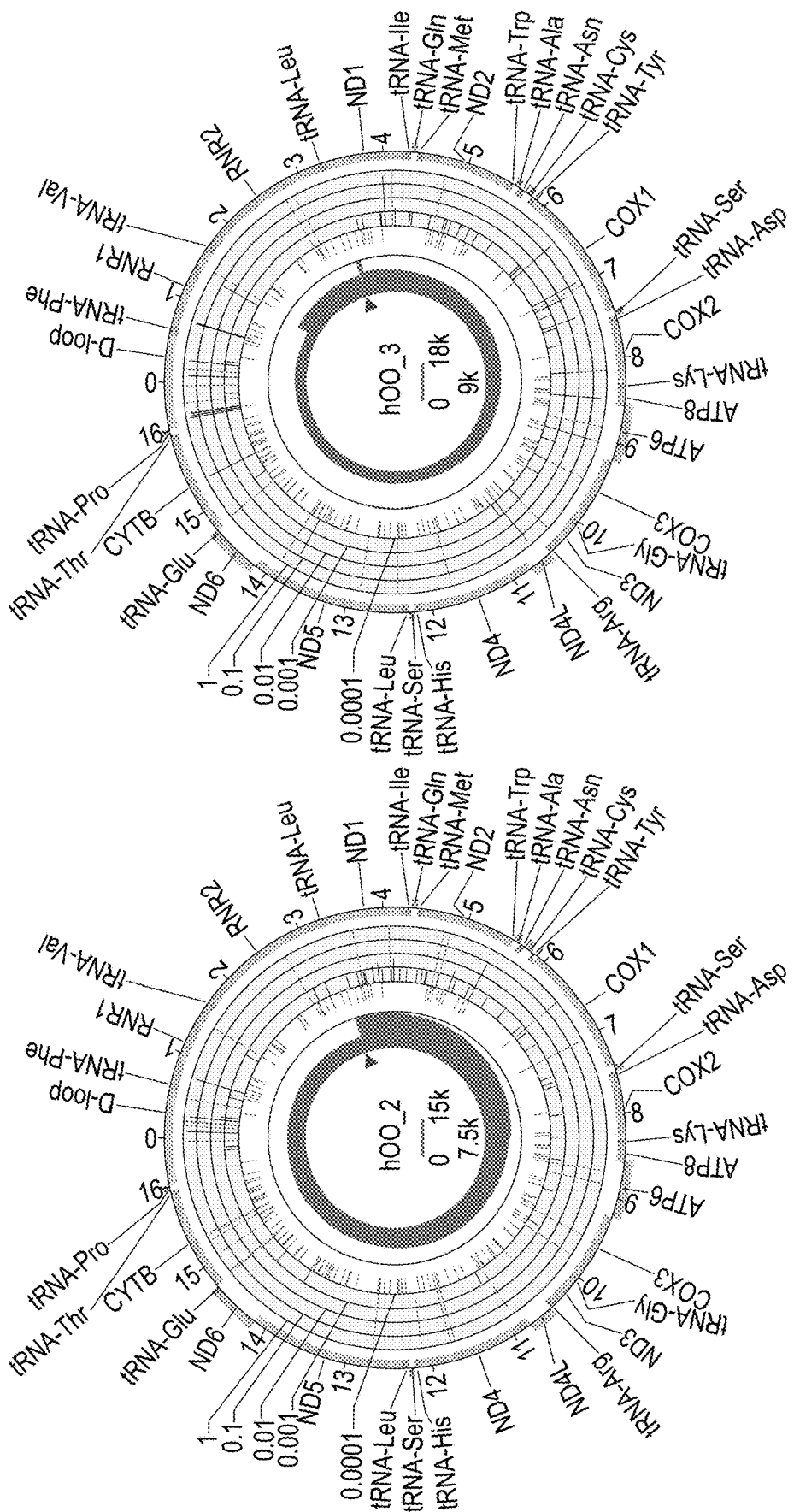
Figure 20C:
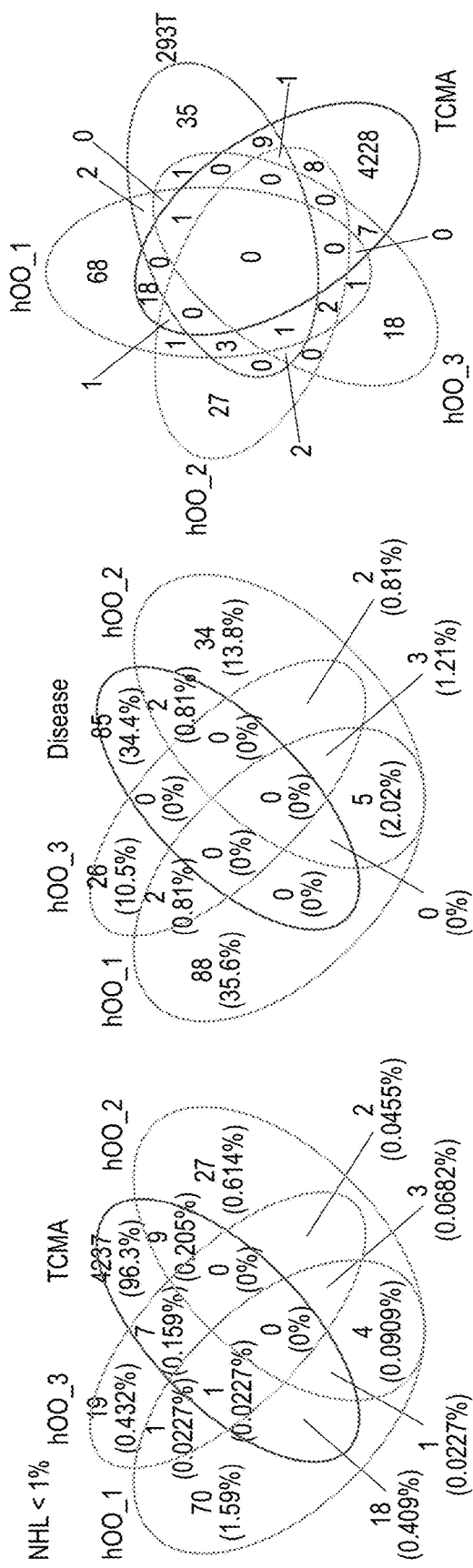
Figure 20C:
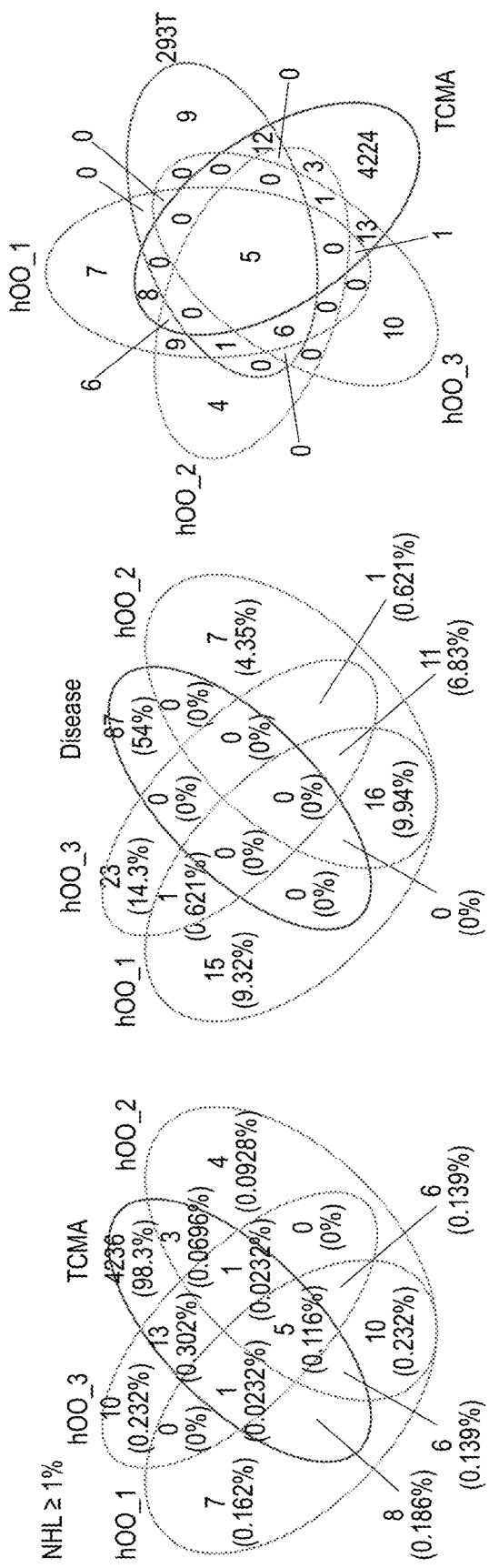
Figure 21A:
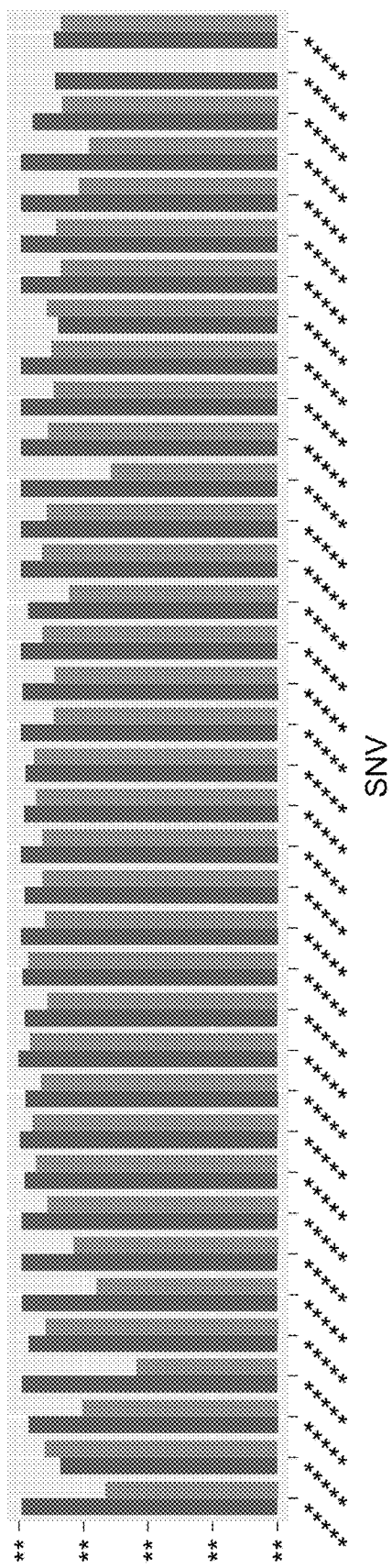
FIGS. 21A-21C show comparison of VAF of SNVs reported by Genbank and by iMiGseq in individual human oocytes.
Figure 21B:
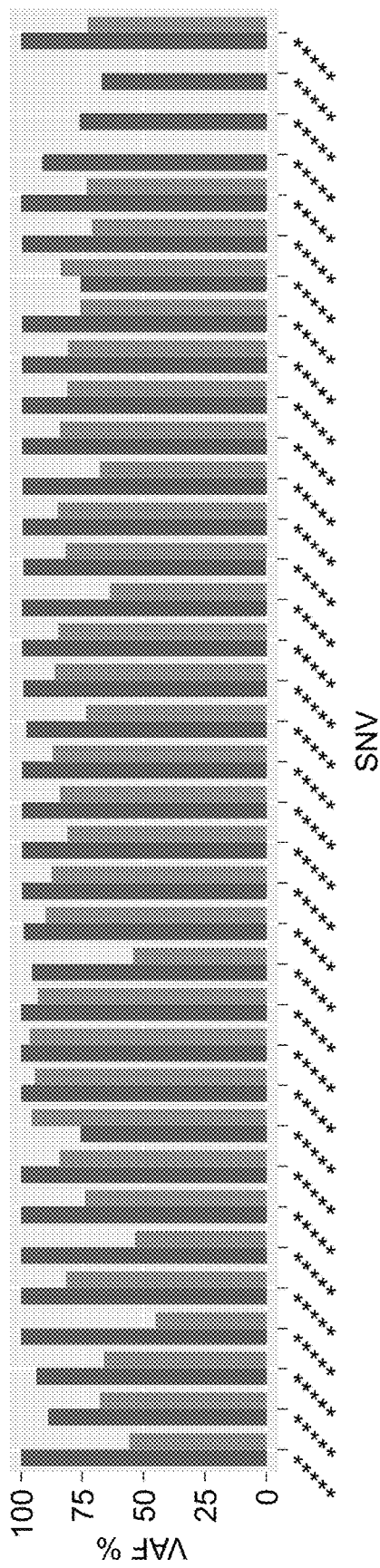
Figure 21C:
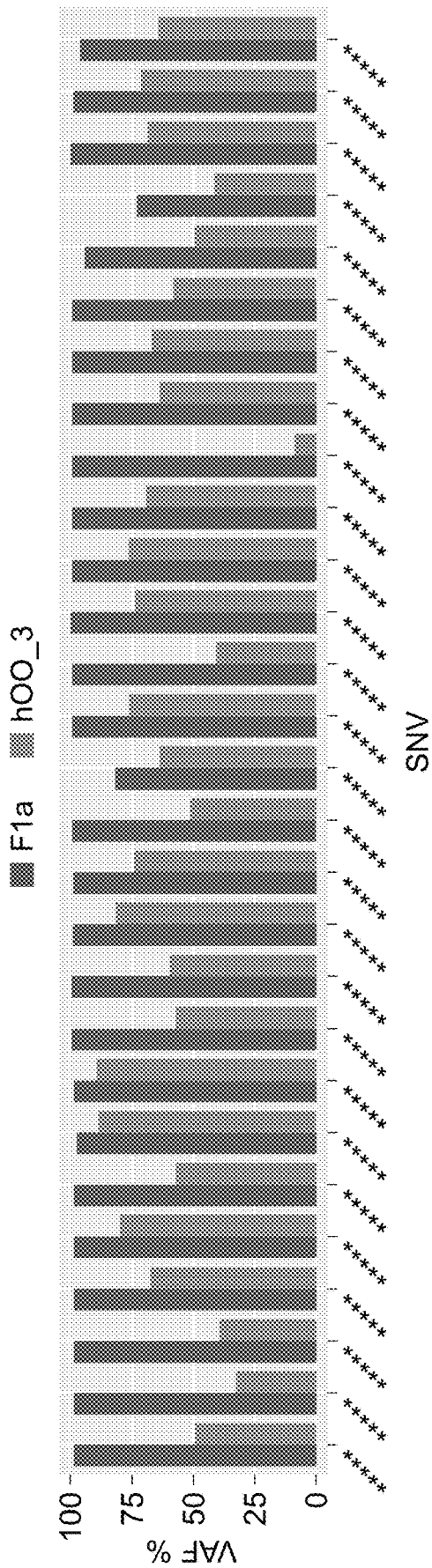

The T>C (A>G) and G>A (C>T) base substitutions were predominant in all six mouse oocytes, consistent with known mtDNA-specific replication-coupled mutational signatures[26, 27, 34] (FIG. 18J, FIGS. 19G & 19H). It is worth noting that the mutation spectrum of the SNVs with NHL<1% was more diverse and could be influenced by one prevailing SNV (e.g., 14027C>A in NSG_1 &3). These data resulted in 537 and 81 fully assembled high-quality mitochondrial genomes for NSG and B6 strains, respectively (Table 9). The SNVs from extensive-coverage mtDNA were clustered in a heatmap to show haplotypes and linkage between heteroplasmic mutations (FIG. 19I). The above findings on heteroplasmic variants were possible due to the analysis of individual mtDNA in single oocyte by iMiGseq and would have been underestimated or missed with conventional methods. Together, they provide a better understanding of the genetic heterogeneity of mtDNA in different mouse strains, which is potentially important for mitochondrial related studies using mouse models.

iMiGseq Reveals Genetic Heterogeneity of mtDNA in the Human Germ Line iMiGseq was next applied to three human mature oocytes (hOOs). To achieve high UMI labeling efficiency in single hOOs, optimal primer sequences were screened for using mtDNA from five 293T cells. iMiGseq generated 0.76, 0.40 and 0.51 million reads, which contributed to 2308, 1461 and 1535 UMI groups in hOO_1, hOO_2 and hOO_3, respectively (Table 9, FIG. 17H). Variant calling based on the human mtDNA reference (NC_012920) showed that all three oocytes contained a significant amount of SNVs (75483 for hOO_1, 32276 for hOO_2 and 22522 for hOO_3). The NHL of SNVs separated into two groups, the high frequency group ranged from 32.40% to 97.18%, while the low frequency group was from 0.04% to 0.41% (FIG. 18A, FIGS. 20A & 20C). The vast majority of SNVs had an NHL below the 1% detection limit of heteroplasmic variants reported in published studies[8, 24-26] (FIG. 18B, 18C). These low-level heteroplasmic SNVs showed marked variation among the three donors, while the high-frequency SNVs (NHL>1%) tended to highlight the shared genetic heritage of them (FIG. 18D). For example, the 11 SNVs shared by all three oocytes separate the L3 haplogroup from its ancestral L0 haplogroup. After the L3 lineage left Africa and migrated to Eurasia, it split into the M and N haplogroups. Interestingly, these SNVs are retained in Asian haplogroups M and F (a daughter group of N) but not in the European haplogroup H, which is consistent with the east Asian origin of the donors[31, 35]. The VAFs of the predominant SNVs (VAF>0.6) in the M and F (N) clades reported by iMiGseq were compared to those in population studies[31]. The result showed that while these SNVs were consistently predominant in the cell, they showed a higher variation of heteroplasmy levels than population-based data across the board, suggesting that single-cell based analysis may better resolve the heterogeneity of mtDNA (FIG. 21A-21C).

Consensus mtDNA sequences were assembled using reads from extensive-coverage UMI groups and obtained 125, 81 and 46 full-length mtDNA for hOO_1, hOO_2 and hOO_3, respectively. MITOMASTER[31] assigned all assembled mtDNA of hOO_2 and hOO_3 to the M7c1c2 and F1a1a haplogroups, respectively. For hOO_1, 122 assembled mtDNA were assigned to M7b1a1b, while the rest (3) contained a different allele (m.3483G>C rather than m.3483G>A) consistent with the M7b1a1 haplogroup. The m.3483G>C SNV caused the 59th amino acid to change from Glu to Asp in the ND1 gene, and was also found in Genbank sequences (MF058561.1 and MF381578.1). Importantly, all of the assigned haplogroups matched the ethnic origin of the donors. These data show that iMiGseq provides base-resolution haplotypes of individual mtDNA at the single-cell level.

Figure 18E:
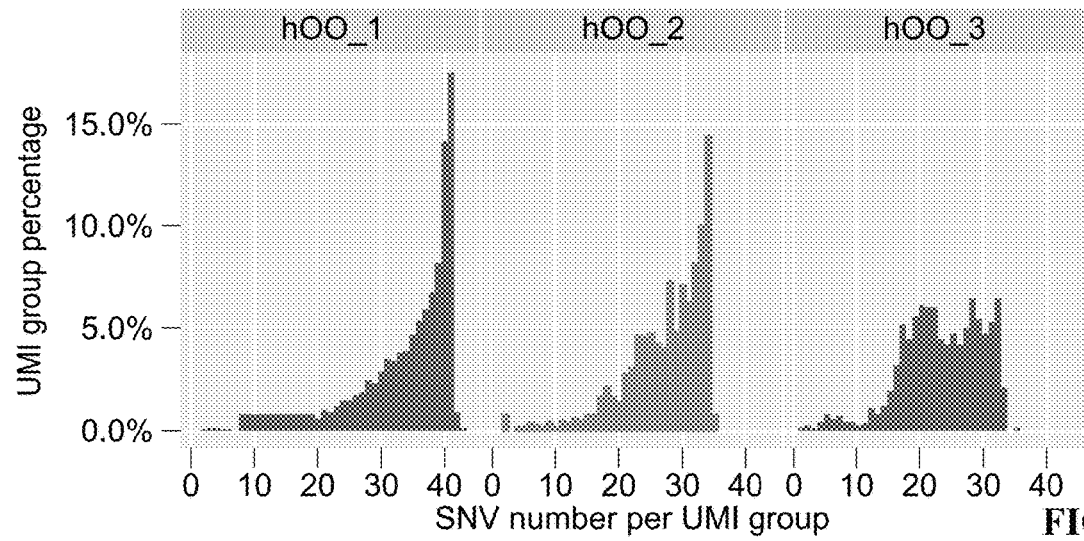
FIG. 18E is a histogram of SNV load per mtDNA in the three hOOs.

The distribution of SNV load per mtDNA of healthy human oocytes was similar to that of 293T cells but distinct from oocytes of NSG and B6 mice (compare FIGS. 16H, 17A and 18E). This is believed to be due to the higher genetic diversity of mtDNA in humans compared to inbred mice.

Figure 18F:
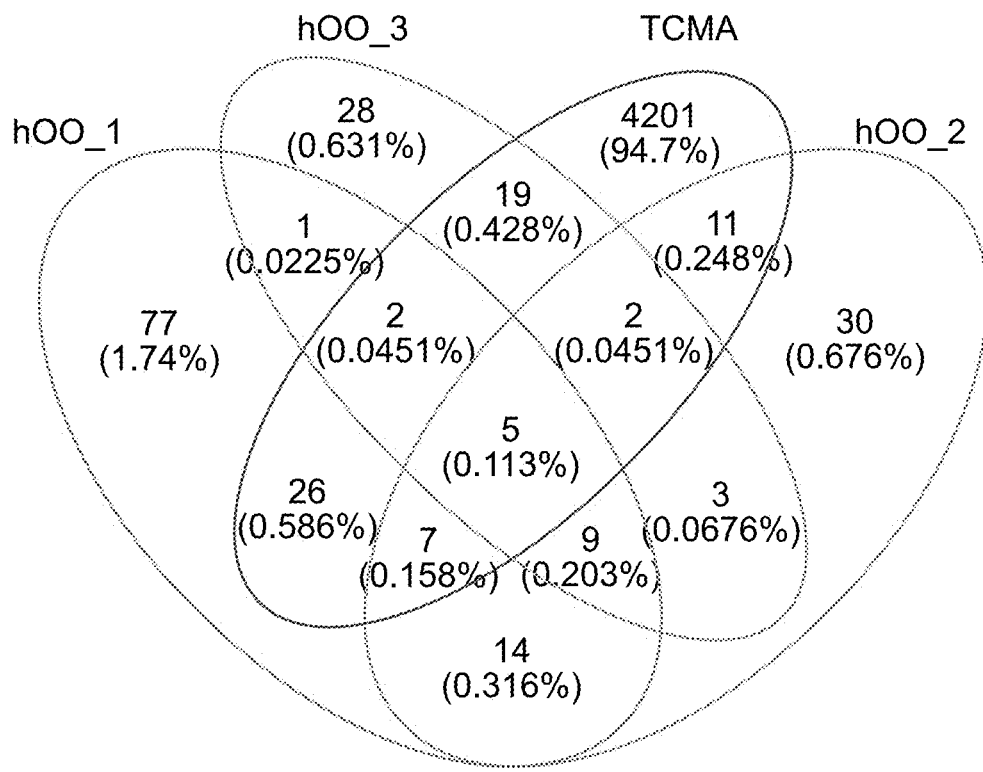
FIG. 18F is Venn diagrams showing the overlap of mtDNA SNVs in hOOs and cancers (TCMA). Cancer related mtDNA SNVs exist in all three hOOs.
Figures 22A, 22B:
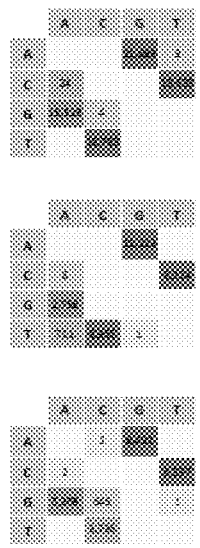
FIG. 22A shows analysis of mtDNA SNVs of hOOs based on functional annotation. The majority of SNVs are synonymous variants in all oocytes.
FIG. 22B shows analysis of mtDNA SNVs of hOOs based on base change. The majority of base changes are A>G (T>C) and C>T (G>A).

The Cancer Mitochondrial Atlas (TCMA[26]) provided a comprehensive collection of heteroplasmic mutations of mtDNA in human cancers. However, the ontogeny of these cancer-associated mtDNA mutations whose occurrence positively correlates with age[26] remains unclear. Interestingly, each of the three hOOs shared a significant portion (28.4%, 40.6% and 30.9% for hOO_1, hOO_2 and hOO_3, respectively) of its unique SNVs with the TCMA database[26] (FIG. 18F). The comparison was refined by separating No enrichment or depletion of low NHL SNVs (<0.01) was observed in the D-loop and tRNA genes in any of the hOOs. Mutations in rRNA genes were significantly depleted in two of the three hOOs (the samples number of hOO_3 was too small for proper statistical testing. Among protein-coding genes, the three hOOs consistently showed frequent mutations in the ND1, ND2 and COX1 genes, which was a different pattern compared to cultured 293T cells (FIG. 19C). Deleterious SNVs accounted for 24.10%, 21.47% and 21.54% of the SNVs in hOO_1, hOO_2 and hOO_3, respectively (FIG. 22A). Frequencies of synonymous mutations were significantly higher than expected by chance, while those of non-synonymous ones appeared random (Table 10).

TABLE 10

The distribution of point heteroplasmies among mtDNA regions hOOs

Figure 18G:
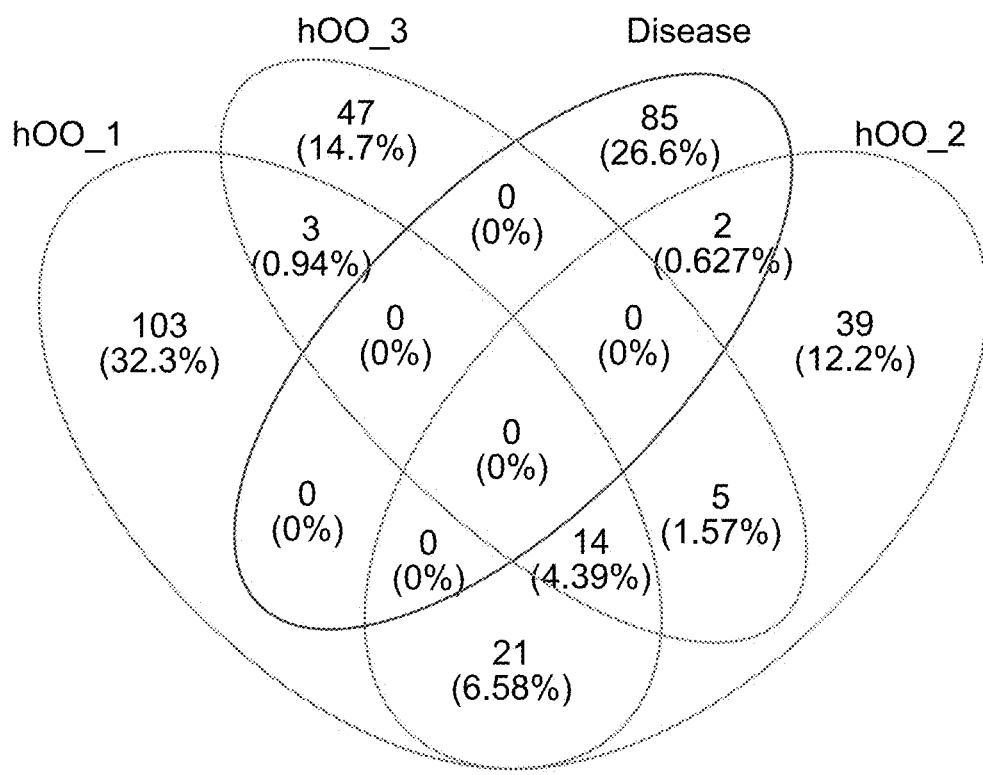
FIG. 18G, similar to FIG. 18F but comparing with confirmed pathogenic mtDNA SNVs in mitochondrial diseases (Disease).
Figure 18H:
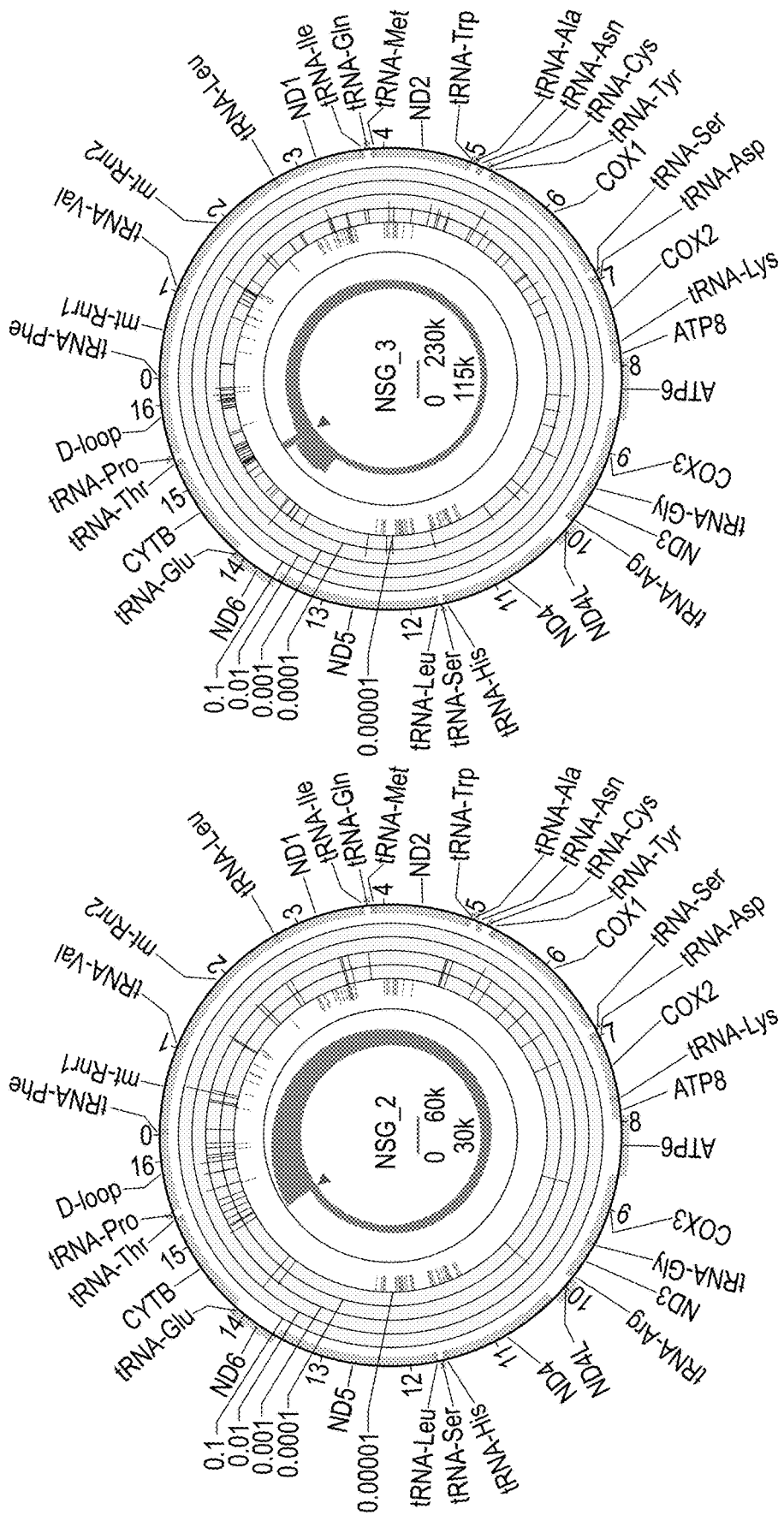
FIG. 18H is circular plots showing the distribution of SNVs in the mitochondrial genome of NSG_2 and NSG_3 oocytes. The arrangement of the circular plots is similar to FIG. 17b.

| Region | bp | Expected % | hOO-1 | | | hOO-2 | | | hOO-3 | | |
| --- | --- | --- | --- | --- | --- | --- | --- | --- | --- | --- | --- |
| | | | Expected | Observed | p-value‡ | Expected | Observed | p-value‡ | Expected | Observed | p-value‡ |
| D-loop | 1122 | 6.8% | 8.9 | 10 | 0.84* | 4.0 | 6 | 0.44* | 2.4 | 2 | 0.94* |
| tRNA | 1508 | 9.1% | 11.9 | 10 | 0.67 | 5.4 | 3 | 0.40* | 3.2 | 2 | 0.69* |
| rRNA | 2513 | 15.2% | 19.9 | 5 | 0.00045 | 9.0 | 3 | 0.047* | 5.3 | 2 | 0.18* |
| Synonymous | 2834 | 17.1% | 22.4 | 35 | 0.005 | 10.1 | 19 | 0.0036 | 6.0 | 11 | 0.043* |
| Non-synonymous | 8533 | 51.5% | 67.5 | 71 | 0.60 | 30.4 | 28 | 0.62 | 18.0 | 18 | 0.87* |
| Total | 16569# | | | 131+ | | | 59+ | | | 35+ | | due to overlapping annotation the total number is different from the sum of all categories.
†include low-coverage groups
‡two-tailed binomial test
*data not met the requirements for z z-test/sample number is smaller than 10 unique SNVs in hOOs according to their NHL (≥1% or <1%), which showed that a significant amount of shared SNVs existed well below the 1% detection limit of most published studies (FIG. 20A). Intersecting the iMiGseq SNVs with a list of confirmed pathogenic mtDNA mutations[31] identified two SNVs causing Leber's hereditary optic neuropathy (LHON) and mitochondrial encephalopathy, lactic acidosis, and stroke-like episodes (MELAS, 3376G>A/p.Glu24Lys in ND1), and chronic progressive external ophthalmoplegia (CPEO, 5690A>G in tRNA$^{Asn}$), respectively. Each was in one mtDNA in hOO_2 (FIG. 18G, FIG. 20C). These data provided evidence that low-level disease-associated heteroplasmic mutations commonly exist in health human oocytes and they may contribute to late-onset cancers or inherited mitochondrial diseases through selection and/or genetic drift[5, 7, 23, 36].

As in 293T cells and mouse oocytes, the predominant base substitutions in human oocytes were T>C (A>G) and C>T (G>A), well known signatures for mitochondrial mutations[26, 27, 34] (FIG. 19A, FIG. 22B). The frequency of reciprocal mutations (e.g. T>C and A>G on the light strand) showed a strand bias, which has been observed by others and attributed to the difference in replication timing of the light and heavy strands[34, 37]. The spectrum of all mutations was consistent with previous data[28] (FIG. 19B). Some mutational signatures (e.g., in the T>C category) were shared by the three hOOs, but the diversity between samples was more evident than that between the Nanopore and PacBio data of 293T cells. This was especially evident in SNVs with NHL<1%, as also seen in mouse oocytes (FIG. 19B, FIG. 19I). Lastly, data from the highly sensitive iMiGseq showed that oxidative damage (causing C>A/G>T transversions) is not a major source of de novo mtDNA mutations in the germline, which was also observed in the brain[27].

The SNVs from extensive-coverage mtDNA were clustered in a heatmap. Several clusters were found within the same hOO, suggesting a potentially different constitutions or origins of mtDNA in single cells. The dN/dS ratio is a major tool used to detect selection on protein-coding mutations[38], and has been used to study selection on mtDNA[26, 34, 39]. The dN/dS ratios of all mtDNA in each of the three hOOs showed strong evidence for purifying (negative) selection on non-synonymous mutations (FIG. 19D). Considering the fact that the hOOs had gone through the genetic bottleneck[4], our data support the role of the germ line mtDNA bottleneck in eliminating deleterious mutations in the offspring.

iMiGseq Quantitates mtDNA Mutations in NARP/Leigh Syndrome hEPS Cells

Since iMiGseq enabled accurate quantitation of mtDNA mutations in a haplotype-resolved manner, we hypothesized that it could improve genetic diagnosis of mitochondrial diseases. Mouse extended pluripotent stem (mEPS) cells can generate blastocyst-like structures (EPS-blastoids) through lineage segregation and self-organization in vitro[56]. If an analogous system can be established using human EPS (hEPS) cells, it could provide a unique model of mitochondrial disease during early embryogenesis. Therefore, as a proof-of-concept, we performed iMiGseq in hEPS cells derived from mitochondrial disease-specific induced pluripotent stem cells (iPSCs) described previously[57]. The patient is a carrier of the mtDNA mutation (m.8993T>C) for neuropathy, ataxia and retinitis pigmentosa (NARP) and maternally inherited Leigh syndrome. She gave birth to two daughters who died of Leigh syndrome and one son who was age three and asymptomatic at the time of sample collection, all confirmed carriers of m.8993T>C. The NAPR/Leigh syndrome hEPS cells (referred to as hEPS$^{m.8993T>C}$ hereafter) were collected for UMI labeling of whole mtDNA with different primer designs (important for avoiding primers overlapping with disease relevant SNPs). As in hOOs, iMiGseq showed an extensive coverage of full-length mtDNA in the hEPS$^{m.8993T>C}$ that supported detailed analysis of variants (e.g., Table 10). It detected the m.8993T>C mutation in 74.2% of mtDNA, which matched the heteroplasmy levels observed in the patient's oocytes (70~90%). Interestingly, one of the m.8993T>C mutant mtDNA also harbored a 251-bp deletion in the D-loop region. These results demonstrated that iMiGseq could not only detect and quantitate disease-causing mutations but also provide comprehensive characterizations of all types of mutations, including SNVs and SVs, and their genetic linkage with high sensitivity and specificity. These data presented herein are believed to represent the first demonstration of a high-throughput base-resolution analysis of individual full-length mtDNA in single cells. Taking advantages of molecular consensus sequencing (IDMseq) and a specially designed bioinformatics pipeline (VAULT), iMiGseq (e.g., as described in Example 7) greatly improved the sensitivity of heteroplasmy detection and showed that most unique mtDNA SNVs in cells are rare and well below the current 1% detection limit. They indicate that a hitherto underestimated population of rare somatic mtDNA variants exist in the female germline, much like the submerged portion of an iceberg hidden below the technological limit. It is conceivable that some of these variants may resurface due to genetic drift, mtDNA bottleneck, selection or a combination of any of these processes and contribute to the large variations in heteroplasmy levels in human pedigrees and complex diseases during aging[2].

Further analysis showed that deleterious SNVs were prevalent among heteroplasmic SNVs in both mouse and human oocytes. A sizable portion of low-level heteroplasmic SNVs are associated with cancers or mitochondrial diseases, which raises important questions about the role of these rare mtDNA mutations that exist in beginning of life in oncogenesis and the diagnosis and prevention of mitochondrial diseases. Note that only one of the most conservative lists of mitochondrial disease variants was surveyed, and many other mtDNA variants have been reported to link to mitochondrial diseases and complex diseases[2, 31], so the overlap with disease variants may be even bigger. iMiGseq could offer new opportunities to follow the dynamics of such SNVs during development and aging in hope to decipher the emergence of mutations and understand their clinical significance.

Through analysis of thousands of individual mtDNA, iMiGseq revealed large genetic heterogeneity in mitochondria among oocytes of the same female or different females. These observations are consistent with the existence a mitochondrial bottleneck in primordial germ cell (PGC) development as previously reported[14, 15]. Analysis of dN/dS ratios of thousands of mtDNA in single hOOs showed strong evidence for purification selection of non-synonymous mutations in the human oogenesis.

Because NGS of mtDNA necessitates fragmentation of mtDNA molecules, it is impossible to ascertain the true haplotype of individual mtDNA molecules. It is thus extremely difficult to use short-read NGS data to study genetic interaction between rare mutations and their genetic backgrounds. Short reads could also be erroneously mapped to NUMTs, causing false variants[40]. Thanks to the ultra-long reads of Nanopore sequencing, iMiGseq could provide thousands of full-length mtDNA and their variants in a cell, which completely avoids NUMTs and enables studies of interactions between different heteroplasmies. Nanopore-based IDMseq has been shown to offer superior characterization of SVs induced by CRISPR/Cas9 editing in human embryonic stem cells[3]. Interestingly, unlike widespread low-level heteroplasmies uncovered by the higher sensitivity, no large SV was detected in healthy cells. One limitation of the current analysis is variant calling for small insertions and deletions, which remains challenging in most sequencing platforms[41, 42]. Although the sample sizes were limited, our data extend previous observations that SVs are rarely transmitted through the human germline[2] to higher sensitivity, and suggest a strong purifying selection against deleterious SVs in oogenesis.

Because iMiGseq enables for the first time quantitative base-resolution analysis of thousands of mtDNA in single cells, it offers an unprecedented opportunity for preimplantation genetic diagnosis (PGD) of mitochondrial diseases. Despite the prevalence (~1 in 5000) of mitochondrial diseases, current diagnostic procedures have been ineffective due to large genetic heterogeneity of mtDNA among different cells. iMiGseq could be used to analyze mtDNA mutational load in single biopsied blastomeres, which have been shown by several studies[43-46] to represent well the heteroplasmy level of in vitro fertilized embryos. Besides the germline, it is logical to extend iMiGseq technology to somatic tissues to unravel the direction of causality between mtDNA mutations and aging and complex diseases in the future.

REFERENCES

1 Stewart, J. B. & Chinnery, P. F. The dynamics of mitochondrial DNA heteroplasmy: implications for human health and disease. *Nature reviews* 16, 530-542, doi: 10.1038/nrg3966 (2015).

2 Wallace, D. C. & Chalkia, D. Mitochondrial DNA genetics and the heteroplasmy conundrum in evolution and disease. *Cold Spring Harbor perspectives in biology* 5, a021220, doi:10.1101/cshperspect.a021220 (2013).

3 Bi, C. et al. Long-read individual-molecule sequencing reveals CRISPR-induced genetic heterogeneity in human ESCs. *Genome Biol,* doi:10.1186/s13059-020-02143-8 (2020).

4 Floros, V. I. et al. Segregation of mitochondrial DNA heteroplasmy through a developmental genetic bottleneck in human embryos. *Nature cell biology* 20, 144-151, doi:10.1038/s41556-017-0017-8 (2018).

5 Zhang, H., Burr, S. P. & Chinnery, P. F. The mitochondrial DNA genetic bottleneck: inheritance and beyond. *Essays Biochem* 62, 225-234, doi:10.1042/EBC20170096 (2018).

6 Kukat, C. et al. Super-resolution microscopy reveals that mammalian mitochondrial nucleoids have a uniform size and frequently contain a single copy of mtDNA. *Proceedings of the National Academy of Sciences of the United States of America* 108, 13534-13539, doi:10.1073/pnas.1109263108 (2011).

7 Zaidi, A. A. et al. Bottleneck and selection in the germline and maternal age influence transmission of mitochondrial DNA in human pedigrees. *Proceedings of the National Academy of Sciences of the United States of America* 116, 25172-25178, doi:10.1073/pnas.1906331116 (2019).

8 Rebolledo-Jaramillo, B. et al. Maternal age effect and severe germ-line bottleneck in the inheritance of human mitochondrial DNA. *Proceedings of the National Academy of Sciences of the United States of America* 111, 15474-15479, doi:10.1073/pnas.1409328111 (2014).

9 Kong, A. et al. Rate of de novo mutations and the importance of father's age to disease risk. *Nature* 488, 471-475, doi:10.1038/nature11396 (2012).
10 Kauppila, T. E., Kauppila, J. H. & Larsson, N. G. Mammalian Mitochondria and Aging: An Update. *Cell Metab* 25, 57-71, doi:10.1016/j.cmet.2016.09.017 (2017).
11 Schon, E. A., DiMauro, S. & Hirano, M. Human mitochondrial DNA: roles of inherited and somatic mutations. *Nature reviews* 13, 878-890, doi:10.1038/nrg3275 (2012).
12 Elliott, H. R., Samuels, D. C., Eden, J. A., Relton, C. L. & Chinnery, P. F. Pathogenic mitochondrial DNA mutations are common in the general population. *Am J Hum Genet* 83, 254-260, doi:10.1016/j.ajhg.2008.07.004 (2008).
13 Kim, K., Kenigsberg, S., Jurisicova, A. & Bentov, Y. The Role of Mitochondria in Oocyte and Early Embryo Health. *OBM Genetics* 3, 1-1, doi:10.21926/obm.genet.1901070 (2019).
14 Cree, L. M. et al. A reduction of mitochondrial DNA molecules during embryogenesis explains the rapid segregation of genotypes. *Nature genetics* 40, 249-254, doi:10.1038/ng.2007.63 (2008).
15 Wai, T., Teoli, D. & Shoubridge, E. A. The mitochondrial DNA genetic bottleneck results from replication of a subpopulation of genomes. *Nature genetics* 40, 1484-1488, doi:10.1038/ng.258 (2008).
16 Cao, L. Q. et al. The mitochondrial bottleneck occurs without reduction of mtDNA content in female mouse germ cells. *Nature Genetics* 39, 386-390, doi:10.1038/ng1970 (2007).
17 Cao, L. et al. New evidence confirms that the mitochondrial bottleneck is generated without reduction of mitochondrial DNA content in early primordial germ cells of mice. *PLoS genetics* 5, e1000756, doi:10.1371/journal.pgen.1000756 (2009).
18 Cortopassi, G. A. & Arnheim, N. Detection of a specific mitochondrial DNA deletion in tissues of older humans. *Nucleic acids research* 18, 6927-6933 (1990).
19 Brierley, E. J., Johnson, M. A., Lightowlers, R. N., James, O. F. & Turnbull, D. M. Role of mitochondrial DNA mutations in human aging: implications for the central nervous system and muscle. *Ann Neurol* 43, 217-223, doi:10.1002/ana.410430212 (1998).
20 Corral-Debrinski, M., Shoffner, J. M., Lott, M. T. & Wallace, D. C. Association of mitochondrial DNA damage with aging and coronary atherosclerotic heart disease. *Mutat Res* 275, 169-180 (1992).
21 Hudson, G. et al. Two-stage association study and meta-analysis of mitochondrial DNA variants in Parkinson disease. *Neurology* 80, 2042-2048, doi:10.1212/WNL.0b013e318294b434 (2013).
22 Ghezzi, D. et al. Mitochondrial DNA haplogroup K is associated with a lower risk of Parkinson's disease in Italians. *Eur J Hum Genet* 13, 748-752, doi:10.1038/sj.ejhg.5201425 (2005).
23 Li, M., Schroder, R., Ni, S., Madea, B. & Stoneking, M. Extensive tissue-related and allele-related mtDNA heteroplasmy suggests positive selection for somatic mutations. *Proceedings of the National Academy of Sciences of the United States of America* 112, 2491-2496, doi:10.1073/pnas.1419651112 (2015).
24 Duan, M., Tu, J. & Lu, Z. Recent Advances in Detecting Mitochondrial DNA Heteroplasmic Variations. *Molecules* 23, doi:10.3390/molecules23020323 (2018).
25 Payne, B. A., Gardner, K., Coxhead, J. & Chinnery, P. F. Deep resequencing of mitochondrial DNA. *Methods in molecular biology* (Clifton, N.J 1264, 59-66, doi:10.1007/978-1-4939-2257-4_6 (2015).
26 Yuan, Y. et al. Comprehensive molecular characterization of mitochondrial genomes in human cancers. *Nature genetics* 52, 342-352, doi:10.1038/s41588-019-0557-x (2020).
27 Kennedy, S. R., Salk, J. J., Schmitt, M. W. & Loeb, L. A. Ultra-sensitive sequencing reveals an age-related increase in somatic mitochondrial mutations that are inconsistent with oxidative damage. *PLoS genetics* 9, e1003794, doi:10.1371/journal.pgen.1003794 (2013).
28 Ludwig, L. S. et al. Lineage Tracing in Humans Enabled by Mitochondrial Mutations and Single-Cell Genomics. *Cell* 176, 1325-1339 e1322, doi:10.1016/j.cell.2019.01.022 (2019).
29 Ancora, M. et al. Complete sequence of human mitochondrial DNA obtained by combining multiple displacement amplification and next-generation sequencing on a single oocyte. *Mitochondrial DNA A DNA Mapp Seq Anal* 28, 180-181, doi:10.3109/19401736.2015.1115499 (2017).
30 Ni, T. et al. MitoRCA-seq reveals unbalanced cytocine to thymine transition in Polg mutant mice. *Scientific reports* 5, 12049, doi:10.1038/srep12049 (2015).
31 Lott, M. T. et al. mtDNA Variation and Analysis Using Mitomap and Mitomaster. *Curr Protoc Bioinformatics* 44, 1 23 21-26, doi:10.1002/0471250953.bi0123s44 (2013).
32 Lin, Y. C. et al. Genome dynamics of the human embryonic kidney 293 lineage in response to cell biology manipulations. *Nat Commun* 5, doi:ARTN 4767 10.1038/ncomms5767 (2014).
33 Kauppila, J. H. K. et al. Base-excision repair deficiency alone or combined with increased oxidative stress does not increase mtDNA point mutations in mice. *Nucleic Acids Res* 46, 6642-6669, doi:10.1093/nar/gky456 (2018).
34 Ju, Y. S. et al. Origins and functional consequences of somatic mitochondrial DNA mutations in human cancer. *eLife* 3, doi:10.7554/eLife.02935 (2014).
35 Underhill, P. A. & Kivisild, T. Use of y chromosome and mitochondrial DNA population structure in tracing human migrations. *Annu Rev Genet* 41, 539-564, doi:10.1146/annurev.genet.41.110306.130407 (2007).
36 Coller, H. A. et al. High frequency of homoplasmic mitochondrial DNA mutations in human tumors can be explained without selection. *Nature genetics* 28, 147-150, doi:10.1038/88859 (2001).
37 Tanaka, M. & Ozawa, T. Strand asymmetry in human mitochondrial DNA mutations. *Genomics* 22, 327-335, doi:10.1006/geno.1994.1391 (1994).
38 Nielsen, R. Molecular signatures of natural selection. *Annu Rev Genet* 39, 197-218, doi:10.1146/annurev.genet.39.073003.112420 (2005).
39 Ingman, M. & Gyllensten, U. Rate variation between mitochondrial domains and adaptive evolution in humans. *Human molecular genetics* 16, 2281-2287, doi:10.1093/hmg/ddm180 (2007).
40 Santibanez-Koref, M. et al. Assessing mitochondrial heteroplasmy using next generation sequencing: A note of caution. *Mitochondrion* 46, 302-306, doi:10.1016/j.mito.2018.08.003 (2019).
41 Goodwin, S., McPherson, J. D. & McCombie, W. R. Coming of age: ten years of next-generation sequencing technologies. *Nature reviews* 17, 333-351, doi:10.1038/nrg.2016.49 (2016).
42 Zhou, A. B., Lin, T. & Xing, J. C. Evaluating nanopore sequencing data processing pipelines for structural varia- 43 Monnot, S. et al. Segregation of mtDNA throughout human embryofetal development: m.3243A>G as a model system. *Hum Mutat* 32, 116-125, doi:10.1002/humu.21417 (2011).

44 Tajima, H. et al. The development of novel quantification assay for mitochondrial DNA heteroplasmy aimed at preimplantation genetic diagnosis of Leigh encephalopathy. *J Assist Reprod Genet* 24, 227-232, doi:10.1007/s10815-007-9114-0 (2007).

45 Treff, N. R. et al. Blastocyst preimplantation genetic diagnosis (PGD) of a mitochondrial DNA disorder. *Fertil Steril* 98, 1236-1240, doi:10.1016/j.fertnstert.2012.07.1119 (2012).

46 Thorburn, D. R., Wilton, L. & Stock-Myer, S. Healthy Baby Girl Born Following Pre-Implantation Genetic Diagnosis for Mitochondrial DNA M.8993t>G Mutation. *Molecular Genetics and Metabolism* 98, 5-6 (2009).

47 Li, H. et al. The Sequence Alignment/Map format and SAMtools. *Bioinformatics* 25, 2078-2079, doi:10.1093/bioinformatics/btp352 (2009).

48 Cingolani, P. et al. A program for annotating and predicting the effects of single nucleotide polymorphisms, SnpEff: SNPs in the genome of *Drosophila melanogaster* strain w(1118); iso-2; iso-3. *Fly* 6, 80-92, doi:10.4161/fly.19695 (2012).

49 Li, H. Minimap2: pairwise alignment for nucleotide sequences. *Bioinformatics* 34, 3094-3100, doi:10.1093/bioinformatics/bty191 (2018).

50 Sedlazeck, F. J. et al. Accurate detection of complex structural variations using single-molecule sequencing. *Nat Methods* 15, 461-468, doi:10.1038/s41592-018-0001-7 (2018).

51 Koren, S. et al. Canu: scalable and accurate long-read assembly via adaptive k-mer weighting and repeat separation. *Genome Res* 27, 722-736, doi:10.1101/gr.215087.116 (2017).

52 Nei, M. & Gojobori, T. Simple Methods for Estimating the Numbers of Synonymous and Nonsynonymous Nucleotide Substitutions. *Mol Biol Evol* 3, 418-426 (1986).

53 Gehring, J. S., Fischer, B., Lawrence, M. & Huber, W. SomaticSignatures: inferring mutational signatures from single-nucleotide variants. *Bioinformatics* 31, 3673-3675, doi:10.1093/bioinformatics/btv408 (2015).

54 Yu, Y. et al. Effects of combined epidermal growth factor, brain-derived neurotrophic factor and insulin-like growth factor-1 on human oocyte maturation and early fertilized and cloned embryo development. *Hum Reprod* 27, 2146-2159, doi:10.1093/humrep/des099 (2012).

55 Wenger, A. M. et al. Accurate circular consensus long-read sequencing improves variant detection and assembly of a human genome. *Nature biotechnology* 37, 1155-1162, doi:10.1038/s41587-019-0217-9 (2019).

56 Li, R. et al. Generation of Blastocyst-like Structures from Mouse Embryonic and Adult Cell Cultures. *Cell* 179, 687-702 e618, doi:10.1016/j.cell.2019.09.029 (2019).

57 Yang, Y. et al. Derivation of Pluripotent Stem Cells with In Vivo Embryonic and Extraembryonic Potency. *Cell* 169, 243-257 e225, doi:10.1016/j.cell.2017.02.005 (2017).

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of analyzing full-length genomic mitochondrial DNA comprising
   (a) preparing labeled-target mitochondrial DNA comprising polymerase-based extension of one or more unique molecular identifier (UMI) primers along a target mitochondrial DNA template, each UMI primer comprising a universal primer sequence, a unique molecular identifier (UMI) sequence, and a mitochondrial DNA binding sequence,
   wherein the source of the target mitochondrial DNA template is any integer between 1 and 100 cells inclusive, or any range formed of two integers there between;
   (b) amplifying the labeled-target mitochondrial DNA by one or more rounds of polymerase chain reaction (PCR) comprising a universal primer that binds to the universal primer sequence and one or more mitochondrial DNA primers that bind to a mitochondrial DNA sequence of the labeled-target mitochondrial DNA;
   (c) sequencing the amplified labeled-target mitochondrial DNA using long-read sequencing technology;
   (d) grouping sequences having the same UMI into one or more groups; and
   (e) determining the full-length sequence of each labeled-target mitochondrial DNA by determining a consensus sequence of each UMI group.

2. The method of claim 1, further comprising
   (f) identifying polymorphisms in one or more of the labeled-target mitochondrial DNA.

3. The method of claim 2, wherein the polymorphism is a single nucleotide polymorphism (SNP).

4. The method of claim 2, wherein (e) and/or (f) are carried out using bioinformatics analysis.

5. The method of claim 4, wherein the bioinformatics analysis comprises basecalling, sequence alignment(s), polymorphism identification or a combination thereof.

6. The method of claim 1, wherein the long-read sequencing technology comprises a system for preparing ultra-long reads exceeding 800 kb, single molecule real time sequencing (SMRT).

7. The method of claim 6, wherein the long-read sequencing technology comprises preparing a ID ligation library from the labeled amplicons.

8. The method of claim 1, wherein the target mitochondrial DNA template comprises a gene selected from the group consisting of TP53, P21, XPB, XPD, TTDA, LMNA, WRN, CSA, CSB, TOR, S6K, IGF1, IIS, DNMT3A, TET2, JAK2, ASXL1, SF3B1, SRSF2, RUNX1, NRAS, and FLT3.

9. The method of claim 1, wherein the target mitochondrial DNA template is from a single cell.

10. The method of claim 9, wherein the source of the target mitochondrial DNA template is one single mitochondrion.

11. The method of claim 1, wherein the source of the target mitochondrial DNA template is somatic cell(s).

12. The method of claim 1, wherein the source of the target mitochondrial DNA template is germ cell(s).

13. The method of claim 1, wherein the source of the target mitochondrial DNA template is oocyte(s) or pre-implantation embryonic tissue.

14. The method of claim 13, further comprising identifying genomic mitochondrial mutations in the target mitochondrial DNA.

15. The method of claim 14, further comprising determining the oocyte(s) or pre-implantation embryo has or is likely to develop a mitochondrial disease or disorder when the identified genomic mitochondrial mutation(s) are associated with the mitochondrial disease or disorder.

16. The method of claim 1, wherein each specific UMI is associated with a single mitochondrial genome.

17. The method of claim 16, further comprising (f) comparing the consensus sequence of each UMI group to determine the heterogeneity of mitochondrial genomic sequence among different mitochondria from the same cell.

18. The method of claim 17, wherein the target mitochondrial DNA template is from a single cell, and further comprising repeating steps (a)-(f) separately on one or more additional single cells.

19. The method of claim 18, further comprising (g) comparing the consensus sequence of each UMI group to determine the heterogeneity among different mitochondrial genomes from the different cells.

20. The method of claim 1, wherein target mitochondrial DNA template is extracted from a lysate of the cell or cells prior to step (a).

* * * * *

SEQUENCE LISTING

<160> NUMBER OF SEQ ID NOS: 55

<210> SEQ ID NO 1
<211> LENGTH: 28
<212> TYPE: DNA
<213> ORGANISM: Artificial Sequence
<220> FEATURE:
<223> OTHER INFORMATION: synthetic polynucleotide

<400> SEQUENCE: 1
catcttacga ttacgccaac cacgctcc                                          28

<210> SEQ ID NO 2
<211> LENGTH: 10
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: n = any nucleotide (e.g., A or G or C or T)
<220> FEATURE:
<221> NAME/KEY: misc_feature
<222> LOCATION: (7)..(10)
<223> OTHER INFORMATION: n = any nucleotide (e.g., A or G or C or T)

<400> SEQUENCE: 2 nnnntgnnnn                                                              10

<210> SEQ ID NO 3
<211> LENGTH: 54
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (26)..(28)
<223> OTHER INFORMATION: n = any nucleotide (e.g., A or G or C or T)
<220> FEATURE:
<221> NAME/KEY: misc_feature
<222> LOCATION: (31)..(33)
<223> OTHER INFORMATION: n = any nucleotide (e.g., A or G or C or T)

<400> SEQUENCE: 3
catcttacga ttacgccaac cactgnnntg nnnctcccga atcaaccctg accc             54

<210> SEQ ID NO 4
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 4
ctattggtgc gggggctttg t                                                 21

<210> SEQ ID NO 5
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 5
ctattggtgc gggggctt                                                     18

```
<210> SEQ ID NO 6
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 6
cggagtacgt gttctcggat                                               20

<210> SEQ ID NO 7
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 7
ctgttctggc gtttcgcagc                                               20

<210> SEQ ID NO 8
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 8
gctcccagct cttgcgtcca tgg                                           23

<210> SEQ ID NO 9
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 9
atccgagaac acgtactccg tgg                                           23

<210> SEQ ID NO 10
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 10
gctgcgaaac gccagaacag cgg                                           23

<210> SEQ ID NO 11
<211> LENGTH: 56
<212> TYPE: DNA
<213> ORGANISM: Artificial Sequence
<220> FEATURE:
<223> OTHER INFORMATION: synthetic nucleotide
<220> FEATURE:
<221> NAME/KEY: misc_feature
<222> LOCATION: (24)..(33)
<223> OTHER INFORMATION: n = any nucleotide (e.g., A or G or C or T)

<400> SEQUENCE: 11
catcttacga ttacgccaac cacnnnnnnn nnngttgaga tgccagagtc agatac       56

<210> SEQ ID NO 12
<211> LENGTH: 22
<212> TYPE: DNA
```

```
<213> ORGANISM: Artificial Sequence
<220> FEATURE:
<223> OTHER INFORMATION: synthetic polynucleotide

<400> SEQUENCE: 12
tgccagcttt gagtacacta tc                                              22

<210> SEQ ID NO 13
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 13
taacctcccg gaccccaagt tcg                                             23

<210> SEQ ID NO 14
<211> LENGTH: 64
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (29)..(33)
<223> OTHER INFORMATION: n = any nucleotide (e.g., A or G or C or T)
<220> FEATURE:
<221> NAME/KEY: misc_feature
<222> LOCATION: (35)..(40)
<223> OTHER INFORMATION: n = any nucleotide (e.g., A or G or C or T)

<400> SEQUENCE: 14
catcttacga ttacgccaac cactgcggnn nnntgnnnnn gacacattct cccaggccct     60
actt                                                                  64

<210> SEQ ID NO 15
<211> LENGTH: 24
<212> TYPE: DNA
<213> ORGANISM: Artificial Sequence
<220> FEATURE:
<223> OTHER INFORMATION: synthetic polypeptide

<400> SEQUENCE: 15
cagagtccct tctgctctct gtcc                                            24

<210> SEQ ID NO 16
<211> LENGTH: 64
<212> TYPE: DNA
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (29)..(33)
<223> OTHER INFORMATION: n = any nucleotide (e.g., A or G or C or T)
<220> FEATURE:
<221> NAME/KEY: misc_feature
<222> LOCATION: (35)..(40)
<223> OTHER INFORMATION: n = any nucleotide (e.g., A or G or C or T)

<400> SEQUENCE: 16
catcttacga ttacgccaac cactgcggnn nnntgnnnnn gcatcccagg cctaatgtgg     60
agtt                                                                  64

<210> SEQ ID NO 17
<211> LENGTH: 24
```

```
<212> TYPE: DNA
<213> ORGANISM: Artificial Sequence
<220> FEATURE:
<223> OTHER INFORMATION: synthetic polynucleotide

<400> SEQUENCE: 17
gtcagatttc cccactgggc tctt                                          24

<210> SEQ ID NO 18
<211> LENGTH: 66
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (29)..(33)
<223> OTHER INFORMATION: n is a, c, g, or t
<220> FEATURE:
<221> NAME/KEY: misc_feature
<222> LOCATION: (36)..(40)
<223> OTHER INFORMATION: n is a, c, g, or t

<400> SEQUENCE: 18
catcttacga ttacgccaac cactgcggnn nnntgnnnnn cctccacgaa acaggatcaa    60
acaacc                                                              66

<210> SEQ ID NO 19
<211> LENGTH: 28
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (29)..(33)
<223> OTHER INFORMATION: n = any nucleotide (e.g., A or G or C or T)
<220> FEATURE:
<221> NAME/KEY: misc_feature
<222> LOCATION: (35)..(40)
<223> OTHER INFORMATION: n = any nucleotide (e.g., A or G or C or T)

<400> SEQUENCE: 19
attgctaggg ccgcgataat aaatggta                                      28

<210> SEQ ID NO 20
<211> LENGTH: 64
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (29)..(33)
<223> OTHER INFORMATION: n = any nucleotide (e.g., A or G or C or T)
<220> FEATURE:
<221> NAME/KEY: misc_feature
<222> LOCATION: (35)..(40)
<223> OTHER INFORMATION: n = any nucleotide (e.g., A or G or C or T)

<400> SEQUENCE: 20
catcttacga ttacgccaac cactgcggnn nnntgnnnnn cgcctgcctg atcctccaaa    60
tcac                                                                64

<210> SEQ ID NO 21
<211> LENGTH: 26
<212> TYPE: DNA
<213> ORGANISM: Artificial Sequence
<220> FEATURE:
```

<223> OTHER INFORMATION: synthetic polynucleotide

<400> SEQUENCE: 21
tgagccgaag tttcatcatg cggaga                                           26

<210> SEQ ID NO 22
<211> LENGTH: 61
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (26)..(30)
<223> OTHER INFORMATION: n = any nucleotide (e.g., A or G or C or T)
<220> FEATURE:
<221> NAME/KEY: misc_feature
<222> LOCATION: (33)..(37)
<223> OTHER INFORMATION: n = any nucleotide (e.g., A or G or C or T)

<400> SEQUENCE: 22
catcttacga ttacgccaac cactgnnnnn tgnnnnntaa caacataccc atggccaacc      60
t                                                                     61

<210> SEQ ID NO 23
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 23
agttttatgc gattaccggg ctct                                             24

<210> SEQ ID NO 24
<211> LENGTH: 12
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(5)
<223> OTHER INFORMATION: n = any nucleotide (e.g., A or G or C or T)
<220> FEATURE:
<221> NAME/KEY: misc_feature
<222> LOCATION: (8)..(12)
<223> OTHER INFORMATION: n = any nucleotide (e.g., A or G or C or T)

<400> SEQUENCE: 24
nnnnntgnnn nn                                                          12

<210> SEQ ID NO 25
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 25
ccatggacgc aagagctggg agc                                              23

<210> SEQ ID NO 26
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 26
acctggccac ggagtacgtg ttctcggatt tcttgctgaa        40

<210> SEQ ID NO 27
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 27
acctggccac ggaagtacgt gttctcggat ttcttgctga        40

<210> SEQ ID NO 28
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 28
acctggccac ggagagtacg tgttctcgga tttcttgctg        40

<210> SEQ ID NO 29
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 29
acagtacgtg ttctcggatt tcttgctgaa        30

<210> SEQ ID NO 30
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 30
accgtacgtg ttctcggatt tcttgctgaa        30

<210> SEQ ID NO 31
<211> LENGTH: 31
<212> TYPE: DNA
<213> ORGANISM: Artificial Sequence
<220> FEATURE:
<223> OTHER INFORMATION: synthetic polynucleotide

<400> SEQUENCE: 31
acctgtacgt gttctcggat ttcttgctga a        31

<210> SEQ ID NO 32
<211> LENGTH: 27
<212> TYPE: DNA
<213> ORGANISM: Artificial Sequence
<220> FEATURE:
<223> OTHER INFORMATION: synthetic polynucleotide

<400> SEQUENCE: 32
acctgtgttc tcggatttct tgctgaa        27

<210> SEQ ID NO 33

```
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 33
acctgatttc ttgctgaa                                                 18

<210> SEQ ID NO 34
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 34
acctggtacg tgttctcgga tttcttgctg aa                                 32

<210> SEQ ID NO 35
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 35
acctggcttc ttgctgaa                                                 18

<210> SEQ ID NO 36
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 36
acctgaacgt acgtgttctc ggtcttgctg aa                                 32

<210> SEQ ID NO 37
<211> LENGTH: 35
<212> TYPE: DNA
<213> ORGANISM: Artificial Sequence
<220> FEATURE:
<223> OTHER INFORMATION: synthetic polynucleotide

<400> SEQUENCE: 37
acctggccac gcgtgttctc ggatttcttg ctgaa                              35

<210> SEQ ID NO 38
<211> LENGTH: 33
<212> TYPE: DNA
<213> ORGANISM: Artificial Sequence
<220> FEATURE:
<223> OTHER INFORMATION: synthetic polynucleotide

<400> SEQUENCE: 38
acctggccac gtgttctcgg atttcttgct gaa                                33

<210> SEQ ID NO 39
<211> LENGTH: 30
<212> TYPE: DNA
<213> ORGANISM: Artificial Sequence
<220> FEATURE:
<223> OTHER INFORMATION: synthetic polynucleotide

<400> SEQUENCE: 39
```

```
acctggccac ggctcggatt tcttgctgaa                                    30

<210> SEQ ID NO 40
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 40
acctggccac ggttctcgga tttcttgctg aa                                 32

<210> SEQ ID NO 41
<211> LENGTH: 33
<212> TYPE: DNA
<213> ORGANISM: Artificial Sequence
<220> FEATURE:
<223> OTHER INFORMATION: synthetic polynucleotide

<400> SEQUENCE: 41
acctggccac ggattctcgg atttcttgct gaa                                33

<210> SEQ ID NO 42
<211> LENGTH: 38
<212> TYPE: DNA
<213> ORGANISM: Artificial Sequence
<220> FEATURE:
<223> OTHER INFORMATION: synthetic polynucleotide

<400> SEQUENCE: 42
acctggccac ggaacgtgtt ctcggatttc ttgctgaa                           38

<210> SEQ ID NO 43
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 43
cctgcccccg ctgttctggc gtttcgcagc tgctcctcat                         40

<210> SEQ ID NO 44
<211> LENGTH: 40
<212> TYPE: DNA
<213> ORGANISM: Artificial Sequence
<220> FEATURE:
<223> OTHER INFORMATION: synthetic polynucleotide

<400> SEQUENCE: 44
cctgcccccg ctgctctggc gtttcgcagc tgctcctcat                         40

<210> SEQ ID NO 45
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 45
cctgcttctg gcgtttcgca gctgctcctc at                                 32

<210> SEQ ID NO 46
<211> LENGTH: 9
<212> TYPE: DNA
```

<213> ORGANISM: Artificial Sequence
<220> FEATURE:
<223> OTHER INFORMATION: synthetic polynucleotide

<400> SEQUENCE: 46 cctgcccat                                                                9

<210> SEQ ID NO 47
<211> LENGTH: 39
<212> TYPE: DNA
<213> ORGANISM: Artificial Sequence
<220> FEATURE:
<223> OTHER INFORMATION: synthetic polynucleotide

<400> SEQUENCE: 47
cctgcccccg ctgtctggcg tttcgcagct gctcctcat                               39

<210> SEQ ID NO 48
<211> LENGTH: 35
<212> TYPE: DNA
<213> ORGANISM: Artificial Sequence
<220> FEATURE:
<223> OTHER INFORMATION: synthetic polynucleotide

<400> SEQUENCE: 48
cctgcccccg ctggcgtttc gcagctgctc ctcat                                   35

<210> SEQ ID NO 49
<211> LENGTH: 34
<212> TYPE: DNA
<213> ORGANISM: Artificial Sequence
<220> FEATURE:
<223> OTHER INFORMATION: synthetic polynucleotide

<400> SEQUENCE: 49
cctgcccccg ctgcgtttcg cagctgctcc tcat                                    34

<210> SEQ ID NO 50
<211> LENGTH: 32
<212> TYPE: DNA
<213> ORGANISM: Artificial Sequence
<220> FEATURE:
<223> OTHER INFORMATION: synthetic polynucleotide

<400> SEQUENCE: 50
cctgcccccg ctgtttcgca gctgctcctc at                                      32

<210> SEQ ID NO 51
<211> LENGTH: 33
<212> TYPE: DNA
<213> ORGANISM: Artificial Sequence
<220> FEATURE:
<223> OTHER INFORMATION: synthetic polynucleotide

<400> SEQUENCE: 51
cctgcccccg ctgttttcgc agctgctcct cat                                     33

<210> SEQ ID NO 52
<211> LENGTH: 55
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (25)..(32)
<223> OTHER INFORMATION: n = any nucleotide (e.g., A or G or C or T)

```
<400> SEQUENCE: 52
cacacgtctg aactccagtc actgnnnnnn nnctcccgaa tcaaccctga ccccct          55

<210> SEQ ID NO 53
<211> LENGTH: 24
<212> TYPE: DNA
<213> ORGANISM: Artificial Sequence
<220> FEATURE:
<223> OTHER INFORMATION: synthetic polynucleotide

<400> SEQUENCE: 53
cacacgtctg aactccagtc actg                                            24

<210> SEQ ID NO 54
<211> LENGTH: 8
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(8)
<223> OTHER INFORMATION: n = any nucleotide (e.g., A or G or C or T)

<400> SEQUENCE: 54 nnnnnnnn                                                               8

<210> SEQ ID NO 55
<211> LENGTH: 23
<212> TYPE: DNA
<213> ORGANISM: Artificial Sequence
<220> FEATURE:
<223> OTHER INFORMATION: synthetic polynucleotide

<400> SEQUENCE: 55
ctcccgaatc aaccctgacc cct                                             23
```